(12) United States Patent
Ellis et al.

(10) Patent No.: US 7,988,964 B2
(45) Date of Patent: Aug. 2, 2011

(54) NOGO-A NEUTRALISING IMMUNOGLOBULIN FOR TREATMENT OF NEUROLOGICAL DISEASES

(75) Inventors: Jonathan Henry Ellis, Stevenage (GB); Alexandre Eon-Duval, Fenil-Sur-Corsier (CH); Robert Ian Grundy, Harlow (GB); Farhana Hussain, Stevenage (GB); Ruth McAdam, Stevenage (GB); Christopher Plumpton, Stevenage (GB); Rabinder Kumar Prinjha, Harlow (GB); Paul Alexander Wilson, Stevenage (GB)

(73) Assignee: Glaxo Group Limited (GB)

( * ) Notice: Subject to any disclaimer, the term of this patent is extended or adjusted under 35 U.S.C. 154(b) by 268 days.

(21) Appl. No.: 10/583,877

(22) PCT Filed: Dec. 20, 2004

(86) PCT No.: PCT/GB2004/005325
§ 371 (c)(1),
(2), (4) Date: Jun. 21, 2006

(87) PCT Pub. No.: WO2005/061544
PCT Pub. Date: Jul. 7, 2005

(65) Prior Publication Data
US 2007/0065430 A1    Mar. 22, 2007

(30) Foreign Application Priority Data

Dec. 22, 2003  (GB) .................................. 0329684.5
Dec. 22, 2003  (GB) .................................. 0329711.6

(51) Int. Cl.
*A61K 39/395* (2006.01)
*A61K 39/00* (2006.01)
*A61K 38/00* (2006.01)
*C12P 21/08* (2006.01)
*C07K 16/00* (2006.01)

(52) U.S. Cl. ............... 424/130.1; 424/133.1; 424/139.1; 424/141.1; 424/143.1; 514/17.7; 530/387.1; 530/387.3; 530/388.2; 530/389.1

(58) Field of Classification Search .................... None
See application file for complete search history.

(56) References Cited

U.S. PATENT DOCUMENTS 6,420,388 B1    7/2002    Emonds-Alt et al.

FOREIGN PATENT DOCUMENTS

| WO | WO 95/32948    | 12/1995 |
|----|----------------|---------|
| WO | WO 2004/052932 | 6/2004  |
| WO | WO 2005/014575 | 2/2005  |
| WO | WO 2005028508  | 3/2005  |
| WO | WO 2005/061544 | 7/2005  |
| WO | WO 2005/061545 | 7/2005  |

OTHER PUBLICATIONS

Caroni et al., Neuron, 1(1):85-96, (1988).*
Zander et al. Journal of Molecular Recognition, 20:185-196, May 2007.*
Fiedler et al. Protein Engineering 15(11):931-941, Nov. 2002.*
Rudikoff et al. Proc Natl Acad Sci USA, 1982 vol. 79.*
MacCallum et al. J. Mol. Biol. (1996) 262, 732-745.*
Pascalis et al. The Journal of Immunology (2002) 169, 3076-3084.*
Casset et al. (2003) BBRC 307, 198-205.*
Vajdos et al. Journal of Molecular Biology. (2002) 320, 415-428.*
Chen et al. J. Mol. Bio. (1999) 293, 865-881.*
Wu et al. J. Mol. Biol. (1999) 294, 151-162.*
Holm et al. Molecular Immunology, (2007) 44, 1075-1084.*
Giardina, et al., "Discovery of a Novel Class of Selective Non-peptide Antagonists for the Human Neurokinin-3 Receptor. 2. Identification of (S)-N-(1-Phenylpropyl)-3Hydroxy-2-Phenylquinoli NE-4-Carboxamide (SB 223412)," *Journal of Medicinal Chemistry*, vol. 42, No. 6, pp. 1053-1065 (1999).
Pemberton, et al., "Effects of a NK-3 Receptor Antagonist on ICV Administered Senktide—Induced Behaviours in the Guinea Pig," *Society for Neuroscience Abstract Viewer and Itinerary Planner*, vol. 2003, abstract No. 858.6 (2003).
Glick, et al., "Psychopharmacologic Treatment Strategies for Depression, Bipolar Disorder, and Schizophrenia," *Annals of Internal Medicine*, vol. 134, No. 1, pp. 47-60 (2001).
Bandtlow, et al., European Journal of Biochemistry, vol. 241, No. 2, pp. 468-475, 1996.
Bareyre, et al., The Journal of Neuroscience, vol. 22, No. 16, pp. 7097-7110, Aug. 15, 2002.
Brosamle, et al., The Journal of Neuroscience, vol. 20, No. 21, pp. 8061-8068, Nov. 1, 2000.
Emerick, et al., The Journal of Neuroscience, vol. 23, No. 12, pp. 4826-4830 Jun. 2003.
Karim, et al., Brain Research Reviews, vol. 36, pp. 204-212, 2001.
Papadopoulos, et al., Ann. Neurol. vol. 51, pp. 433-441, 2002.
Reindl, et al., Journal of Neuroimmunology, vol. 145., No. 1, pp. 139-147, 2003.
Schmidlin, et al., Program No. 275.9. 2003 Abstract Viewer/Itinerary Planner. Washington, DC: Society for Neuroscience, 2003. Online.
Schnell, et al., Program No. 678.9. 2003 Abstract Viewer/Itinerary Planner. Washington DC: Society for Neuroscience, 2003. Online.
Schwab, et al., Program No. 678.5. 2003 Abstract Viewer/Itinerary Planner. Washington DC: Society for Neuroscience, 2003. Online.
Wiessner, et al., Journal of Cerebral Blood Flow & Metabolism, vol. 23, pp. 154-165, 2003.

* cited by examiner

*Primary Examiner* — Lorraine Spector
*Assistant Examiner* — Stacey MacFarlane
(74) *Attorney, Agent, or Firm* — Jonathan M. Dermott; William T. Han

(57) ABSTRACT

The present invention provides immunoglobulins, particularly antibodies that bind to NOGO and neutralise the activity thereof, polynucleotides encoding such antibodies, pharmaceutical formulations containing said antibodies and to the use of such antibodies in the treatment and/or prophylaxis of neurological diseases.

12 Claims, 45 Drawing Sheets

SEQUENCE LISTING

<160> NUMBER OF SEQ ID NOS: 97

<210> SEQ ID NO 1
<211> LENGTH: 16
<212> TYPE: PRT
<213> ORGANISM: Mus musculus

<400> SEQUENCE: 1

```
Arg Ser Ser Lys Ser Leu Leu Tyr Lys Asp Gly Lys Thr Tyr Leu Asn
1               5                   10                  15

<210> SEQ ID NO 2
<211> LENGTH: 7
<212> TYPE: PRT
<213> ORGANISM: Mus musculus

<400> SEQUENCE: 2

Leu Met Ser Thr Arg Ala Ser
1               5

<210> SEQ ID NO 3
<211> LENGTH: 9
<212> TYPE: PRT
<213> ORGANISM: Mus musculus

<400> SEQUENCE: 3

Gln Gln Leu Val Glu Tyr Pro Leu Thr
1               5

<210> SEQ ID NO 4
<211> LENGTH: 5
<212> TYPE: PRT
<213> ORGANISM: Mus musculus

<400> SEQUENCE: 4

Ser Tyr Trp Met His
1               5

<210> SEQ ID NO 5
<211> LENGTH: 17
<212> TYPE: PRT
<213> ORGANISM: Mus musculus

<400> SEQUENCE: 5

Asn Ile Asn Pro Ser Asn Gly Gly Thr Asn Tyr Asn Glu Lys Phe Lys
1               5                   10                  15

Ser

<210> SEQ ID NO 6
<211> LENGTH: 4
<212> TYPE: PRT
<213> ORGANISM: Mus musculus

<400> SEQUENCE: 6

Gly Gln Gly Tyr
1

<210> SEQ ID NO 7
<211> LENGTH: 16
<212> TYPE: PRT
<213> ORGANISM: Mus musculus

<400> SEQUENCE: 7

Arg Ser Ser Gln Ser Leu Val His Ser Asn Gly Asn Thr Tyr Leu His
1               5                   10                  15

<210> SEQ ID NO 8
<211> LENGTH: 7
<212> TYPE: PRT
<213> ORGANISM: Mus musculus

<400> SEQUENCE: 8
```

```
Lys Val Ser Asn Arg Phe Ser
1               5

<210> SEQ ID NO 9
<211> LENGTH: 9
<212> TYPE: PRT
<213> ORGANISM: Mus musculus

<400> SEQUENCE: 9

Ser Gln Ser Thr His Val Pro Leu Thr
1               5

<210> SEQ ID NO 10
<211> LENGTH: 7
<212> TYPE: PRT
<213> ORGANISM: Mus musculus

<400> SEQUENCE: 10

Phe Ser Cys Tyr Ala Met Ser
1               5

<210> SEQ ID NO 11
<211> LENGTH: 17
<212> TYPE: PRT
<213> ORGANISM: Mus musculus

<400> SEQUENCE: 11

Ser Ile Ser Asp Gly Gly Ser Tyr Thr Tyr Tyr Pro Asp Asn Val Lys
1               5                   10                  15

Gly

<210> SEQ ID NO 12
<211> LENGTH: 6
<212> TYPE: PRT
<213> ORGANISM: Mus musculus

<400> SEQUENCE: 12

Glu Leu Leu Phe Asp Tyr
1               5

<210> SEQ ID NO 13
<211> LENGTH: 16
<212> TYPE: PRT
<213> ORGANISM: Mus musculus

<400> SEQUENCE: 13

Arg Ser Ser Lys Ser Leu Leu His Ser Asn Gly Asn Thr Tyr Leu Tyr
1               5                   10                  15

<210> SEQ ID NO 14
<211> LENGTH: 7
<212> TYPE: PRT
<213> ORGANISM: Mus musculus

<400> SEQUENCE: 14

Arg Met Ser Asn Leu Ala Ser
1               5

<210> SEQ ID NO 15
<211> LENGTH: 9
<212> TYPE: PRT
<213> ORGANISM: Mus musculus

<400> SEQUENCE: 15

Met Gln His Leu Glu Tyr Pro Leu Thr
```

```
<210> SEQ ID NO 16
<211> LENGTH: 5
<212> TYPE: PRT
<213> ORGANISM: Mus musculus

<400> SEQUENCE: 16

Ser Tyr Trp Met Asn
1               5

<210> SEQ ID NO 17
<211> LENGTH: 17
<212> TYPE: PRT
<213> ORGANISM: Mus musculus

<400> SEQUENCE: 17

Gln Ile Tyr Pro Gly Asp Gly Asp Thr Asn Tyr Asn Gly Lys Phe Lys
1               5                   10                  15

Gly

<210> SEQ ID NO 18
<211> LENGTH: 4
<212> TYPE: PRT
<213> ORGANISM: Mus musculus

<400> SEQUENCE: 18

Arg Phe Asp Tyr
1

<210> SEQ ID NO 19
<211> LENGTH: 48
<212> TYPE: DNA
<213> ORGANISM: Mus musculus

<400> SEQUENCE: 19
aggtctagta agagtctcct atataaggat gggaagacat acttgaat            48

<210> SEQ ID NO 20
<211> LENGTH: 21
<212> TYPE: DNA
<213> ORGANISM: Mus musculus

<400> SEQUENCE: 20
ttgatgtcca cccgtgcatc a                                         21

<210> SEQ ID NO 21
<211> LENGTH: 27
<212> TYPE: DNA
<213> ORGANISM: Mus musculus

<400> SEQUENCE: 21
caacaacttg tagagtatcc gctcacg                                   27

<210> SEQ ID NO 22
<211> LENGTH: 15
<212> TYPE: DNA
<213> ORGANISM: Mus musculus

<400> SEQUENCE: 22
agctactgga tgcac                                                15

<210> SEQ ID NO 23
<211> LENGTH: 51
```

```
<212> TYPE: DNA
<213> ORGANISM: Mus musculus

<400> SEQUENCE: 23
aatattaatc ctagcaatgg tggtactaac tacaatgaga agttcaagag c                51

<210> SEQ ID NO 24
<211> LENGTH: 12
<212> TYPE: DNA
<213> ORGANISM: Mus musculus

<400> SEQUENCE: 24
ggacagggct ac                                                            12

<210> SEQ ID NO 25
<211> LENGTH: 48
<212> TYPE: DNA
<213> ORGANISM: Mus musculus

<400> SEQUENCE: 25
agatctagtc agagccttgt acacagtaat ggaaacacct atttacat                     48

<210> SEQ ID NO 26
<211> LENGTH: 21
<212> TYPE: DNA
<213> ORGANISM: Mus musculus

<400> SEQUENCE: 26
aaagtttcca accgattttc t                                                  21

<210> SEQ ID NO 27
<211> LENGTH: 27
<212> TYPE: DNA
<213> ORGANISM: Mus musculus

<400> SEQUENCE: 27
tctcagagta cacatgttcc gctcacg                                            27

<210> SEQ ID NO 28
<211> LENGTH: 21
<212> TYPE: DNA
<213> ORGANISM: Mus musculus

<400> SEQUENCE: 28
ttcagttgct atgccatgtc t                                                  21

<210> SEQ ID NO 29
<211> LENGTH: 51
<212> TYPE: DNA
<213> ORGANISM: Mus musculus

<400> SEQUENCE: 29
tccattagtg atggtggtag ttacacctac tatccagaca atgtaaaggg c                 51

<210> SEQ ID NO 30
<211> LENGTH: 18
<212> TYPE: DNA
<213> ORGANISM: Mus musculus

<400> SEQUENCE: 30
gaactacttt ttgactac                                                      18

<210> SEQ ID NO 31
<211> LENGTH: 48
```

```
<212> TYPE: DNA
<213> ORGANISM: Mus musculus

<400> SEQUENCE: 31
aggtctagta agagtctcct gcatagtaat ggcaacactt acttgtat         48

<210> SEQ ID NO 32
<211> LENGTH: 21
<212> TYPE: DNA
<213> ORGANISM: Mus musculus

<400> SEQUENCE: 32
cggatgtcca accttgcctc a                                      21

<210> SEQ ID NO 33
<211> LENGTH: 27
<212> TYPE: DNA
<213> ORGANISM: Mus musculus

<400> SEQUENCE: 33
atgcaacatc tagaatatcc gctcacg                                27

<210> SEQ ID NO 34
<211> LENGTH: 15
<212> TYPE: DNA
<213> ORGANISM: Mus musculus

<400> SEQUENCE: 34
agctactgga tgaac                                             15

<210> SEQ ID NO 35
<211> LENGTH: 51
<212> TYPE: DNA
<213> ORGANISM: Mus musculus

<400> SEQUENCE: 35
cagatttatc ctggagatgg tgatactaac tacaacggaa agttcaaggg c      51

<210> SEQ ID NO 36
<211> LENGTH: 12
<212> TYPE: DNA
<213> ORGANISM: Mus musculus

<400> SEQUENCE: 36
cgctttgact at                                                12

<210> SEQ ID NO 37
<211> LENGTH: 113
<212> TYPE: PRT
<213> ORGANISM: Mus musculus

<400> SEQUENCE: 37
```

Gln Val Gln Leu Gln Gln Pro Gly Thr Glu Leu Val Lys Pro Gly Ala
 1               5                  10                  15

Ser Val Lys Leu Ser Cys Lys Ala Ser Gly Tyr Thr Phe Thr Ser Tyr
             20                  25                  30

Trp Met His Val Lys Gln Arg Pro Gly Gln Gly Leu Glu Trp Ile
         35                  40                  45

Gly Asn Ile Asn Pro Ser Asn Gly Gly Thr Asn Tyr Asn Glu Lys Phe
     50                  55                  60

Lys Ser Lys Ala Thr Leu Thr Val Asp Lys Ser Ser Ser Thr Ala Tyr
65                   70                  75                  80

```
Met Gln Leu Ser Ser Leu Thr Ser Glu Asp Ser Ala Val Tyr Tyr Cys
            85                  90                  95

Glu Leu Gly Gln Gly Tyr Trp Gly Gln Gly Thr Thr Leu Thr Val Ser
        100                 105                 110

Ser

<210> SEQ ID NO 38
<211> LENGTH: 115
<212> TYPE: PRT
<213> ORGANISM: Mus musculus

<400> SEQUENCE: 38

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Cys Tyr
            20                  25                  30

Ala Met Ser Trp Val Arg Gln Thr Pro Glu Lys Arg Leu Glu Trp Val
        35                  40                  45

Ala Ser Ile Ser Asp Gly Gly Ser Tyr Thr Tyr Tyr Pro Asp Asn Val
    50                  55                  60

Lys Gly Arg Phe Thr Ile Ser Arg Asp Asn Ala Lys Asn Asn Leu Tyr
65                  70                  75                  80

Leu Gln Met Ser His Leu Lys Ser Glu Asp Thr Ala Met Tyr Tyr Cys
            85                  90                  95

Ala Lys Glu Leu Leu Phe Asp Tyr Trp Gly Gln Gly Thr Thr Leu Thr
        100                 105                 110

Val Ser Ser
        115

<210> SEQ ID NO 39
<211> LENGTH: 113
<212> TYPE: PRT
<213> ORGANISM: Mus musculus

<400> SEQUENCE: 39

Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Lys Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
            85                  90                  95

Ala Val Arg Phe Asp Tyr Trp Gly Gln Gly Thr Thr Leu Thr Val Ser
        100                 105                 110

Ser

<210> SEQ ID NO 40
<211> LENGTH: 112
<212> TYPE: PRT
<213> ORGANISM: Mus musculus

<400> SEQUENCE: 40

Asp Ile Val Ile Thr Gln Asp Glu Leu Ser Asn Pro Val Thr Ser Gly
```

```
                1               5                  10                 15
Glu Ser Val Ser Ile Ser Cys Arg Ser Ser Lys Ser Leu Leu Tyr Lys
                20                 25                 30

Asp Gly Lys Thr Tyr Leu Asn Trp Phe Leu Gln Arg Pro Gly Gln Ser
            35                 40                 45

Pro Gln Leu Leu Ile Tyr Leu Met Ser Thr Arg Ala Ser Gly Val Ser
        50                 55                 60

Asp Arg Phe Ser Gly Ser Gly Ser Gly Thr Asp Phe Thr Leu Glu Ile
65                  70                 75                 80

Ser Arg Val Lys Ala Glu Asp Val Gly Val Tyr Tyr Cys Gln Gln Leu
                85                 90                 95

Val Glu Tyr Pro Leu Thr Phe Gly Ala Gly Thr Lys Leu Glu Leu Lys
            100                105                110
```

<210> SEQ ID NO 41
<211> LENGTH: 112
<212> TYPE: PRT
<213> ORGANISM: Mus musculus

<400> SEQUENCE: 41

```
Asp Val Val Met Thr Gln Thr Pro Leu Ser Leu Pro Val Ser Leu Gly
1               5                  10                 15

Asp Gln Ala Ser Ile Ser Cys Arg Ser Ser Gln Ser Leu Val His Ser
                20                 25                 30

Asn Gly Asn Thr Tyr Leu His Trp Tyr Leu Gln Lys Pro Gly Gln Ser
            35                 40                 45

Pro Lys Leu Leu Ile Tyr Lys Val Ser Asn Arg Phe Ser Gly Val Pro
        50                 55                 60

Asp Arg Phe Ser Gly Ser Gly Ser Gly Thr Asp Phe Thr Leu Lys Ile
65                  70                 75                 80

Ser Arg Val Glu Ala Glu Asp Leu Gly Val Tyr Phe Cys Ser Gln Ser
                85                 90                 95

Thr His Val Pro Leu Thr Phe Gly Ala Gly Thr Lys Leu Glu Leu Lys
            100                105                110
```

<210> SEQ ID NO 42
<211> LENGTH: 112
<212> TYPE: PRT
<213> ORGANISM: Mus musculus

<400> SEQUENCE: 42

```
Asp Ile Val Met Thr Gln Ala Ala Pro Ser Val Pro Val Thr Pro Gly
1               5                  10                 15

Glu Ser Val Ser Ile Ser Cys Arg Ser Ser Lys Ser Leu Leu His Ser
                20                 25                 30

Asn Gly Asn Thr Tyr Leu Tyr Trp Phe Leu Gln Arg Pro Gly Gln Ser
            35                 40                 45

Pro Gln Leu Leu Ile Tyr Arg Met Ser Asn Leu Ala Ser Gly Val Pro
        50                 55                 60

Asp Arg Phe Ser Gly Ser Gly Ser Gly Thr Ala Phe Thr Leu Arg Ile
65                  70                 75                 80

Ser Arg Val Glu Ala Glu Asp Val Gly Val Tyr Tyr Cys Met Gln His
                85                 90                 95

Leu Glu Tyr Pro Leu Thr Phe Gly Ala Gly Thr Lys Leu Glu Leu Lys
            100                105                110
```

<210> SEQ ID NO 43

```
<211> LENGTH: 339
<212> TYPE: DNA
<213> ORGANISM: Mus musculus

<400> SEQUENCE: 43
caggtccaac tgcagcagcc tgggactgaa ctggtgaagc ctggggcttc agtgaagctg      60
tcctgcaagg cttctggcta caccttcacc agctactgga tgcactgggt gaagcagagg     120
cctggacaag gccttgagtg gattggaaat attaatccta gcaatggtgg tactaactac     180
aatgagaagt tcaagagcaa ggccacactg actgtagaca atcctccag cacagcctac      240 atgcagctca gcagcctgac atctgaggac tctgcggtct attattgtga actgggacag     300
ggctactggg gccaaggcac cactctcaca gtctcctca                            339

<210> SEQ ID NO 44
<211> LENGTH: 345
<212> TYPE: DNA
<213> ORGANISM: Mus musculus

<400> SEQUENCE: 44
gaagtgcagc tggtggagtc tgggggaggc ttagtgaagc ctggagggtc cctgaaactc      60
tcctgtgcag cctctggatt cactttcagt tgctatgcca tgtcttgggt tcgccagact     120
ccggaaaaga ggctggagtg ggtcgcatcc attagtgatg gtggtagtta cacctactat     180
ccagacaatg taaagggccg attcaccatc tccagagaca atgccaagaa caacctgtac     240
ctgcaaatga gccatctgaa gtctgaggac acagccatgt attactgtgc aaaggaacta     300 cttttttgact actggggcca aggcaccact ctcacagtct cctca                    345

<210> SEQ ID NO 45
<211> LENGTH: 339
<212> TYPE: DNA
<213> ORGANISM: Mus musculus

<400> SEQUENCE: 45
caggttcagc tgcagcagtc tggggctgag ctggtgaagc ctggggcctc agtgaagatt      60
tcctgcaaag cttctggcta cgcattcagt agctactgga tgaactgggt gaagcagagg     120
cctggaaagg gtcttgagtg gattggacag atttatcctg agatggtga tactaactac      180 aacgaaaagt tcaagggcaa ggccacactg actgcagaca atcctccag cacagcctac      240 atgcagctca gcagcctgac ctctgaggac tctgcggtct atttctgtgc agtacgcttt     300
gactattggg gccaaggcac cactctcaca gtctcctca                            339

<210> SEQ ID NO 46
<211> LENGTH: 336
<212> TYPE: DNA
<213> ORGANISM: Mus musculus

<400> SEQUENCE: 46
gatattgtga taacccagga tgaactctcc aatcctgtca cttctggaga atcagtttcc      60
atctcctgca ggtctagtaa gagtctccta tataaggatg gaagacata cttgaattgg     120 tttctgcaga gaccaggaca atcctcctcag ctcctgatct atttgatgtc cacccgtgca     180
tcaggagtct cagaccggtt tagtggcagt gggtcaggaa cagatttcac cctgaaaatc      240
agtagagtga aggctgagga tgtgggtgtg tattactgtc aacaacttgt agagtatccg      300
ctcacgttcg gtgctgggac caagctggag ctgaaa                               336

<210> SEQ ID NO 47
```

```
<211> LENGTH: 336
<212> TYPE: DNA
<213> ORGANISM: Mus musculus

<400> SEQUENCE: 47
gatgttgtga tgacccaaac tccactctcc ctgcctgtca gtcttggaga tcaagcctcc      60
atctcttgca gatctagtca gagccttgta cacagtaatg aaacaccta tttacattgg     120
tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcagagtac acatgttccg     300
ctcacgttcg gtgctgggac caagctggag ctgaaa                                336

<210> SEQ ID NO 48
<211> LENGTH: 336
<212> TYPE: DNA
<213> ORGANISM: Mus musculus

<400> SEQUENCE: 48
gatattgtga tgactcaggc tgcaccctct gtacctgtca ctcctggaga gtcagtatcc      60
atctcctgca ggtctagtaa gagtctcctg catagtaatg gcaacactta cttgtattgg     120
ttcctgcaga ggccaggcca gtctcctcag ctcctgatat atcggatgtc caaccttgcc     180
tcaggagtcc cagacaggtt cagtggcagt gggtcaggaa ctgctttcac actgagaatc     240
agtagagtgg aggctgagga tgtgggtgtt tattactgta tgcaacatct agaatatccg     300
ctcacgttcg gtgctgggac caagctggag ctgaaa                                336

<210> SEQ ID NO 49
<211> LENGTH: 1407
<212> TYPE: DNA
<213> ORGANISM: Mus musculus

<400> SEQUENCE: 49
aagcttgcca ccatgggatg gagctgtatc atcctctttt tggtagcagc agctacaggt      60
gtccactccc aggtccaact gcagcagcct gggactgaac tggtgaagcc tggggcttca     120
gtgaagctgt cctgcaaggc ttctggctac accttcacca gctactggat gcactgggtg     180
aagcagaggc ctggacaagg ccttgagtgg attggaaata ttaatcctag caatggtggt     240
actaactaca tgagaagtt caagagcaag gccacactga ctgtagacaa atcctccagc     300
acagcctaca tgcagctcag cagcctgaca tctgaggact ctgcggtcta ttattgtgaa     360
ctgggacagg gctactgggg ccaaggcaca ctagtcaccg tctcctcagc caaaacaaca     420
gccccatcgg tctatccact ggcccctgtg tgtggagata aactggctc ctcggtgact     480
ctaggatgcc tggtcaaggg ttatttccct gagccagtga ccttgacctg gaactctgga     540
tccctgtcca gtggtgtgca caccttccca gctgtcctgc agtctgacct ctacaccctc     600
agcagctcag tgactgtaac ctcgagcacc tggcccagcc agtccatcac ctgcaatgtg     660
gcccacccgg caagcagcac caaggtggac aagaaaattg agcccagagg gcccacaatc     720
aagccctgtc ctccatgcaa atgcccagca cctaacctcc tgggtggccc atccgtcttc     780
atcttccctc caaagatcaa ggatgtactc atgatctccc tgagccccat agtcacatgt     840
gtggtggtgg atgtgagcga ggatgaccca gatgtccaga tcagctggtt tgtgaacaac     900
gtggaagtac acacagctca gacacaaacc catagagagg attacaacag tactctccgg     960
gtggtcagtg ccctccccat ccagcaccag gactggatga gtggcaagga gttcaaatgc    1020
```

```
aaggtcaaca acaaagacct cccagcgccc atcgagagaa ccatctcaaa acccaaaggg      1080
tcagtaagag ctccacaggt atatgtcttg cctccaccag aagaagagat gactaagaaa      1140
caggtcactc tgacctgcat ggtcacagac ttcatgcctg aagacattta cgtggagtgg      1200
accaacaacg ggaaaacaga gctaaactac aagaacactg aaccagtcct ggactctgat      1260
ggttcttact tcatgtacag caagctgaga gtggaaaaga gaactgggt ggaaagaaat       1320 agctactcct gttcagtggt ccacgagggt ctgcacaatc accacacgac taagagcttc      1380
tcccggactc cgggtaaatg agaattc                                          1407

<210> SEQ ID NO 50
<211> LENGTH: 738
<212> TYPE: DNA
<213> ORGANISM: Mus musculus

<400> SEQUENCE: 50
aagcttgcca ccatgaggtg ctctcttcag tttctggggg tgcttatgtt ctggatctct        60
ggagtcagtg gggatattgt gataacccag gatgaactct ccaatcctgt cacttctgga      120
gaatcagttt ccatctcctg caggtctagt aagagtctcc tatataagga tgggaagaca      180
tacttgaatt ggtttctgca gagaccagga caatctcctc agctcctgat ctatttgatg      240
tccacccgtg catcaggagt ctcagaccgg tttagtggca gtgggtcagg aacagatttc      300
accctggaaa tcagtagagt gaaggctgag gatgtgggtg tgtattactg tcaacaactt      360
gtagagtatc cgctcacgtt cggtgctggg accaagctgg agctgaaacg tacggatgct      420
gcaccgactg tatccatctt cccaccatcc agtgagcagt taacatctgg aggtgcctca      480
gtcgtgtgct tcttgaacaa cttctacccc aaagacatca atgtcaagtg gaagattgat      540
ggcagtgaac gacaaaatgg cgtcctgaac agttggactg atcaggacag caaagacagc      600
acctacagca tgagcagcac cctcacgttg accaaggacg agtatgaacg acataacagc      660
tatacctgtg aggccactca caagacatca acttcaccca ttgtcaagag cttcaacagg      720
aatgagtgtt aagaattc                                                    738

<210> SEQ ID NO 51
<211> LENGTH: 37
<212> TYPE: DNA
<213> ORGANISM: Artificial sequence
<220> FEATURE:
<223> OTHER INFORMATION: Murine VH leader sequence forward primer

<400> SEQUENCE: 51
actagtcgac atgaaatgca gctgggtcat sttcttc                                37

<210> SEQ ID NO 52
<211> LENGTH: 36
<212> TYPE: DNA
<213> ORGANISM: Artificial sequence
<220> FEATURE:
<223> OTHER INFORMATION: Murine VH leader sequence forward primer

<400> SEQUENCE: 52
actagtcgac atgggatgga gctrtatcat sytctt                                 36

<210> SEQ ID NO 53
<211> LENGTH: 37
<212> TYPE: DNA
<213> ORGANISM: Artificial sequence
<220> FEATURE:
<223> OTHER INFORMATION: Murine VH leader sequence forward primer
```

```
<400> SEQUENCE: 53
actagtcgac atgaagwtgt ggttaaactg ggttttt                          37

<210> SEQ ID NO 54
<211> LENGTH: 35
<212> TYPE: DNA
<213> ORGANISM: Artificial sequence
<220> FEATURE:
<223> OTHER INFORMATION: Murine VH leader sequence forward primer

<400> SEQUENCE: 54
actagtcgac atgractttg ggytcagctt grttt                            35

<210> SEQ ID NO 55
<211> LENGTH: 40
<212> TYPE: DNA
<213> ORGANISM: Artificial sequence
<220> FEATURE:
<223> OTHER INFORMATION: Murine VH leader sequence forward primer

<400> SEQUENCE: 55
actagtcgac atggactcca ggctcaattt agttttcctt                       40

<210> SEQ ID NO 56
<211> LENGTH: 37
<212> TYPE: DNA
<213> ORGANISM: Artificial sequence
<220> FEATURE:
<223> OTHER INFORMATION: Murine VH leader sequence forward primer

<400> SEQUENCE: 56
actagtcgac atggctgtcy trgsgctrct cttctgc                          37

<210> SEQ ID NO 57
<211> LENGTH: 36
<212> TYPE: DNA
<213> ORGANISM: Artificial sequence
<220> FEATURE:
<223> OTHER INFORMATION: Murine VH leader sequence forward primer

<400> SEQUENCE: 57
actagtcgac atggratgga gckggrtctt tmtctt                           36

<210> SEQ ID NO 58
<211> LENGTH: 33
<212> TYPE: DNA
<213> ORGANISM: Artificial sequence
<220> FEATURE:
<223> OTHER INFORMATION: Murine VH leader sequence forward primer

<400> SEQUENCE: 58
actagtcgac atgagagtgc tgattctttt gtg                              33

<210> SEQ ID NO 59
<211> LENGTH: 40
<212> TYPE: DNA
<213> ORGANISM: Artificial sequence
<220> FEATURE:
<223> OTHER INFORMATION: Murine VH leader sequence forward primer

<400> SEQUENCE: 59
actagtcgac atggmttggg tgtggamctt gctattcctg                       40

<210> SEQ ID NO 60
<211> LENGTH: 37
<212> TYPE: DNA
```

```
<213> ORGANISM: Artificial sequence
<220> FEATURE:
<223> OTHER INFORMATION: Murine VH leader sequence forward primer

<400> SEQUENCE: 60
actagtcgac atgggcagac ttacattctc attcctg                              37

<210> SEQ ID NO 61
<211> LENGTH: 38
<212> TYPE: DNA
<213> ORGANISM: Artificial sequence
<220> FEATURE:
<223> OTHER INFORMATION: Murine VH leader sequence forward primer

<400> SEQUENCE: 61
actagtcgac atggattttg ggctgatttt ttttattg                             38

<210> SEQ ID NO 62
<211> LENGTH: 37
<212> TYPE: DNA
<213> ORGANISM: Artificial sequence
<220> FEATURE:
<223> OTHER INFORMATION: Murine VH leader sequence forward primer

<400> SEQUENCE: 62
actagtcgac atgatggtgt taagtcttct gtacctg                              37

<210> SEQ ID NO 63
<211> LENGTH: 40
<212> TYPE: DNA
<213> ORGANISM: Artificial sequence
<220> FEATURE:
<223> OTHER INFORMATION: Murine VL leader sequence forward primer

<400> SEQUENCE: 63
actagtcgac atgaagttgc ctgttaggct gttggtgctg                           40

<210> SEQ ID NO 64
<211> LENGTH: 39
<212> TYPE: DNA
<213> ORGANISM: Artificial sequence
<220> FEATURE:
<223> OTHER INFORMATION: Murine VL leader sequence forward primer

<400> SEQUENCE: 64
actagtcgac atggagwcag acacactcct gytatgggt                            39

<210> SEQ ID NO 65
<211> LENGTH: 40
<212> TYPE: DNA
<213> ORGANISM: Artificial sequence
<220> FEATURE:
<223> OTHER INFORMATION: Murine VL leader sequence forward primer

<400> SEQUENCE: 65
actagtcgac atgagtgtgc tcactcaggt cctggcgttg                           40

<210> SEQ ID NO 66
<211> LENGTH: 43
<212> TYPE: DNA
<213> ORGANISM: Artificial sequence
<220> FEATURE:
<223> OTHER INFORMATION: Murine VL leader sequence forward primer

<400> SEQUENCE: 66
actagtcgac atgaggrccc ctgctcagwt tyttggmwtc ttg                       43
```

<210> SEQ ID NO 67
<211> LENGTH: 40
<212> TYPE: DNA
<213> ORGANISM: Artificial sequence
<220> FEATURE:
<223> OTHER INFORMATION: Murine VL leader sequence forward primer

<400> SEQUENCE: 67
actagtcgac atggatttwc aggtgcagat twtcagcttc                                40

<210> SEQ ID NO 68
<211> LENGTH: 37
<212> TYPE: DNA
<213> ORGANISM: Artificial sequence
<220> FEATURE:
<223> OTHER INFORMATION: Murine VL leader sequence forward primer

<400> SEQUENCE: 68
actagtcgac atgaggtkcy ytgytsagyt yctgrgg                                   37

<210> SEQ ID NO 69
<211> LENGTH: 41
<212> TYPE: DNA
<213> ORGANISM: Artificial sequence
<220> FEATURE:
<223> OTHER INFORMATION: Murine VL leader sequence forward primer

<400> SEQUENCE: 69
actagtcgac atgggcwtca agatggagtc acakwyycwg g                              41

<210> SEQ ID NO 70
<211> LENGTH: 41
<212> TYPE: DNA
<213> ORGANISM: Artificial sequence
<220> FEATURE:
<223> OTHER INFORMATION: Murine VL leader sequence forward primer

<400> SEQUENCE: 70
actagtcgac atgtggggay ctktttycmm tttttcaatt g                              41

<210> SEQ ID NO 71
<211> LENGTH: 35
<212> TYPE: DNA
<213> ORGANISM: Artificial sequence
<220> FEATURE:
<223> OTHER INFORMATION: Murine VL leader sequence forward primer

<400> SEQUENCE: 71
actagtcgac atggtrtccw casctcagtt ccttg                                     35

<210> SEQ ID NO 72
<211> LENGTH: 37
<212> TYPE: DNA
<213> ORGANISM: Artificial sequence
<220> FEATURE:
<223> OTHER INFORMATION: Murine VL leader sequence forward primer

<400> SEQUENCE: 72
actagtcgac atgtatatat gtttgttgtc tatttct                                   37

<210> SEQ ID NO 73
<211> LENGTH: 38
<212> TYPE: DNA
<213> ORGANISM: Artificial sequence
<220> FEATURE:
<223> OTHER INFORMATION: Murine VL leader sequence forward primer -continued

```
<400> SEQUENCE: 73
actagtcgac atggaagccc cagctcagct tctcttcc                            38

<210> SEQ ID NO 74
<211> LENGTH: 37
<212> TYPE: DNA
<213> ORGANISM: Artificial sequence
<220> FEATURE:
<223> OTHER INFORMATION: Murine VL leader sequence forward primer

<400> SEQUENCE: 74
actagtcgac atgaagtttc cttctcaact tctgctc                             37

<210> SEQ ID NO 75
<211> LENGTH: 28
<212> TYPE: DNA
<213> ORGANISM: Artificial sequence
<220> FEATURE:
<223> OTHER INFORMATION: Murine gamma 1 constant region reverse primer

<400> SEQUENCE: 75
ggatcccggg ccagtggata gacagatg                                       28

<210> SEQ ID NO 76
<211> LENGTH: 27
<212> TYPE: DNA
<213> ORGANISM: Artificial sequence
<220> FEATURE:
<223> OTHER INFORMATION: Murine gamma 2b constant region reverse primer

<400> SEQUENCE: 76
ggatcccggg agtggataga ctgatgg                                        27

<210> SEQ ID NO 77
<211> LENGTH: 27
<212> TYPE: DNA
<213> ORGANISM: Artificial sequence
<220> FEATURE:
<223> OTHER INFORMATION: Murine kappa constant region reverse primer

<400> SEQUENCE: 77
ggatcccggg tggatggtgg gaagatg                                        27

<210> SEQ ID NO 78
<211> LENGTH: 52
<212> TYPE: DNA
<213> ORGANISM: Artificial sequence
<220> FEATURE:
<223> OTHER INFORMATION: 2A10 VH forward primer

<400> SEQUENCE: 78
actcataagc ttgccaccat gggatggagc tgtatcatcc tcttttggt ag             52

<210> SEQ ID NO 79
<211> LENGTH: 30
<212> TYPE: DNA
<213> ORGANISM: Artificial sequence
<220> FEATURE:
<223> OTHER INFORMATION: VH reverse primer

<400> SEQUENCE: 79
actatgacta gtgtgccttg gccccagtag                                     30

<210> SEQ ID NO 80
<211> LENGTH: 42
<212> TYPE: DNA
```

```
<213> ORGANISM: Artificial sequence
<220> FEATURE:
<223> OTHER INFORMATION: VL forward primer

<400> SEQUENCE: 80
actcataagc ttgccaccat gaggtgctct cttcagtttc tg                         42

<210> SEQ ID NO 81
<211> LENGTH: 29
<212> TYPE: DNA
<213> ORGANISM: Artificial sequence
<220> FEATURE:
<223> OTHER INFORMATION: VL reverse primer

<400> SEQUENCE: 81
actatgcgta cgtttcagct ccagcttgg                                        29

<210> SEQ ID NO 82
<211> LENGTH: 19
<212> TYPE: PRT
<213> ORGANISM: Artificial sequence
<220> FEATURE:
<223> OTHER INFORMATION: CAMPATH-1H signal sequence

<400> SEQUENCE: 82

Met Gly Trp Ser Cys Ile Ile Leu Phe Leu Val Ala Thr Ala Thr Gly
1               5                   10                  15

Val His Ser

<210> SEQ ID NO 83
<211> LENGTH: 120
<212> TYPE: PRT
<213> ORGANISM: Homo sapiens

<400> SEQUENCE: 83

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gln Trp Leu Val Ile Leu Asn Phe Asp Tyr Trp Gly Gln
            100                 105                 110

Gly Thr Leu Val Thr Val Ser Ser
        115                 120

<210> SEQ ID NO 84
<211> LENGTH: 113
<212> TYPE: PRT
<213> ORGANISM: Artificial sequence
<220> FEATURE:
<223> OTHER INFORMATION: Humanised VH construct H1

<400> SEQUENCE: 84

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Asn Ile Asn Pro Ser Asn Gly Gly Thr Asn Tyr Asn Glu Lys Phe
50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Glu Leu Gly Gln Gly Tyr Trp Gly Gln Gly Thr Thr Val Thr Val Ser
            100                 105                 110

Ser

<210> SEQ ID NO 85
<211> LENGTH: 112
<212> TYPE: PRT
<213> ORGANISM: Homo sapiens

<400> SEQUENCE: 85

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Gly Leu Val Tyr Ser
            20                  25                  30

Asp Gly Asp Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
50                  55                  60

Asp Arg Phe Ser Gly Gly Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gly Gly Thr Lys Leu Glu Ile Lys
            100                 105                 110

<210> SEQ ID NO 86
<211> LENGTH: 112
<212> TYPE: PRT
<213> ORGANISM: Artificial sequence
<220> FEATURE:
<223> OTHER INFORMATION: Humanised VL construct L11

<400> SEQUENCE: 86

Asp Ile Val Ile Thr Gln Ser Pro Leu Ser Leu Pro Val Thr Leu Gly
1               5                   10                  15

Gln Pro Ala Ser Ile Ser Cys Arg Ser Ser Lys Ser Leu Leu Tyr Lys
            20                  25                  30

Asp Gly Lys Thr Tyr Leu Asn Trp Phe Gln Gln Arg Pro Gly Gln Ser
        35                  40                  45

Pro Gln Leu Leu Ile Tyr Leu Met Ser Thr Arg Ala Ser Gly Val Pro
50                  55                  60

Asp Arg Phe Ser Gly Gly Gly Ser Gly Thr Asp Phe Thr Leu Lys Ile
65                  70                  75                  80

Ser Arg Val Glu Ala Glu Asp Val Gly Val Tyr Tyr Cys Gln Gln Leu
                85                  90                  95

Val Glu Tyr Pro Leu Thr Phe Gly Gln Gly Thr Lys Leu Glu Ile Lys
            100                 105                 110
```

```
<210> SEQ ID NO 87
<211> LENGTH: 201
<212> TYPE: PRT
<213> ORGANISM: Homo sapiens

<400> SEQUENCE: 87

Met Gln Glu Ser Leu Tyr Pro Ala Ala Gln Leu Cys Pro Ser Phe Glu
1               5                   10                  15

Glu Ser Glu Ala Thr Pro Ser Pro Val Leu Pro Asp Ile Val Met Glu
                20                  25                  30

Ala Pro Leu Asn Ser Ala Val Pro Ser Ala Gly Ala Ser Val Ile Gln
                35                  40                  45

Pro Ser Ser Ser Pro Leu Glu Ala Ser Val Asn Tyr Glu Ser Ile
        50                  55                  60

Lys His Glu Pro Glu Asn Pro Pro Tyr Glu Ala Met Ser Val
65                  70                  75                  80

Ser Leu Lys Lys Val Ser Gly Ile Lys Glu Ile Lys Glu Pro Glu
                85                  90                  95

Asn Ile Asn Ala Ala Leu Gln Glu Thr Glu Ala Pro Tyr Ile Ser Ile
                100                 105                 110

Ala Cys Asp Leu Ile Lys Glu Thr Lys Leu Ser Ala Glu Pro Ala Pro
                115                 120                 125

Asp Phe Ser Asp Tyr Ser Glu Met Ala Lys Val Glu Gln Pro Val Pro
                130                 135                 140

Asp His Ser Glu Leu Val Glu Asp Ser Ser Pro Asp Ser Glu Pro Val
145                 150                 155                 160

Asp Leu Phe Ser Asp Asp Ser Ile Pro Asp Val Pro Gln Lys Gln Asp
                165                 170                 175

Glu Thr Val Met Leu Val Lys Glu Ser Leu Thr Glu Thr Ser Phe Glu
                180                 185                 190

Ser Met Ile Glu Tyr Glu Asn Lys Glu
                195                 200

<210> SEQ ID NO 88
<211> LENGTH: 462
<212> TYPE: PRT
<213> ORGANISM: Artificial sequence
<220> FEATURE:
<223> OTHER INFORMATION: anti-NOGO antibody heavy chain

<400> SEQUENCE: 88

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
                35                  40                  45

Thr Ser Tyr Trp Met His Trp Val Arg Gln Ala Pro Gly Gln Gly Leu
        50                  55                  60

Glu Trp Met Gly Asn Ile Asn Pro Ser Asn Gly Gly Thr Asn Tyr Asn
65                  70                  75                  80

Glu Lys Phe Lys Ser Arg Val Thr Met Thr Arg Asp Thr Ser Thr Ser
                85                  90                  95

Thr Val Tyr Met Glu Leu Ser Ser Leu Arg Ser Glu Asp Thr Ala Val
                100                 105                 110

Tyr Tyr Cys Glu Leu Gly Gln Gly Tyr Trp Gly Gln Gly Thr Leu Val
                115                 120                 125
```

Thr Val Ser Ser Ala Ser Thr Lys Gly Pro Ser Val Phe Pro Leu Ala
            130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 89
<211> LENGTH: 238
<212> TYPE: PRT
<213> ORGANISM: Artificial sequence
<220> FEATURE:
<223> OTHER INFORMATION: anti-NOGO antibody light chain

<400> SEQUENCE: 89

Met Gly Trp Ser Cys Ile Ile Leu Phe Leu Val Ala Thr Ala Thr Gly
1               5                   10                  15

Val His Ser Asp Ile Val Ile Thr Gln Ser Pro Leu Ser Leu Pro Val
            20                  25                  30

```
Thr Leu Gly Gln Pro Ala Ser Ile Ser Cys Arg Ser Ser Lys Ser Leu
         35                  40                  45

Leu Tyr Lys Asp Gly Lys Thr Tyr Leu Asn Trp Phe Gln Gln Arg Pro
 50                  55                  60

Gly Gln Ser Pro Gln Leu Leu Ile Tyr Leu Met Ser Thr Arg Ala Ser
 65                  70                  75                  80

Gly Val Pro Asp Arg Phe Ser Gly Gly Ser Gly Thr Asp Phe Thr
                 85                  90                  95

Leu Lys Ile Ser Arg Val Glu Ala Glu Asp Val Gly Val Tyr Tyr Cys
                100                 105                 110

Gln Gln Leu Val Glu Tyr Pro Leu Thr Phe Gly Gln Gly Thr Lys Leu
            115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 90
<211> LENGTH: 1428
<212> TYPE: DNA
<213> ORGANISM: Artificial sequence
<220> FEATURE:
<223> OTHER INFORMATION: Polynucleotide encoding SEQ ID NO: 88

<400> SEQUENCE: 90
aagctttaca gttactcagc acacaggacc tcaccatggg atggagctgt atcatcctct      60
tcttggtagc aacagctaca ggtgtccact cccaggtgca gctggtgcag tctggggctg     120
aggtgaagaa gcctggggcc tcagtgaagg tttcctgcaa ggcatctgga tacaccttca     180
ccagctactg gatgcactgg gtgcgacagg cccctggaca agggcttgag tggatgggaa     240
atattaatcc tagcaatggt ggtactaact acaatgagaa gttcaagagc agagtcacca     300
tgaccaggga cacgtccacg agcacagtct acatggagct gagcagcctg agatctgagg     360
acacggccgt gtattactgt gaactgggac agggctactg gggccaggga acactagtca     420
cagtctcctc agcctccacc aagggcccat cggtcttccc cctggcaccc tcctccaaga     480
gcacctctgg gggcacagcg gccctgggct gcctggtcaa ggactacttc cccgaaccgg     540
tgacggtgtc gtggaactca ggcgccctga ccagcggcgt gcacaccttc ccggctgtcc     600
tacagtcctc aggactctac tccctcagca gcgtggtgac cgtgccctcc agcagcttgg     660
gcacccagac ctacatctgc aacgtgaatc acaagcccag caacaccaag gtggacaaga     720
aagttgagcc caaatcttgt gacaaaactc acacatgccc accgtgccca gcacctgaac     780
tcgcggggca ccgtcagtc ttcctcttcc ccccaaaacc caaggacacc ctcatgatct     840
cccggacccc tgaggtcaca tgcgtggtgg tggacgtgag ccacgaagac cctgaggtca     900
agttcaactg gtacgtggac ggcgtggagg tgcataatgc caagacaaag ccgcgggagg     960
```

-continued

```
agcagtacaa cagcacgtac cgtgtggtca gcgtcctcac cgtcctgcac caggactggc    1020
tgaatggcaa ggagtacaag tgcaaggtct ccaacaaagc cctcccagcc cccatcgaga    1080
aaaccatctc caaagccaaa gggcagcccc gagaaccaca ggtgtacacc ctgcccccat    1140
cccgggatga gctgaccaag aaccaggtca gcctgacctg cctggtcaaa ggcttctatc    1200
ccagcgacat cgccgtggag tgggagagca atgggcagcc ggagaacaac tacaagacca    1260
cgcctcccgt gctggactcc gacggctcct tcttcctcta cagcaagctc accgtggaca    1320
agagcaggtg gcagcagggg aacgtcttct catgctccgt gatgcatgag gctctgcaca    1380
accactacac gcagaagagc ctctccctgt ctccgggtaa atgaattc              1428
```

<210> SEQ ID NO 91
<211> LENGTH: 758
<212> TYPE: DNA
<213> ORGANISM: Artificial sequence
<220> FEATURE:
<223> OTHER INFORMATION: Polynucleotide encoding SEQ ID NO: 89

<400> SEQUENCE: 91

```
aagctttaca gttactcagc acacaggacc tcaccatggg atggagctgt atcatcctct     60
tcttggtagc aacagctaca ggtgtccact ccgatattgt gataacccag tctccactct    120
ccctgcccgt caccottgga cagccggcct ccatctcctg caggtctagt aagagtctcc    180
tatataagga tgggaagaca tacttgaatt ggtttcagca gaggccaggc caatctccac    240
agctcctaat ttatttgatg tccacccgtg catctggggt cccagacaga ttcagcggcg    300
gtgggtcagg cactgatttc acactgaaaa tcagcagggt ggaggctgag gatgttgggg    360
tttattactg ccaacaactt gtagagtatc cgctcacgtt tggccagggg accaagctgg    420
agatcaaacg tacggtggct gcaccatctg tcttcatctt cccgccatct gatgagcagt    480
tgaaatctgg aactgcctct gttgtgtgcc tgctgaataa cttctatccc agagaggcca    540
aagtacagtg gaaggtggac aacgccctcc aatcgggtaa ctcccaggag agtgtcacag    600
agcaggacag caaggacagc acctacagcc tcagcagcac cctgacgctg agcaaagcag    660
actacgagaa acacaaagtc tacgcctgcg aagtcaccca tcagggcctg agctcgcccg    720
tcacaaagag cttcaacagg ggagagtgtt aggaattc                            758
```

<210> SEQ ID NO 92
<211> LENGTH: 462
<212> TYPE: PRT
<213> ORGANISM: Artificial sequence
<220> FEATURE:
<223> OTHER INFORMATION: Heavy chain sequence for HcLc

<400> SEQUENCE: 92

```
Met Gly Trp Ser Cys Ile Ile Leu Phe Leu Val Ala Ala Ala Thr Gly
1               5                   10                  15

Val His Ser Gln Val Gln Leu Gln Gln Pro Gly Thr Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Asn Ile Asn Pro Ser Asn Gly Gly Thr Asn Tyr Asn
65                  70                  75                  80

Glu Lys Phe Lys Ser Lys Ala Thr Leu Thr Val Asp Lys Ser Ser Ser
                85                  90                  95
```

Thr Ala Tyr Met Gln Leu Ser Ser Leu Thr Ser Glu Asp Ser Ala Val
            100                 105                 110

Tyr Tyr Cys Glu Leu Gly Gln Gly Tyr Trp Gly Gln Gly Thr Leu Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 93
<211> LENGTH: 1405
<212> TYPE: DNA
<213> ORGANISM: Artificial sequence
<220> FEATURE:
<223> OTHER INFORMATION: Polynucleotide encoding SEQ ID NO: 92

<400> SEQUENCE: 93

```
aagcttgcca ccatgggatg gagctgtatc atcctctttt tggtagcagc agctacaggt    60
gtccactccc aggtccaact gcagcagcct gggactgaac tggtgaagcc tggggcttca   120
gtgaagctgt cctgcaaggc ttctggctac accttcacca gctactggat gcactgggtg   180
aagcagaggc ctggacaagg ccttgagtgg attggaaata ttaatcctag caatggtggt   240
actaactaca tgagaagttt caagagcaag gccacactga ctgtagacaa atcctccagc   300
acagcctaca tgcagctcag cagcctgaca tctgaggact ctgcggtcta ttattgtgaa   360
ctgggacagg gctactgggg ccaaggcaca ctagtcacag tctcctcagc tccaccaag    420
ggcccatcgg tcttccccct ggcaccctcc tccaagagca cctctggggg cacagcggcc   480
ctgggctgcc tggtcaagga ctacttcccc gaaccggtga cggtgtcgtg aactcaggc    540
gccctgacca cggcgtgca caccttcccg gctgtcctac agtcctcagg actctactcc    600
ctcagcagcg tggtgaccgt gccctccagc agcttgggca cccagaccta catctgcaac   660
gtgaatcaca agcccagcaa caccaaggtg gacaagaaag ttgagcccaa atcttgtgac   720
aaaactcaca catgcccacc gtgcccagca cctgaactcc tggggggacc gtcagtcttc   780
ctcttccccc caaaacccaa ggacaccctc atgatctccc ggacccctga ggtcacatgc   840
gtggtggtgg acgtgagcca cgaagaccct gaggtcaagt tcaactggta cgtggacggc   900
gtggaggtgc ataatgccaa gacaaagccg cgggaggagc agtacaacag cacgtaccgt   960
gtggtcagcg tcctcaccgt cctgcaccag gactggctga atggcaagga gtacaagtgc  1020
aaggtctcca acaaagccct cccagccccc atcgagaaaa ccatctccaa agccaaaggg  1080
cagccccgag aaccacaggt gtacaccctg cccccatccc gggatgagct gaccaagaac  1140
caggtcagcc tgacctgcct ggtcaaaggc ttctatccca gcgacatcgc cgtggagtgg  1200
gagagcaatg ggcagccgga gaacaactac aagaccacgc ctcccgtgct ggactccgac  1260
ggctccttct tcctctacag caagctcacc gtggacaaga gcaggtggca gcaggggaac  1320
gtcttctcat gctccgtgat gcatgaggct ctgcacaacc actacacgca gaagagcctc  1380
tccctgtctc cgggtaaatg aattc                                         1405
```

<210> SEQ ID NO 94
<211> LENGTH: 239
<212> TYPE: PRT
<213> ORGANISM: Artificial sequence
<220> FEATURE:
<223> OTHER INFORMATION: Light chain sequence for HcLc

<400> SEQUENCE: 94

Met Arg Cys Ser Leu Gln Phe Leu Gly Val Leu Met Phe Trp Ile Ser
1               5                   10                  15

Gly Val Ser Gly Asp Ile Val Ile Thr Gln Asp Glu Leu Ser Asn Pro
            20                  25                  30

Val Thr Ser Gly Glu Ser Val Ser Ile Ser Cys Arg Ser Ser Lys Ser
        35                  40                  45

Leu Leu Tyr Lys Asp Gly Lys Thr Tyr Leu Asn Trp Phe Leu Gln Arg
    50                  55                  60

Pro Gly Gln Ser Pro Gln Leu Leu Ile Tyr Leu Met Ser Thr Arg Ala
65                  70                  75                  80

Ser Gly Val Ser Asp Arg Phe Ser Gly Ser Gly Ser Gly Thr Asp Phe
                85                  90                  95

Thr Leu Glu Ile Ser Arg Val Lys Ala Glu Asp Val Gly Val Tyr Tyr
            100                 105                 110

Cys Gln Gln Leu Val Glu Tyr Pro Leu Thr Phe Gly Ala Gly Thr Lys 115                 120                 125
Leu Glu Leu Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 95
<211> LENGTH: 738
<212> TYPE: DNA
<213> ORGANISM: Artificial sequence
<220> FEATURE:
<223> OTHER INFORMATION: Polynucleotide encoding SEQ ID NO: 94

<400> SEQUENCE: 95
aagcttgcca ccatgaggtg ctctcttcag tttctggggg tgcttatgtt ctggatctct    60
ggagtcagtg gggatattgt gataaccag gatgaactct ccaatcctgt cacttctgga   120
gaatcagttt ccatctcctg caggtctagt aagagtctcc tatataagga tgggaagaca   180
tacttgaatt ggtttctgca gagaccagga caatctcctc agctcctgat ctatttgatg   240
tccacccgtg catcaggagt ctcagaccgg tttagtggca gtgggtcagg aacagatttc   300
accctggaaa tcagtagagt gaaggctgag gatgtgggtg tgtattactg tcaacaactt   360
gtagagtatc cgctcacgtt cggtgctggg accaagctgg agctgaaacg tacggtggct   420
gcaccatctg tcttcatctt cccgccatct gatgagcagt tgaaatctgg aactgcctct   480
gttgtgtgcc tgctgaataa cttctatccc agagaggcca agtacagtg gaaggtggac   540
aacgccctcc aatcgggtaa ctcccaggag agtgtcacag agcaggacag caaggacagc   600
acctacagcc tcagcagcac cctgacgctg agcaaagcag actacgagaa acacaaagtc   660
tacgcctgcg aagtcaccca tcagggcctg agctcgcccg tcacaaagag cttcaacagg   720
ggagagtgtt aggaattc                                                   738

<210> SEQ ID NO 96
<211> LENGTH: 4
<212> TYPE: PRT
<213> ORGANISM: Artificial sequence
<220> FEATURE:
<223> OTHER INFORMATION: Motif

<400> SEQUENCE: 96

Tyr Glu Asn Pro
1

<210> SEQ ID NO 97
<211> LENGTH: 4
<212> TYPE: PRT
<213> ORGANISM: Artificial sequence
<220> FEATURE:
<223> OTHER INFORMATION: Motif

```
<400> SEQUENCE: 97

Lys Lys Gln Asn
1
```

NOGO-A NEUTRALISING IMMUNOGLOBULIN FOR TREATMENT OF NEUROLOGICAL DISEASES

FIELD OF THE INVENTION

The present invention relates to immunoglobulins, particularly antibodies that bind to NOGO and neutralise the activity thereof, polynucleotides encoding such antibodies, pharmaceutical formulations containing said antibodies and to the use of such antibodies in the treatment and/or prophylaxis of neurological diseases. Other aspects, objects and advantages of the present invention will become apparent from the description below.

BACKGROUND OF THE INVENTION

Stroke is a major cause of death and disability in the Western World. There is no approved therapy for the treatment of stroke other than tissue plasminogen (t-PA) which has to be administered within 3 hours of onset following a computer tomography (CT) scan to exclude haemorrhage. To date most therapeutic agents directed towards the treatment of acute stroke (i.e. neuroprotection), have predominantly involved targeting glutamate receptors and their down stream signalling pathways known to be involved in acute cell death. However to date these strategies have proved unsuccessful in clinical trials and are often associated with dose-limiting side effects (Hill & Hachinski, The Lancet, 352 : (suppl III) 10-14 (1998)). Therefore there is a need for novel approaches directed towards the amelioration of cell death following the cessation of blood flow. Neuroprotection is the ability of a treatment to prevent or ameliorate neuronal cell toss in response to an insult or disease process. This maybe achieved by targeting the neurons directly or indirectly by preventing glial (including oligodendrocyte) cell loss.

Following the onset of stroke, some degree of spontaneous functional recovery is observed in many patients, suggesting that the brain has the (albeit limited) ability to repair and/or remodel following injury. Agents that have the potential to enhance this recovery may therefore allow intervention to be made much later (potentially days) following the onset of cerebral ischaemia. Agents which are able to offer both acute neuroprotection and enhance functional recovery may provide significant advantages over current potential neuroprotective strategies.

Alzheimer's disease (AD) is characterised by the presence of two diagnostic features of pathology. These are amyloid plaques and neurofibrillary tangles composed of aggregated beta-amyloid peptide (A$\beta$40 and A$\beta$42) and hyperphosphorylated tau respectively (Dawbarn & Allen 2001 Neurobiology of Alzheimer's Disease OUP).

A comprehensive study has shown a strong link in patients between beta-amyloid accumulation and cognitive decline (Naslund et al, JAMA, Mar. 22/29, 2000, Vol. 283, No; 12, page 1571-1577). This is consistent with genetic and epidemiological studies that suggest that some mutations in APP and presenilin genes can predispose to early onset AD, which mutations also enhance the levels of A$\beta$40 and A$\beta$42 peptide, including the ratio thereof.

Cleavage of the type I transmembrane amyloid precursor protein (APP) by two distinct proteases designated beta- and gamma-secretase is necessary for the formation of beta-amyloid peptide. The molecular identity of beta-secretase as the aspartyl-protease Asp2/BACE1 has been confirmed (Hussain et al Mol. Cell. NeuroSci. 16, 609-619 (2000); Vassar et al, Science (1999), October 22; 286 (5440):735-741). The nature of gamma-secretase remains the source of some debate and is likely to consist of a high molecular weight complex consisting of at least, the following proteins: presenilins, Aph1, Pen2 and nicastrin (reviewed in Medina & Dotti Cell Signalling 2003 15(9):829-41).

The processing of APP within the CNS is likely to occur within a number of cell-types including neurons, oligodendrocytes, astrocytes and microglia. While the overall rate of APP processing in these cells will be influenced by the relative level of expression of APP, BACE1/Asp2, presenilin-1 and -2, Aph1, Pen2 and nicastrin.

Furthermore, additional factors regulating the subcellular location of APP can also influence its processing as shown by the finding that mutation of the YENP motif in the APP cytoplasmic domain which blocks its endocytosis reduces beta-amyloid production (Perez et al 1999 J Biol Chem 274 (27) 18851-6). Retention of the APP-beta-CTF in the ER by the addition of the KKQN retention motif is sufficient to reduce amyloid production in transfected cells (Maltese et al 2001 J Biol Chem 276 (23) 20267-20279). Conversely, elevation of endocytosis, by overexpression of Rab5 is sufficient to elevate amyloid secretion from transfected cells (Grbovic et al 2003 J Biol Chem 278 (33) 31261-31268).

Consistent with these findings further studies have shown that reduction of cellular cholesterol levels (a well known risk factor for AD) reduced beta-amyloid formation. This change was dependent on altered endocytosis as demonstrated by the use of the dominant negative dynamin mutants (K44A) and overexpression of the Rab5 GTPase activating protein RN-Tre (Ehehalt et al 2003 J Cell Biol 160 (1) 113-123).

Cholesterol rich microdomains or rafts are also an important cellular site of beta-amyloid production and APP, BACE1 and components of the gamma-secretase complex have all been shown to transiently reside within rafts. Antibody cross-linking of APP and BACE1 towards cholesterol rich rafts was able to elevate beta-amyloid production (Ehehalt et al 2003 J Cell Biol 160 (1) 113-123). Expression of GPI-anchored BACE1, which is exclusively targeted to lipid rafts, is similarly able to elevate APP cleavage and beta-amyloid production (Cordy et al 2003 PNAS 100(20) 11735-11740).

The mechanisms underlying functional recovery are currently unknown. The sprouting of injured or non-injured axons has been proposed as one possible mechanism. However, although in vivo studies have shown that treatment of spinal cord injury or stroke with neurotrophic factors results in enhanced functional recovery and a degree of axonal sprouting, these do not prove a direct link between the degree of axonal sprouting and extent of functional recovery (Jakeman, et al. 1998, Exp. Neurol. 154: 170-184, Kawamata et al. 1997, Proc Natl Acad. Sci. USA., 94:8179-8184, Ribotta, et al. 2000, J Neurosci. 20: 5144-5152). Furthermore, axonal sprouting requires a viable neuron. In diseases such as stroke which is associated with extensive cell death, enhancement of functional recovery offered by a given agent post stroke may therefore be through mechanisms other than axonal sprouting such as differentiation of endogenous stem cells, activation of redundant pathways, changes in receptor distribution or excitability of neurons or glia (Fawcett & Asher, 1999, Brain Res. Bulletin, 49: 377-391, Horner & Gage, 2000, Nature 407 963-970).

The limited ability of the central nervous system (CNS) to repair following injury is thought in part to be due to molecules within the CNS environment that have an inhibitory effect on axonal sprouting (neurite outgrowth). CNS myelin is thought to contain inhibitory molecules (Schwab M E and Caroni P (1988) J. Neurosci. 8, 2381-2193). Two myelin proteins, myelin-associated glycoprotein (MAG) and NOGO have been cloned and identified as putative inhibitors of neurite outgrowth (Sato S. et al (1989) Biochem. Biophys. Res. Comm. 163,1473-1480; McKerracher L et al (1994) Neuron 13, 805-811; Mukhopadhyay G et al (1994) Neuron 13, 757-767; Torigoe K and Lundborg G (1997) Exp. Neurology 150, 254-262; Schafer et al (1996) Neuron 16, 1107-1113; WO9522344; WO9701352; Prinjha R et al (2000) Nature 403, 383-384; Chen M S et al (2000) Nature 403, 434-439; GrandPre T et al (2000) Nature 403, 439444; US005250414A1; WO200005364A1; WO0031235).

Three forms of human NOGO have been identified: NOGO-A having 1192 amino acid residues (GenBank accession no. AJ251383); NOGO-B, a splice variant which lacks residues 186 to 1004 in the putative extracellular domain (GenBank accession no. AJ251384) and a shorter splice variant, NOGO-C, which also lacks residues 186 to 1004 and also has smaller, alternative amino terminal domain (GenBank accession no. AJ251385) (Prinjha et al (2000) supra).

Inhibition of the CNS inhibitory proteins such as NOGO may provide a therapeutic means to ameliorate neuronal damage and promote neuronal repair and growth thereby potentially assisting recovery from neuronal injury such as that sustained in stroke. Examples of such NOGO inhibitors may include small molecules, peptides and antibodies.

Antibodies typically comprise two heavy chains linked together by disulphide bonds and two light chains. Each light chain is linked to a respective heavy chain by disulphide bonds. Each heavy chain has at one end a variable domain followed by a number of constant domains. Each light chain has a variable domain at one end and a constant domain at its other end. The light chain variable domain is aligned with the variable domain of the heavy chain. The light chain constant domain is aligned with the first constant domain of the heavy chain. The constant domains in the light and heavy chains are not involved directly in binding the antibody to antigen.

The variable domains of each pair of light and heavy chains form the antigen binding site. The variable domains on the light and heavy chains have the same general structure and each domain comprises a framework of four regions, whose sequences are relatively conserved, connected by three complementarity determining regions (CDRs) often referred to as hypervariable regions. The four framework regions largely adopt a beta-sheet conformation and the CDRs form loops connecting, and in some cases, forming part of, the beta-sheet structure. The CDRs are held in close proximity by the framework regions and, with the CDRs from the other domain, contribute to the formation of the antigen binding site. CDRs and framework regions of antibodies may be determined by reference to Kabat et al ("Sequences of proteins of immunological interest" US Dept. of Health and Human Services, US Government Printing Office, 1987).

It has been found that anti-MAG monoclonal antibodies, described (Poltorak et al (1987) Journal of Cell Biology 105, 1893-1899, DeBellard et al (1996) Mol. Cell. Neurosci. 7, 89-101; Tang et al (1997) Mol. Cell. Neurosci. 9, 333-346; Torigoe K and Lundborg G (1997) Exp. Neurology 150, 254-262) and commercially available (MAB1567 (Chemicon)) when administered either directly into the brain or intravenously following focal cerebral ischaemia in the rat (a model of stroke), provides neuroprotection and enhances functional recovery (PCT/EP03/08749).

Therefore anti-MAG antibodies provide potential therapeutic agents for both acute neuroprotection as well as the promotion of functional recovery following stroke. This antibody is a murine antibody. Although murine antibodies are often used as diagnostic agents their utility as a therapeutic has been proven in only a few cases. Their limited application is in part due to the repeated administration of a murine monoclonal antibody to a human usually elicits human immune responses against these molecules. To overcome these intrinsic undesirable properties of murine antibodies, "altered" antibodies designed to incorporate regions of human antibodies have been developed and are well established in the art. For example, a humanised antibody contains complementarity determining regions ("CDR's") of non human origin and the majority of the rest of the structure is derived from a human antibody.

It has also been reported that a murine monoclonal antibody, IN-1, that was raised against NI-220/250, a myelin protein which is a potent inhibitor of neurite growth (and subsequently shown to be fragment of NOGO-A), promotes axonal regeneration (Caroni, P and Schwab, M E (1 988) Neuron 1 85-96; Schnell, L and Schwab, M E (1 990) Nature 343 269-272; Bregman, B S et al (1995) Nature 378 498-501 and Thallmair, M et al (1 998) Nature Neuroscience 1 124-131). It has also been reported that NOGO-A is the antigen for IN-1 (Chen et al (2000) Nature 403 434-439). Administration of IN-1 Fab fragment or humanised IN-1 to rats that have undergone spinal cord transection, enhanced recovery (Fiedler, M et al (2002) Protein Eng 15 931-941; Brosamle, C et al (2000) J. Neuroscience 20 8061-8068). However to date there is no evidence in the literature to suggest that IN-1, or its humanised form, can bind and inhibit human NOGO-A, a necessary requirement for a monoclonal antibody to be useful in the therapeutic treatment of NOGO-mediated diseases and disorders such as stroke and neurodegenerative diseases in humans.

Therefore it remains a highly desirable goal to isolate and develop a therapeutically useful monoclonal antibody that binds and inhibits the activity of human NOGO. The process of neurodegeneration underlies many neurological diseases/disorders including, but not limited to, acute diseases such as stroke (ischemic or haemorrhagic), traumatic brain injury and spinal cord injury as well as chronic diseases including Alzheimer's disease, fronto-temporal dementias (tauopathies), peripheral neuropathy, Parkinson's disease, Creutzfeldt-Jakob disease (CJD), Schizophrenia, amyotrophic lateral sclerosis (ALS), multiple sclerosis, Huntington's disease, multiple sclerosis and inclusion body myositis.

Consequently an anti-NOGO monoclonal antibody may be useful in the treatment of these diseases/disorders. Such antibodies for the treatment of the above mentioned disease/disorders are provided by the present invention and described in detail below.

All publications, both journal and patent, disclosed in this present specification are expressly and entirely incorporated herein by reference.

BRIEF SUMMARY OF THE INVENTION

The invention provides an antibody or functional fragment thereof which binds to and neutralises the activity of NOGO, preferably human NOGO, more preferably human NOGO-A (sometimes referred to herein as "anti-NOGO antibody"). Such antibody may, for example, comprise one or more CDR's as shown in the tables 1 to 6 which show the CDRs of three such independently isolated antibodies: 2A10/3, 2C4/1 and 15C3/3. The CDR's are identified as described by Kabat (Kabat et al. (1991 ) "Sequences of proteins of immunological interest"; Fifth Edition; US Department of Health and Human Services; NIH publication No 91-3242). CDRs preferably are as defined by Kabat but following the principles of protein structure and folding as defined by Chothia and Lesk, (Chothia et al., (1989) "Conformations of immunoglobulin hypervariable regions"; Nature 342, p 877-883) it will be appreciated that additional residues may also be considered to be part of the antigen binding region and are thus encompassed by the present invention.

TABLE 1

Antibody 2A10/3 ("2A10") light chain CDRs

| CDR | According to Kabat | |
|---|---|---|
| L1 | RSSKSLLYKDGKTYLN | (SEQ ID NO: 1) |
| L2 | LMSTRAS | (SEQ ID NO: 2) |
| L3 | QQLVEYPLT | (SEQ ID NO: 3) |

TABLE 2

Antibody 2A10/3 heavy chain CDRs

| CDR | According to Kabat | |
|---|---|---|
| H1 | SYWMH | (SEQ ID NO: 4) |
| H2 | NINPSNGGTNYNEKFKS | (SEQ ID NO: 5) |
| H3 | GQGY | (SEQ ID NO: 6) |

TABLE 3

Antibody 2C4/1 ("2C4") light chain CDRs

| CDR | According to Kabat | |
|---|---|---|
| L1 | RSSQSLVHSNGNTYLH | (SEQ ID NO: 7) |
| L2 | KVSNRFS | (SEQ ID NO: 8) |
| L3 | SQSTHVPLT | (SEQ ID NO: 9) |

TABLE 4

Antibody 2C4/1 heavy chain CDRs

| CDR | According to Kabat | |
|---|---|---|
| H1 | FSCYAMS | (SEQ ID NO: 10) |
| H2 | SISDGGSYTYYPDNVKG | (SEQ ID NO: 11) |
| H3 | ELLFDY | (SEQ ID NO: 12) |

TABLE 5

Antibody 15C3/3 ("15C3") light chain CDRs

| CDR | According to Kabat | |
|---|---|---|
| L1 | RSSKSLLHSNGNTYLY | (SEQ ID NO: 13) |
| L2 | RMSNLAS | (SEQ ID NO: 14) |
| L3 | MQHLEYPLT | (SEQ ID NO: 15) |

TABLE 6

Antibody 15C3/3 heavy chain CDRs

| CDR | According to Kabat | |
|---|---|---|
| H1 | SYWMN | (SEQ ID NO: 16) |
| H2 | QIYPGDGDTNYNGKFKG | (SEQ ID NO: 17) |
| H3 | RFDY | (SEQ ID NO: 18) |

In a first aspect, the present invention provides:
(a) An antibody or functional fragment thereof which binds to and neutralises NOGO, particularly human NOGO, more particularly human NOGO-A activity which antibody or functional fragment thereof comprises a heavy chain variable domain which comprises each of the CDR's of table 2, and a light chain variable domain which comprises each of the CDRs from table 1.
(b) An antibody or functional fragment thereof which binds to and neutralises NOGO, particularly human NOGO, more particularly human NOGO-A activity which antibody or functional fragment thereof comprises a heavy chain variable domain which comprises each of the CDR's of table 4 and a light chain variable domain which comprises each of the CDRs of table 3.
(c) An antibody or functional fragment thereof which antibody or functional fragment thereof comprises a heavy chain variable region which comprises each of the CDR's selected of table 6 and a light chain variable domain which comprises each of the CDRs of table 5.

We further provide an anti-NOGO antibody or functional fragment thereof which comprises:
a) a heavy chain variable domain ($V_H$) which comprises in sequence CDRH1, CDRH2 and CDRH3 from table 2, and/or
b) a light chain variable domain ($V_L$) which comprises in sequence CDRL1, CDRL2 and CDRL3 from table 1;
an anti-NOGO antibody or functional fragment thereof which comprises:
a) a heavy chain variable domain ($V_H$) which comprises in sequence CDRH1, CDRH2 and CDRH3 from table 4, and/or
b) a light chain variable domain ($V_L$) which comprises in sequence CDRL1, CDRL2 and CDRL3 from table 3; or
an anti-NOGO antibody or functional fragment thereof which comprises:
a) a heavy chain variable domain ($V_H$) which comprises in sequence CDRH1, CDRH2 and CDRH3 from table 6, and/or
c) a light chain variable domain ($V_L$) which comprises in sequence CDRL1, CDRL2 and CDRL3 from table 5.

The antibody maybe chimeric, fully human, or humanised.

In another aspect, the present invention also relates to an anti-NOGO antibody which binds to the same (or overlapping) epitope on the NOGO polypeptide as an antibody having the heavy and light chain variable regions described above. Preferably the epitope is comprised within the region 586 to 785 (NOGO-A amino acid numbering, Genbank accession number AJ251383), more preferably the epitope is comprised within the region 586 to 685 or 686 to 785. Competitive inhibition assays are used for mapping of the epitopes on an antigen. Thus there is also provided an anti-NOGO antibody which binds to the human NOGO-A between amino acids 586 to 685 or 686 to 785 and neutralises the activity of NOGO-A. Such an antibody may be produced according to the methods set forth below. In a further aspect, there is also provided an anti-NOGO antibody which competitively inhibits the binding of the antibody having the CDRs described supra to NOGO, preferably human NOGO, most preferably human NOGO-A.

More specifically there is provided an antibody, which may be fully human, humanised or chimeric which binds to and neutralises the activity of NOGO, particularly human NOGO, more particularly human NOGO-A which competitively inhibits, at equimolar concentration, the binding to human NOGO-A of an antibody having a heavy chain variable region comprising each of the CDR's of Table 2 and a light chain variable region comprising each of the CDR's of Table 1.

In another embodiment, there is provided an antibody, which may be fully human, humanised or chimeric which binds to and neutralises the activity of NOGO, particularly human NOGO, more particularly human NOGO-A which competitively inhibits the binding to human NOGO-A of an antibody having a heavy chain variable region comprising each of the CDR's of Table 4 and a light chain variable region comprising each of the CDR's of Table 3.

In another embodiment there is provided an antibody, which may be fully human, humanised or chimeric which binds to and neutralises the activity of NOGO, particularly human NOGO, more particularly human NOGO-A which competitively inhibits the binding to human NOGO-A of an antibody having a heavy chain variable region comprising each of the CDR's of Table 6 and a light chain variable region comprising each of the CDR's of Table 5.

In typical embodiments, the competing antibody is of the IgG class, more typically IgG1 or IgG4.

Chimeric Antibodies

Also provided is a chimeric antibody which binds to and neutralises NOGO, preferably human NOGO, more preferably human NOGO-A comprising CDRs such as those disclosed in tables 1 to 6. Preferably the chimeric antibody comprises mouse and human sequences (e.g. mouse variable region and human constant region). Moreover there is provided a chimeric antibody comprising a heavy chain variable region comprising each of the CDR's of Table 2 and a light chain variable region comprising each of the CDRs of Table 1.

There is also provided a chimeric antibody comprising a heavy chain variable region comprising each of the CDR's of Table 4 and a light chain variable region comprising each of the CDRs of Table 3.

There is also provided a chimeric antibody comprising a heavy chain variable region comprising each of the CDR's of Table 6 and a light chain variable region comprising each of the CDRs of Table 5.

In typical embodiments, the competing antibody is of the IgG class, more typically human IgG1 or IgG4, with a κ type human light chain.

Humanised Antibodies

Further, the invention also provides a humanised antibody which binds to and neutralises NOGO, preferably human NOGO, more preferably human NOGO-A.

More specifically there is provided a humanised antibody comprising a heavy chain variable region comprising each of the CDR's of Table 2 and a light chain variable region comprising each of the CDRs of Table 1.

There is also provided a humanised antibody comprising a heavy chain variable region comprising each of the CDR's of Table 4 and a light chain variable region comprising each of the CDRs of Table 3.

There is also provided a humanised antibody comprising a heavy chain variable region comprising each of the CDR's of Table 6 and a light chain variable region comprising each of the CDRs of Table 5.

In typical embodiments, the antibodies of the invention, whether they are chimaeric, humanised or fully human are of the IgG class, more typically human IgG1 or IgG4, with a κ type human light chain.

A further aspect of the invention provides a pharmaceutical composition comprising an anti-NOGO antibody of the present invention or functional fragment thereof together with a pharmaceutically acceptable diluent or carrier.

In a further aspect, the present invention provides a method of treatment or prophylaxis of stroke (particularly ischemic stroke) and other neurological diseases, in particular Alzheimer's disease, in a human which comprises administering to said human in need thereof an effective amount of an anti-NOGO antibody of the invention or functional fragments thereof.

In another aspect, the invention provides the use of an anti-NOGO antibody of the invention or a functional fragment thereof in the preparation of a medicament for treatment or prophylaxis of stroke (particularly ischemic stroke) and other neurological diseases, in particular Alzheimer's disease.

In a further aspect, the present invention provides a method of inhibiting neurodegeneration and/or promoting functional recovery in a human patient afflicted with, or at risk of developing, a stroke (particularly ischemic stroke) or other neurological disease, in particular Alzheimer's disease, which comprises administering to said human in need thereof an effective amount of an anti-NOGO antibody of the invention or a functional fragment thereof.

In a yet further aspect, the invention provides the use of an anti-NOGO antibody of the invention or a functional fragment thereof in, the preparation of a medicament for inhibiting neurodegeneration and/or promoting functional recovery in a human patient afflicted with, or at risk of developing, a stroke and other neurological disease, in particular Alzheimer's disease.

In a further aspect, we provide an antibody or functional fragment thereof which comprises a heavy chain variable domain which comprises one or more CDR's selected from CDRH1, CDRH2 and CDRH3 of table 1, preferably comprising at least CDRH3, and/or a light chain variable domain which comprises one or more CDRs selected from CDRL1, CDRL2 and CDRL3 from table 4; an antibody or functional fragment thereof which comprises a heavy chain variable domain which comprises one or more CDR's selected from CDRH1, CDRH2 and CDRH3 of table 2, preferably comprising at least CDRH3, and/or a light chain variable domain which comprises one or more CDRs selected from CDRL1, CDRL2 and CDRL3 from table 5; or an antibody or functional fragment thereof which comprises a heavy chain variable domain which comprises one or more CDR's selected from CDRH1, CDRH2 and CDRH3 of table 3, preferably comprising at least CDRH3, and/or a light chain variable domain which comprises one or more CDRs selected from CDRL1, CDRL2 and CDRL3 from table 6.

Other aspects and advantages of the present invention are described further in the detailed description and the preferred embodiments thereof.

For FIGS. 1 to 7 the negative control is the GST protein alone.

Figure 8:
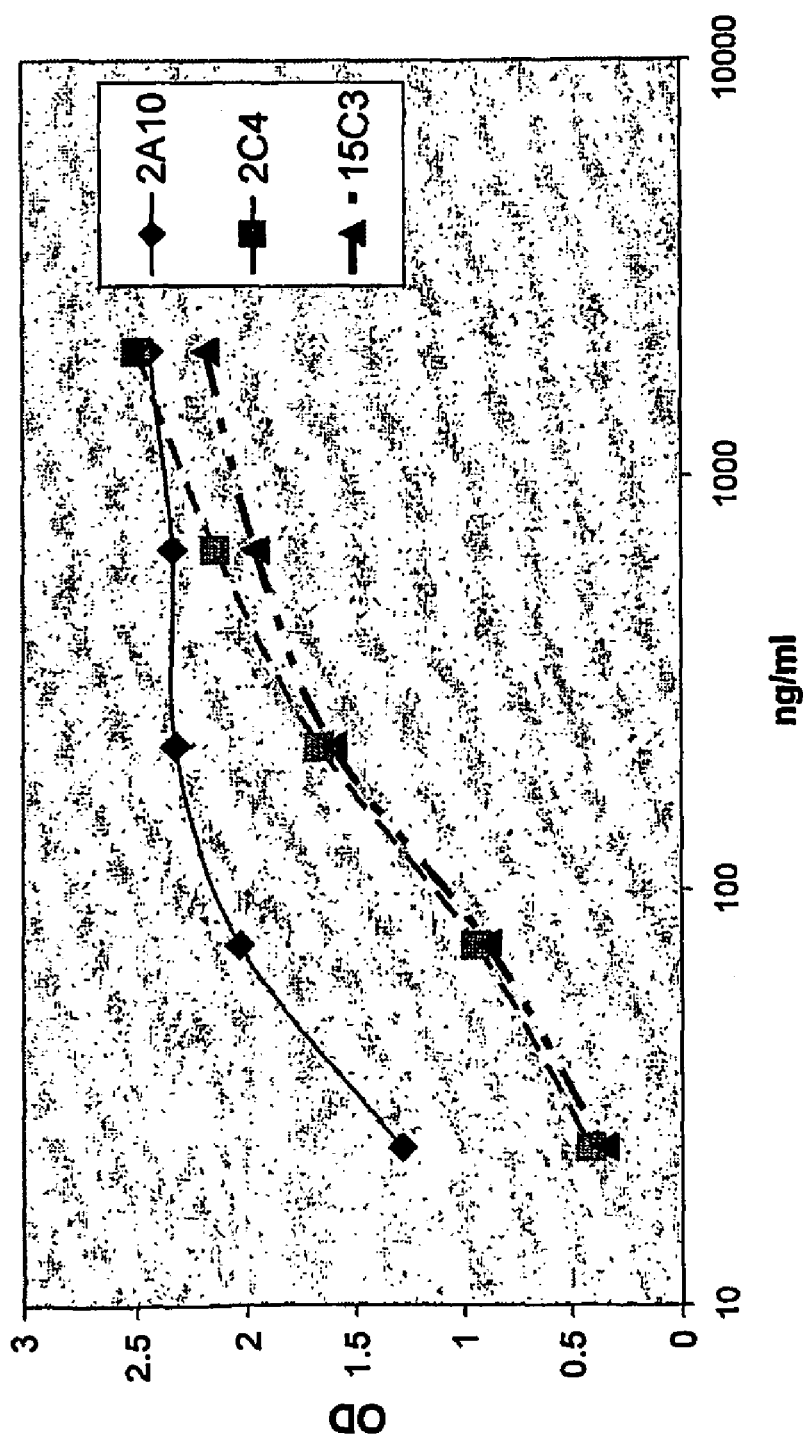

FIG. 8 shows the binding of 2A10, 2C4 and 15C3 monoclonal antibodies to human NOGO-A56. The Y-axis shows the measured OD at 450 nm, a quantitative measure of antibody captured in the wells. The X-axis shows the concentration of antibody used (ng/ml) per well at each data point.

Figure 9:
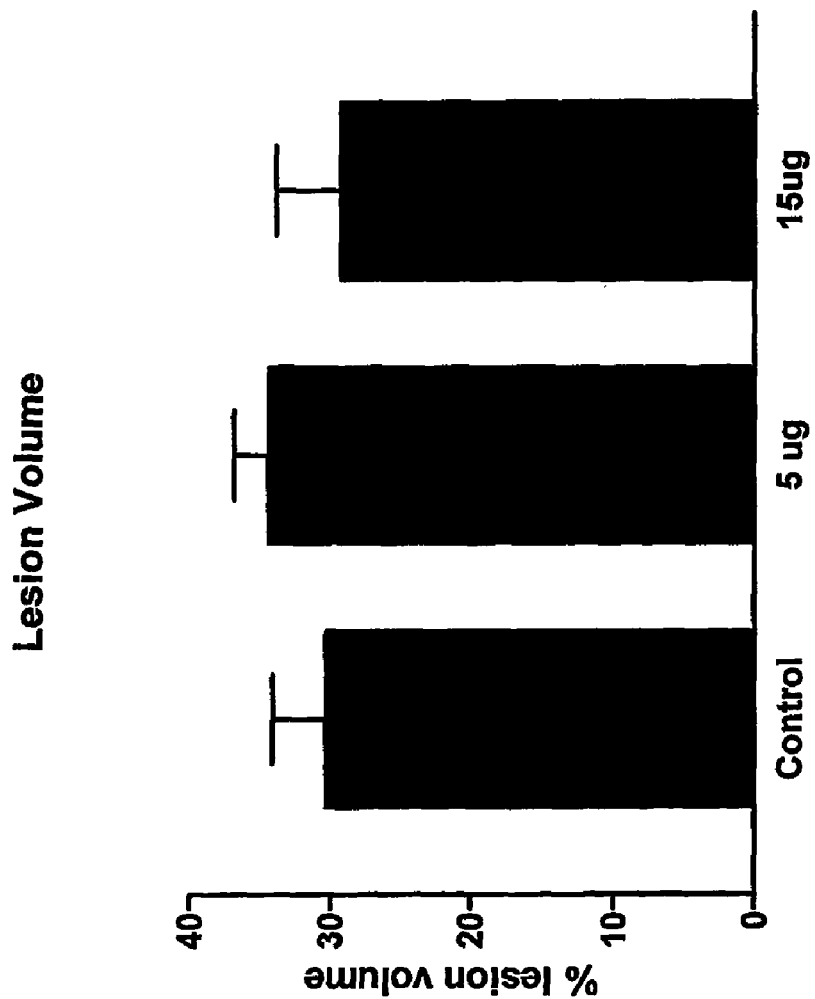

FIG. 9 shows the lesion volume as a percentage of total brain volume at various concentrations following the study of example 10.

Figure 10:
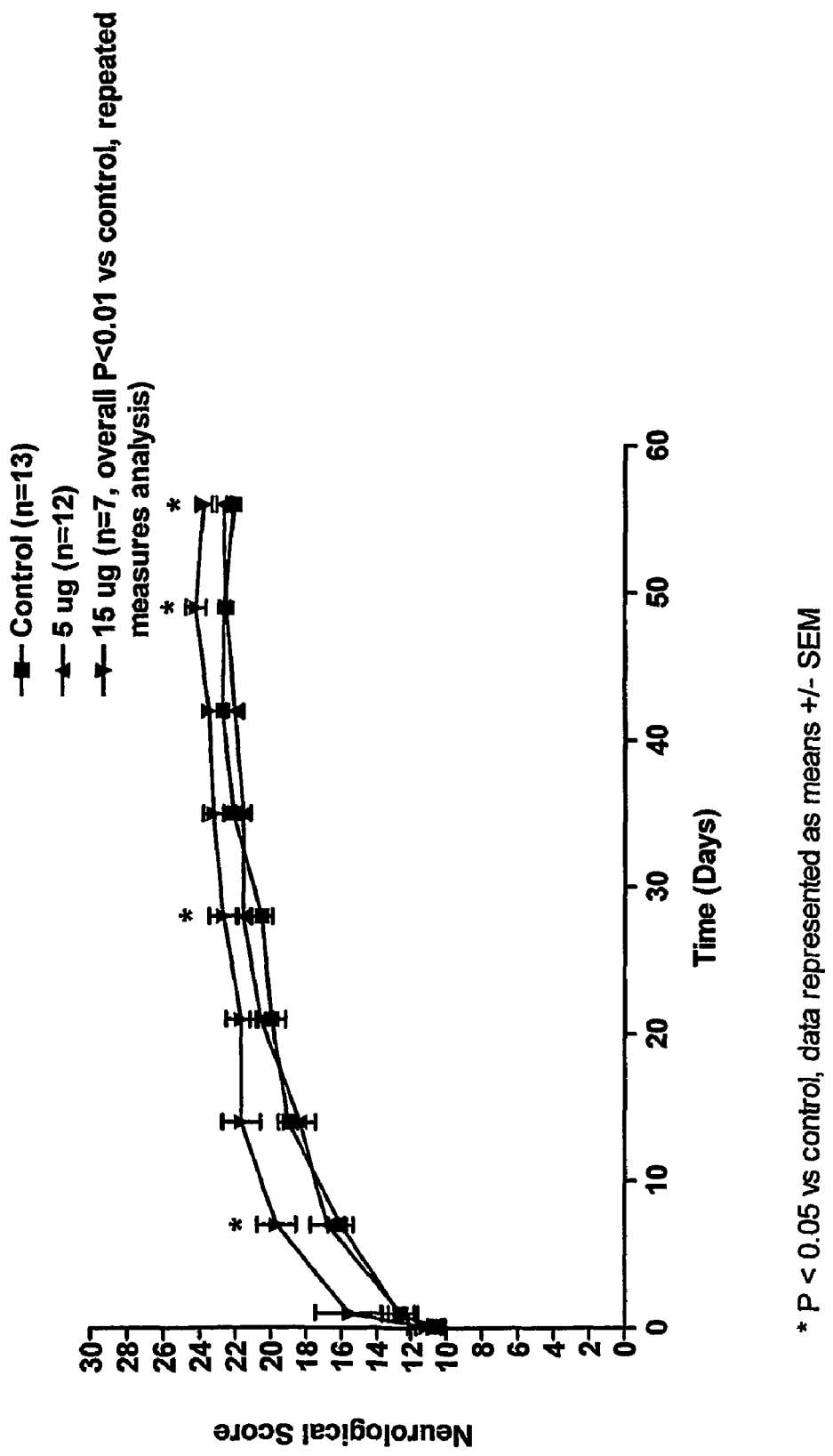

FIG. 10 shows neuroscore data of example 10 represented as means±SEM.

FIGS. 11A, 11B, 11C, 11D. Cylinder data of example 10 represented as mean±SEM for A) both paws, B) left paw, C) right paw and D) right paw split into rats that received 3 doses of 15 μg of anti-NOGO antibody, and those which received 4 doses of anti-NOGO antibody.

Figure 12:
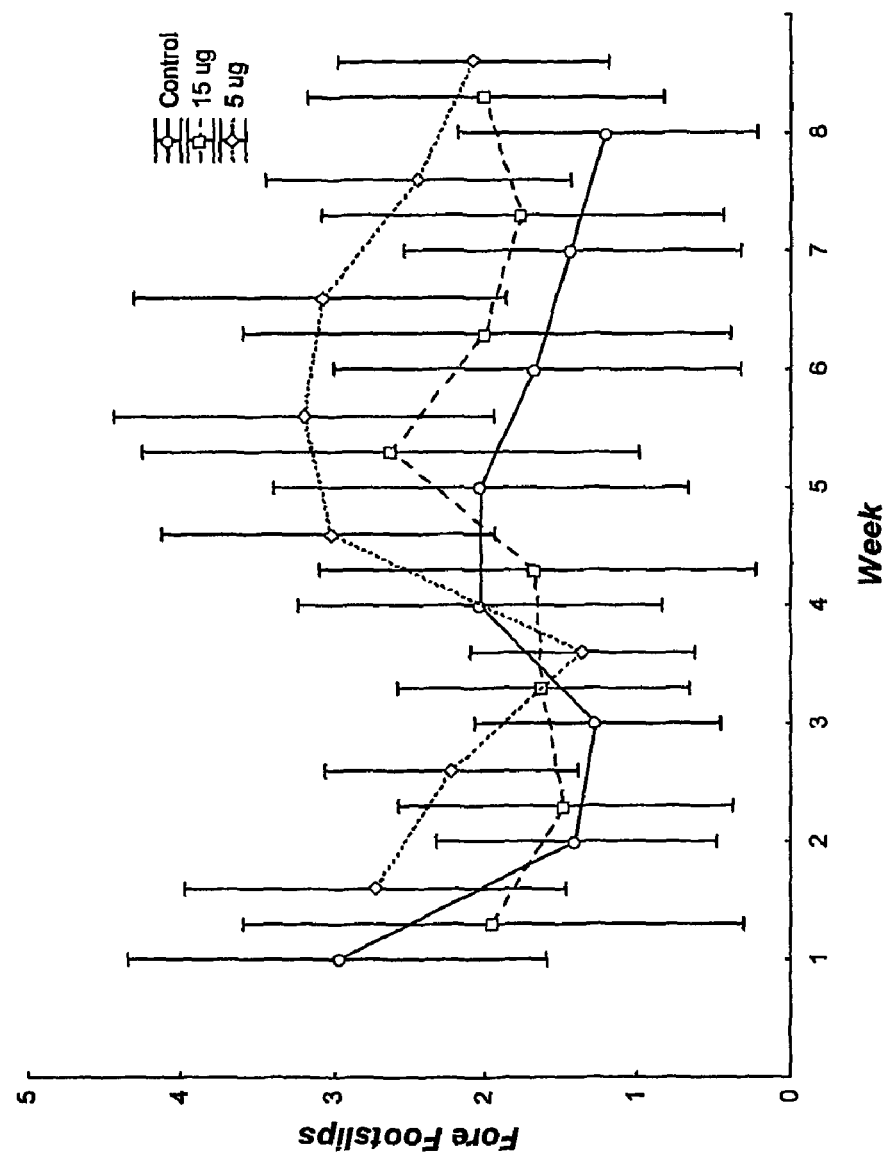

FIG. 12 shows forelimb foot slips of example 10 represented as mean±95% confidence intervals.

Figure 13:
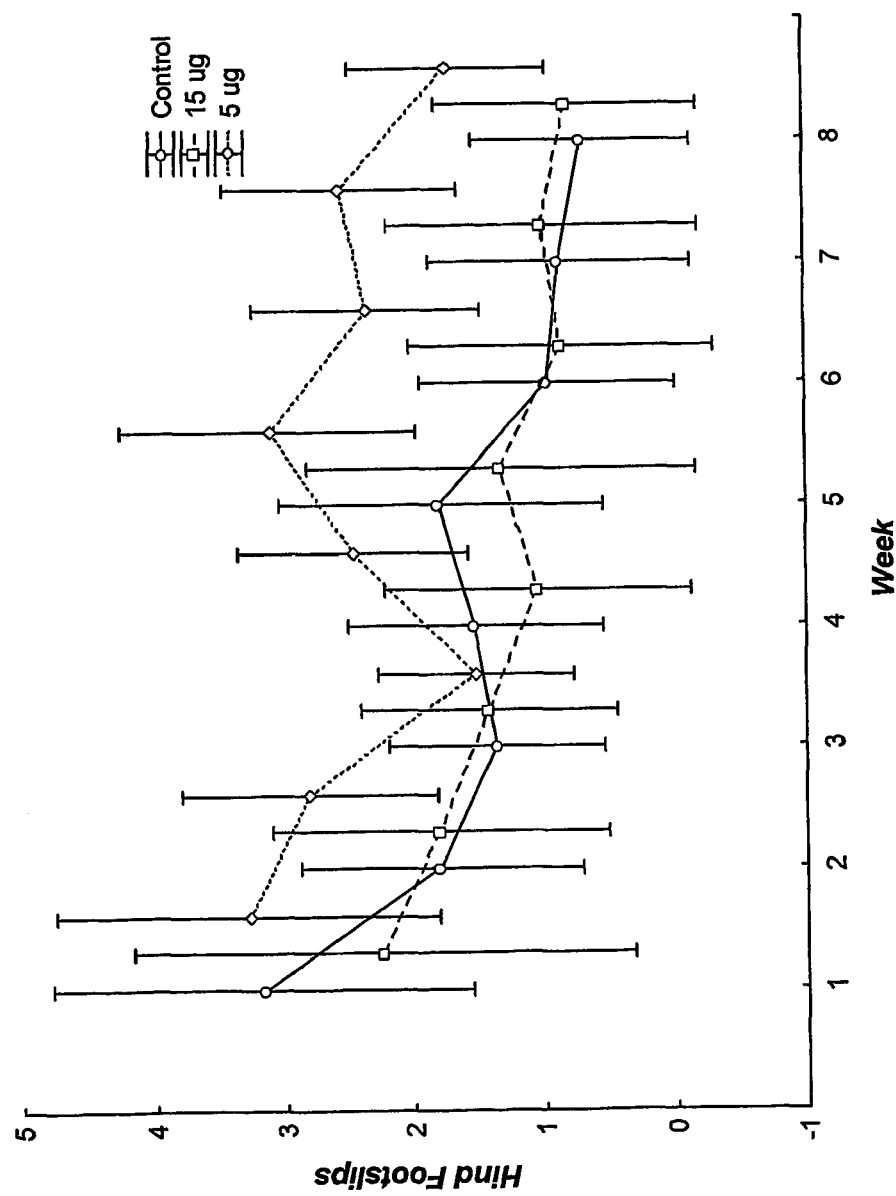

FIG. 13 shows hindlimb footslips of example 10 represented as mean±95% confidence intervals.

Figure 14A:
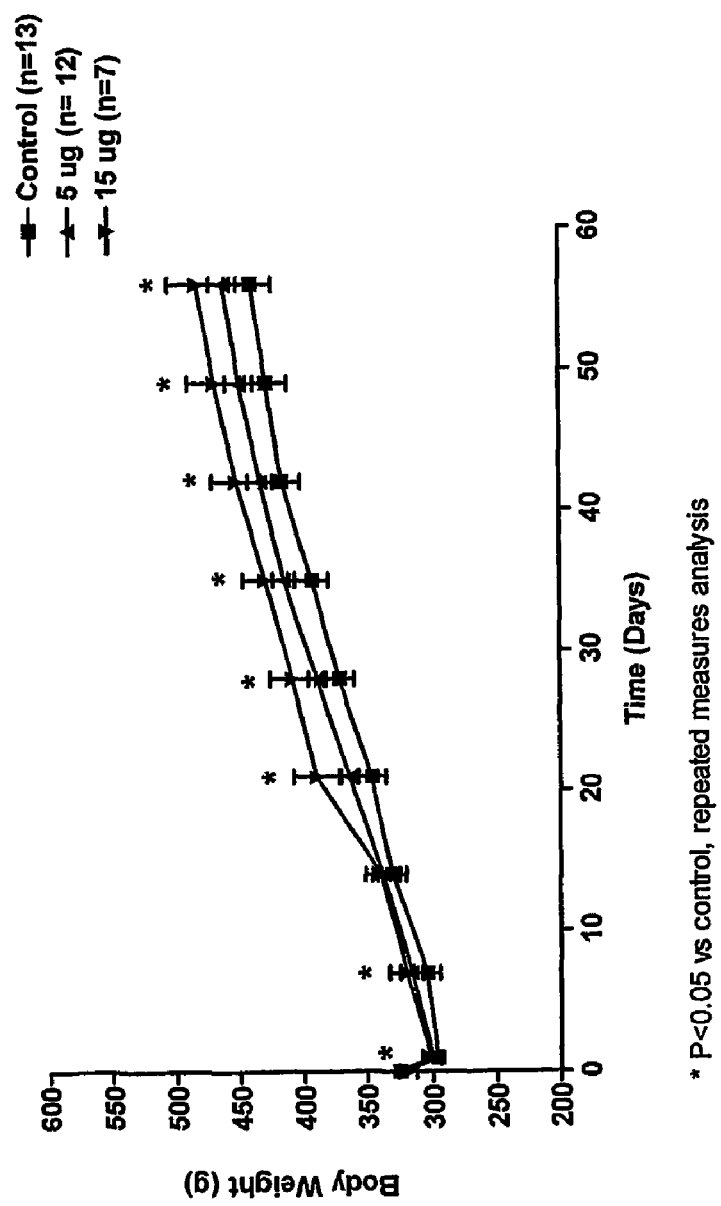

FIG. 14A) shows body weights represented as means±SEM. Dosing animals with 15 μg of the antibody causes an increase in body weight at 24 hours, 1 week and at every time point from week 3 to the completion of the study.

Figure 14B:
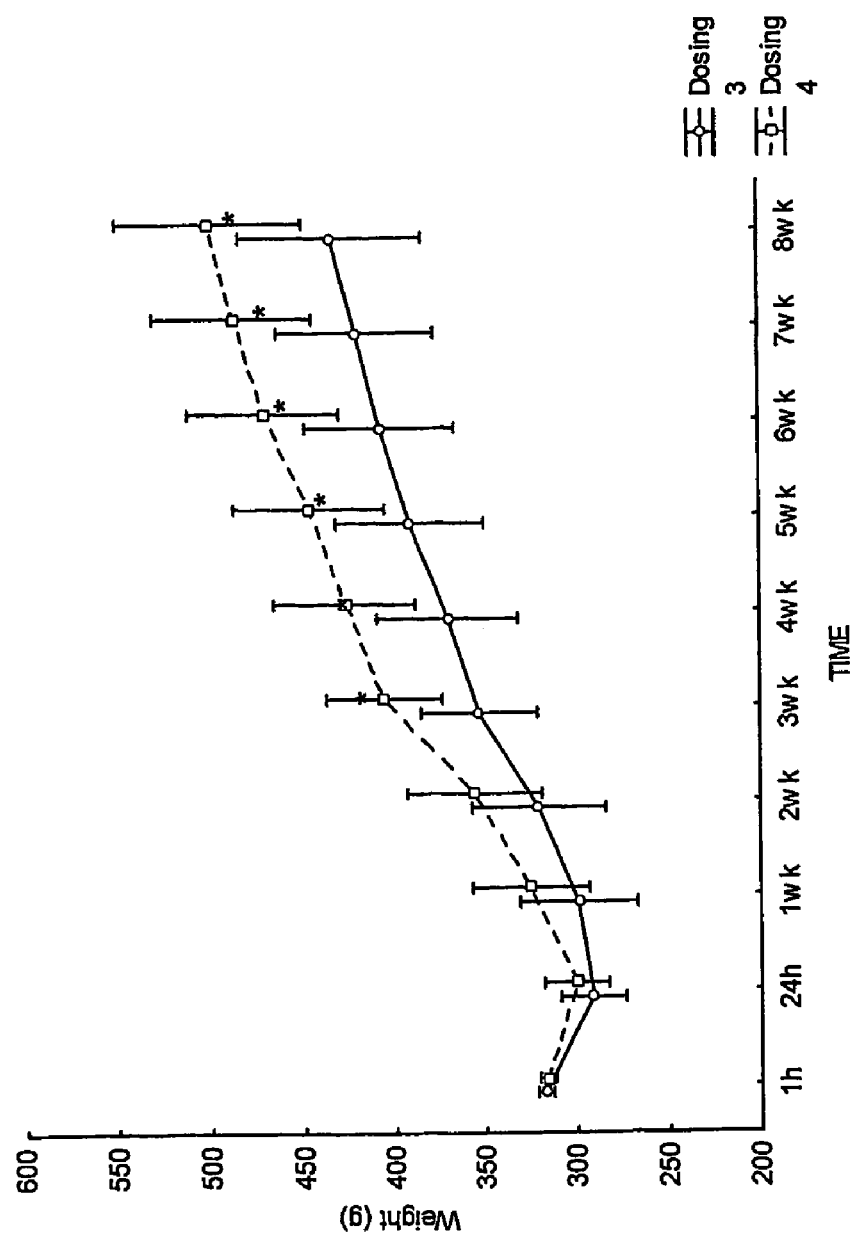

FIG. 14B) Graph shows weights for the 15 μg dosed group split into animals dosed 3 times and those dosed four times. Data expressed as means±95% confidence intervals. *P<0.05, repeated measures ANOVA.

Figure 14C:
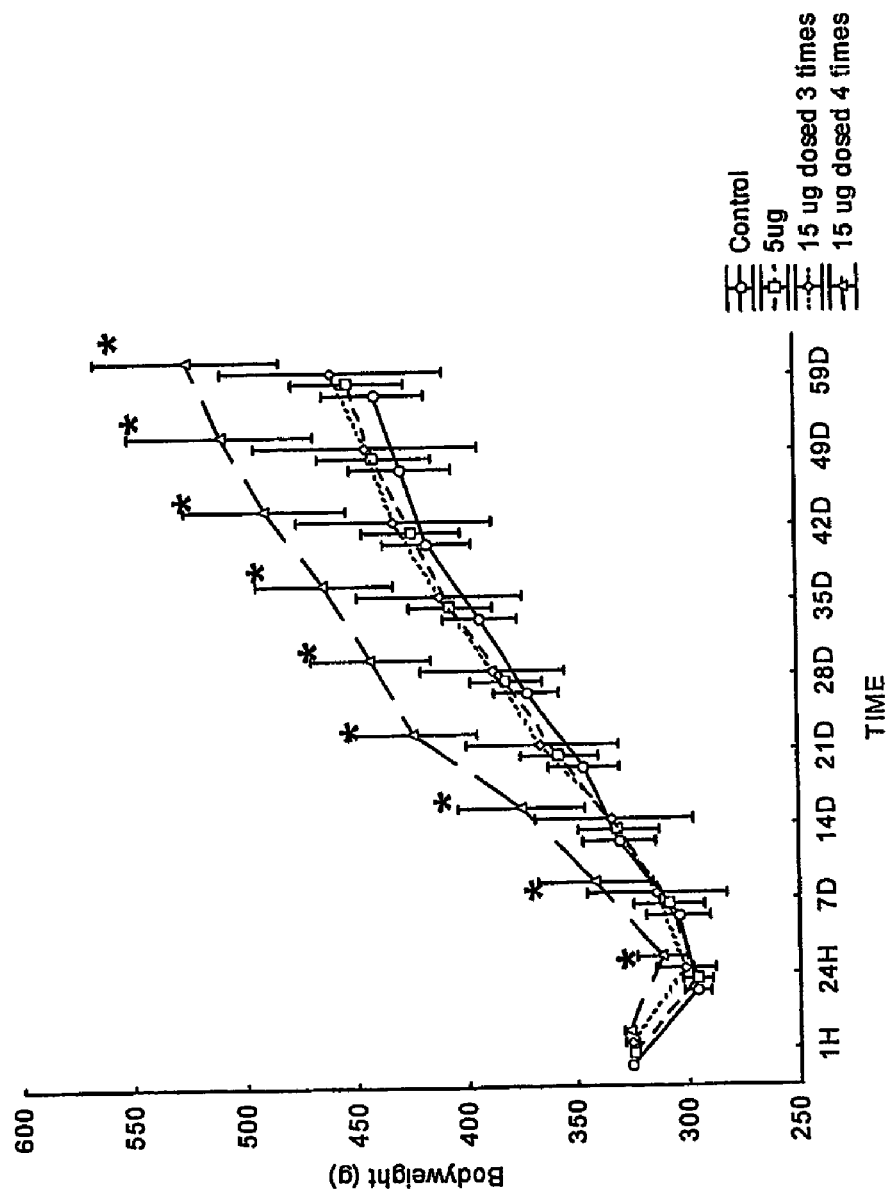

FIG. 14C) Graph shows weights for the 15 μg dosed group split into animals dosed 3 times and those dosed four times. Compared to animals dosed with 5 μg of the anti-NOGO antibody and animals dosed with control antibody. Data expressed as means±95% confidence intervals. *P<0.05, repeated measures ANOVA.

Figure 15:
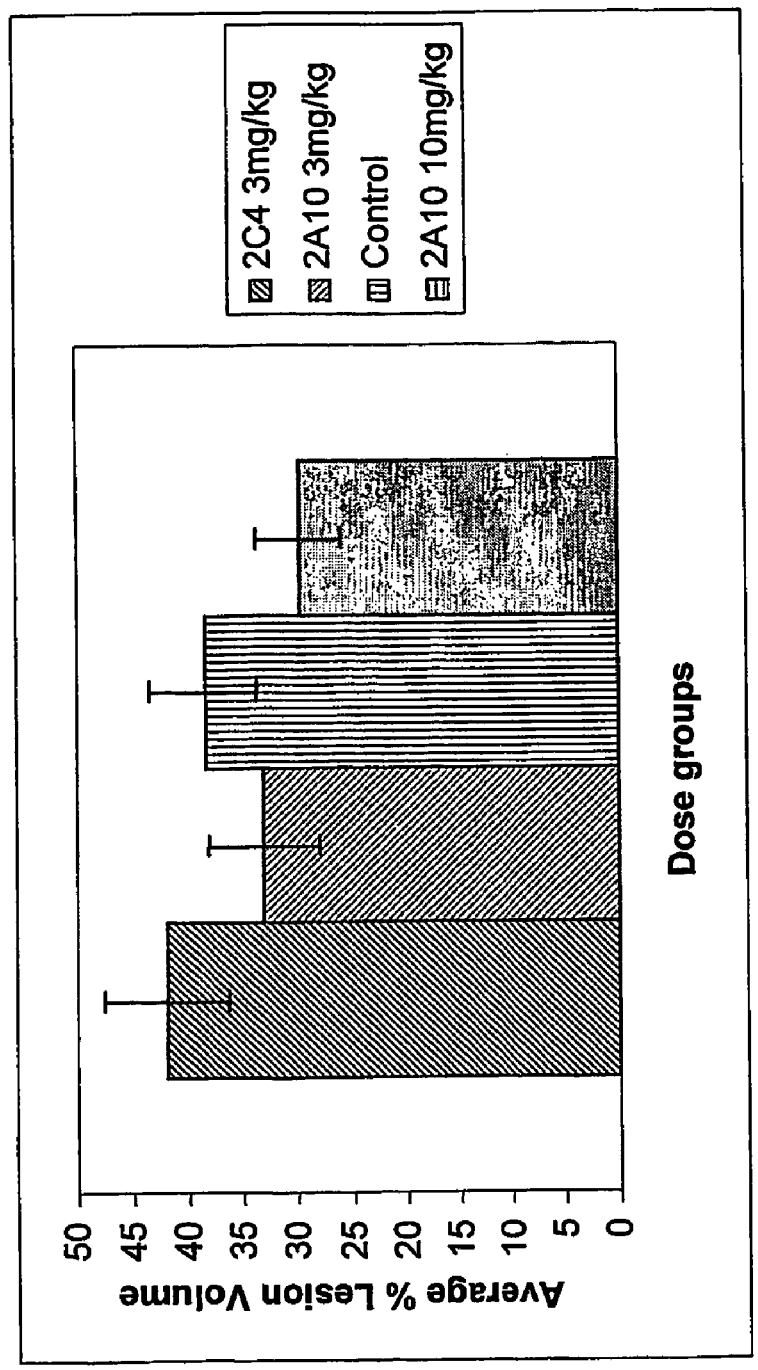

FIG. 15 represents the lesion volume as a percentage of total brain volume of example 11.

Figure 16:
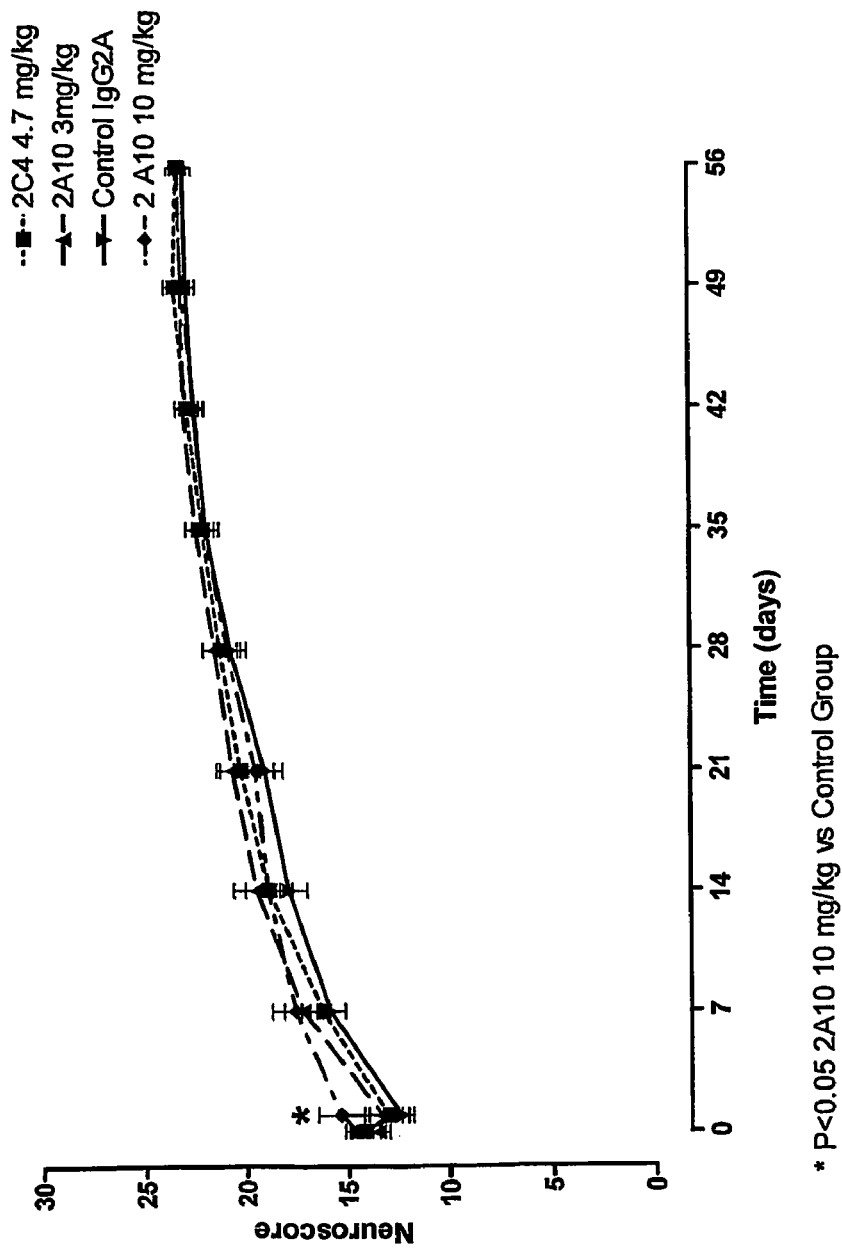

FIG. 16 shows the neuroscore data represented as means±SEM of example 11.

Figure 17A:
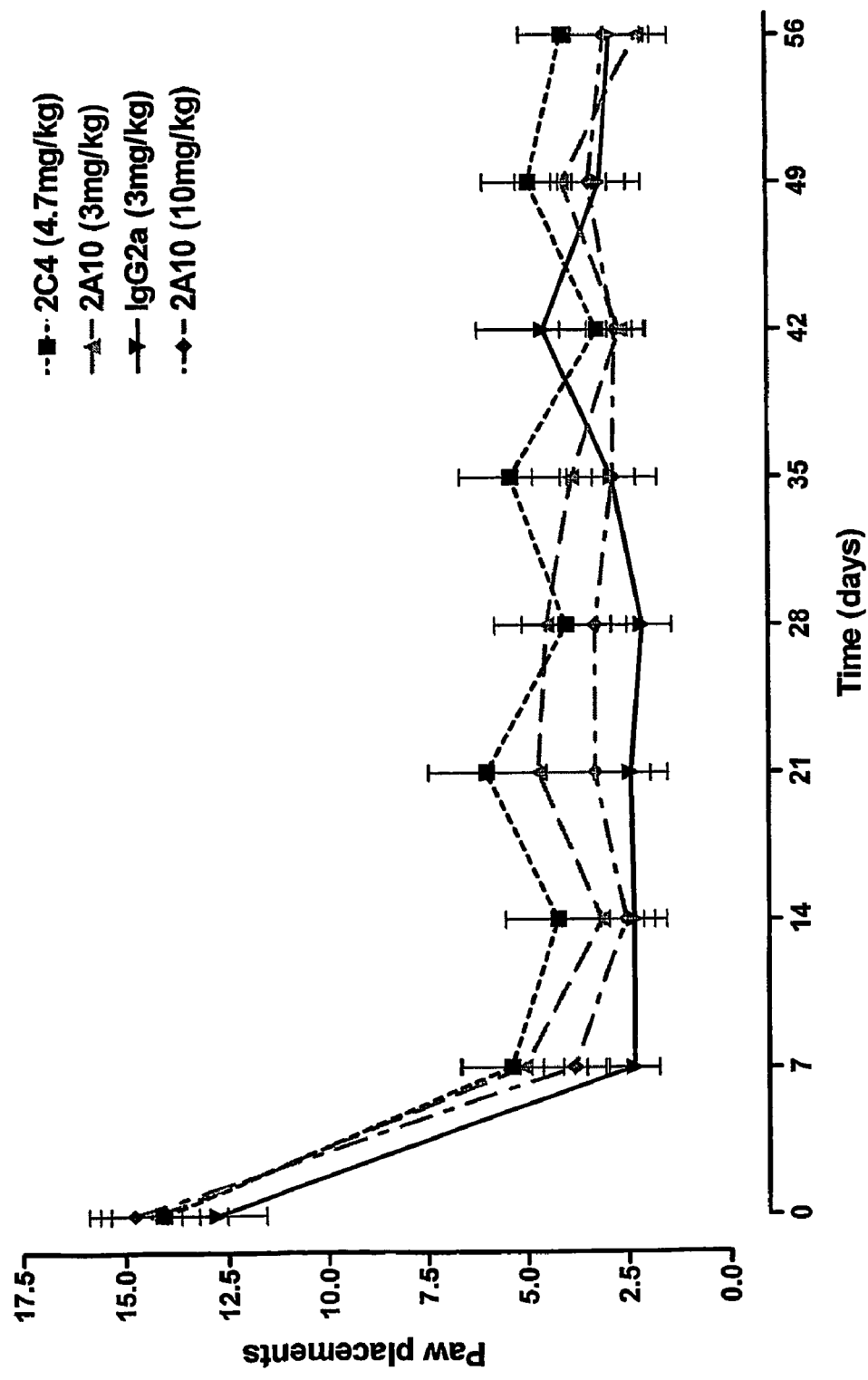
Figure 17B:
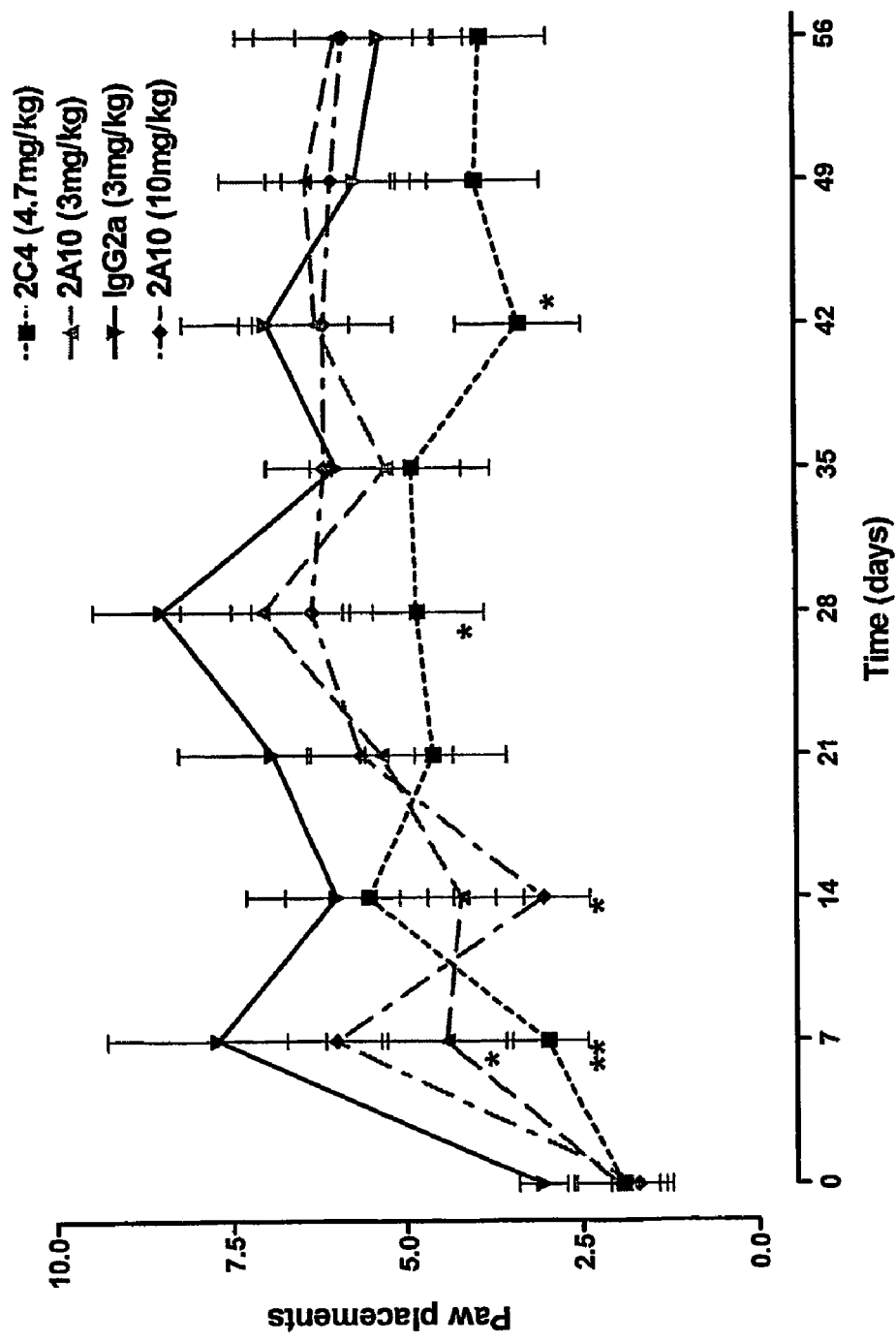
Figure 17C:
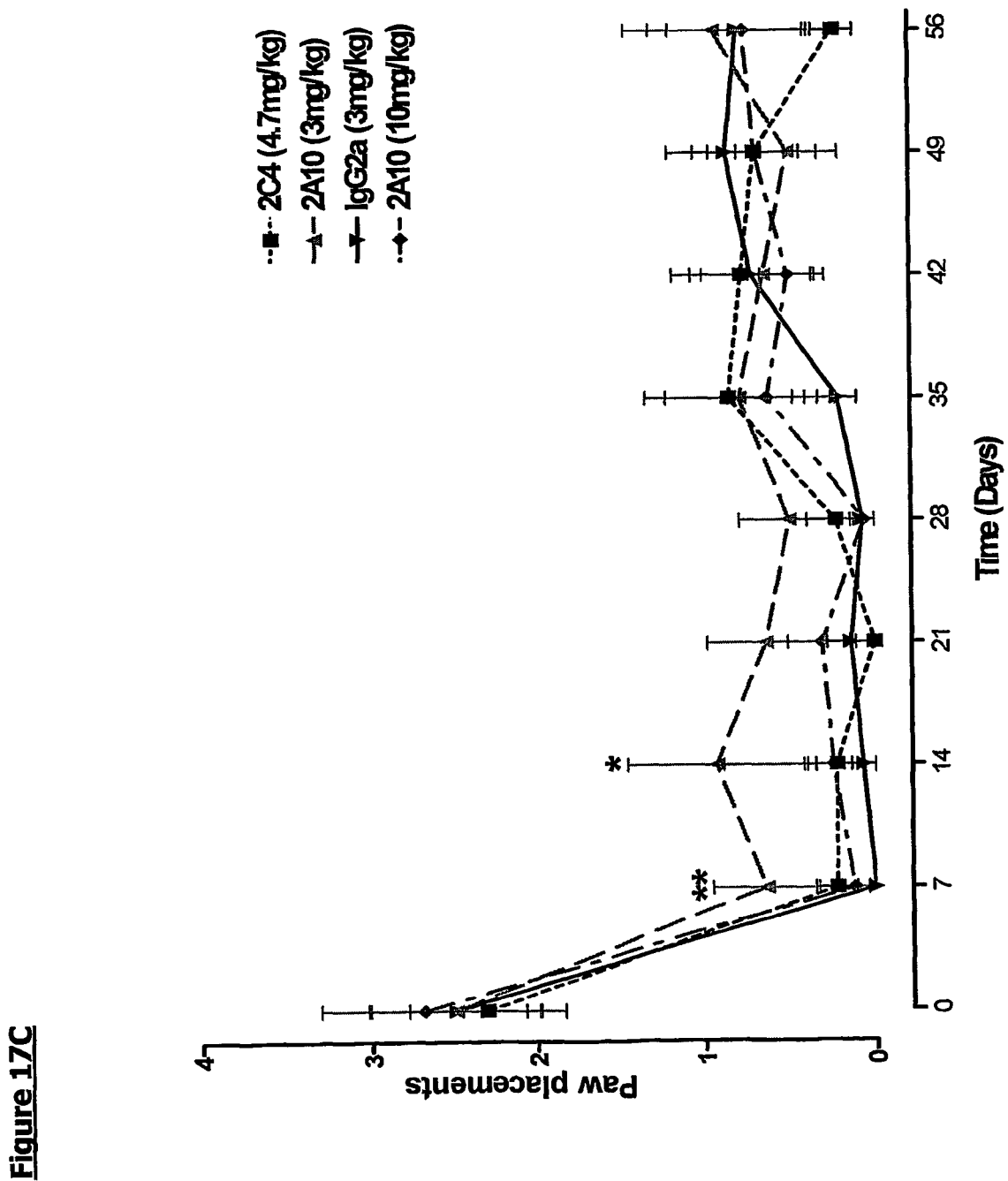

FIGS. 17A, 17B and 17C. Cylinder data represented as mean±SEM for A) both paws, B) left paw, C) right paw of example 11.

Figure 18:
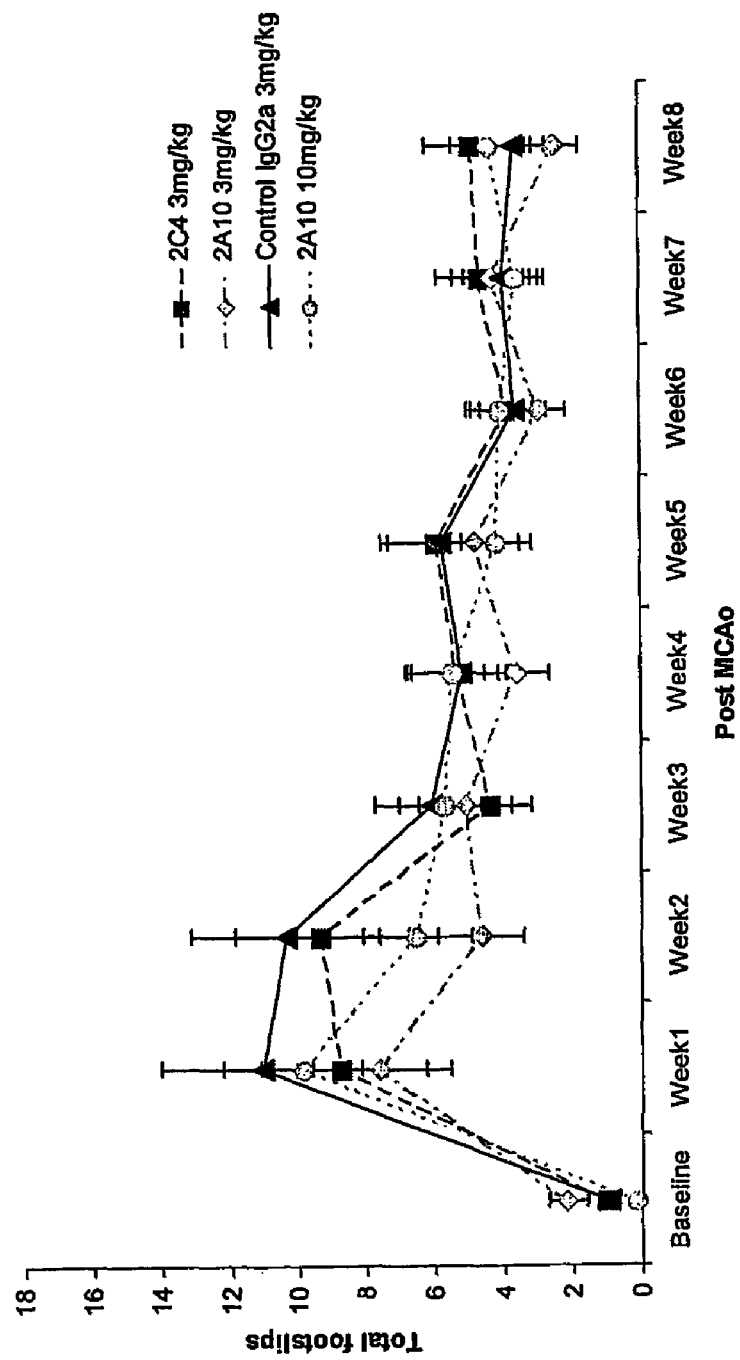

FIG. 18 shows forelimb footslips represented as mean±SEM of the tapered beam test of example 11.

Figure 19:
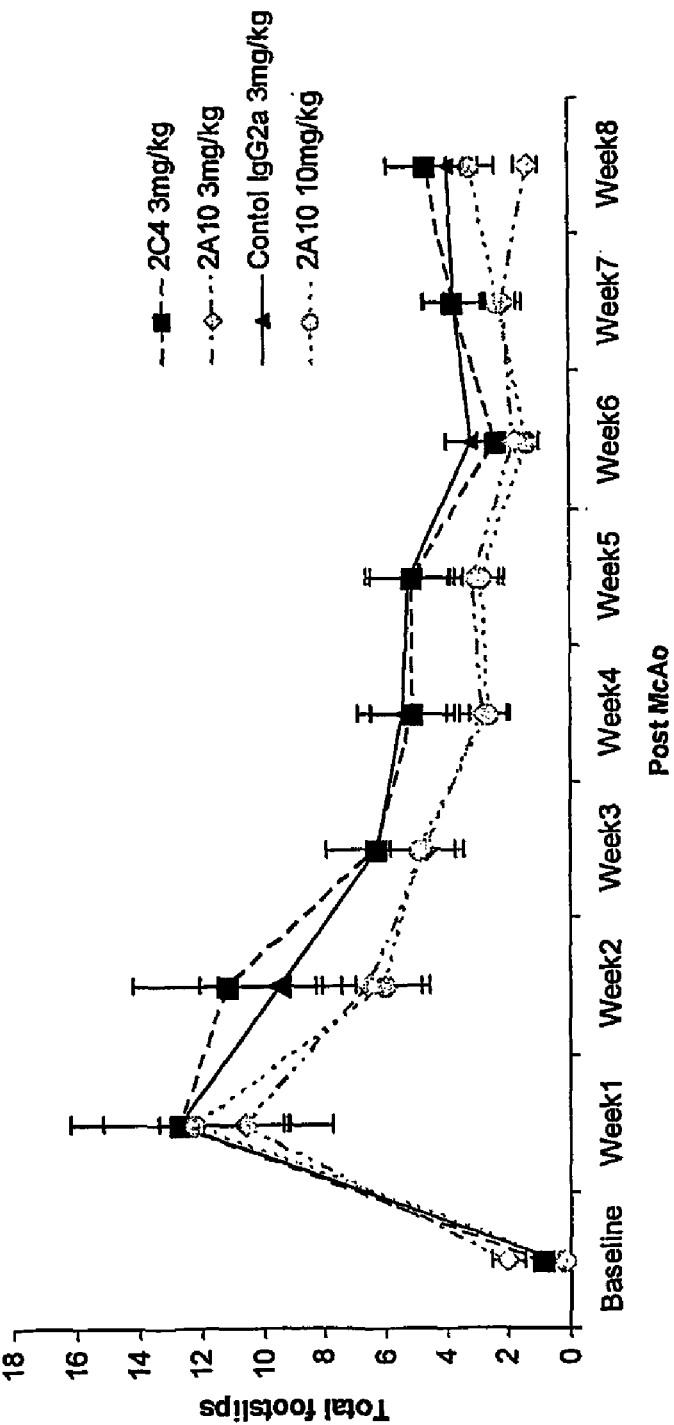

FIG. 19 shows hindlimb footslips represented as mean±SEM of example 11.

Figure 20:
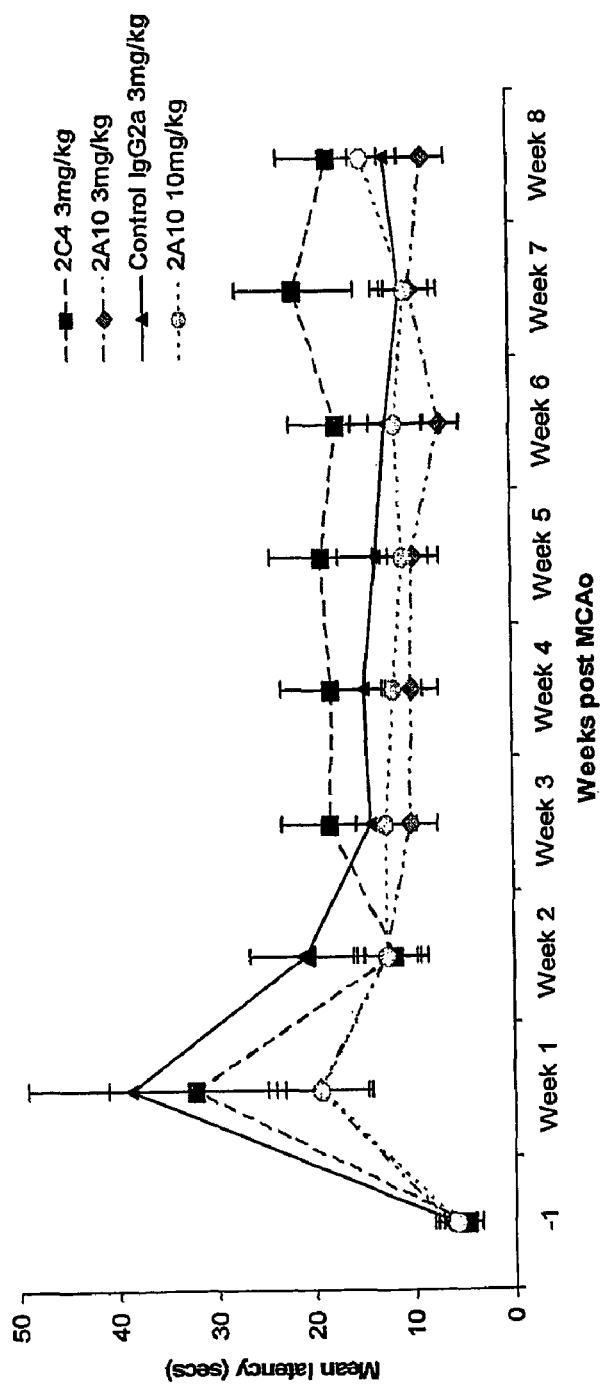

FIG. 20 shows latency to cross beam represented as mean±SEM.

Figure 21:
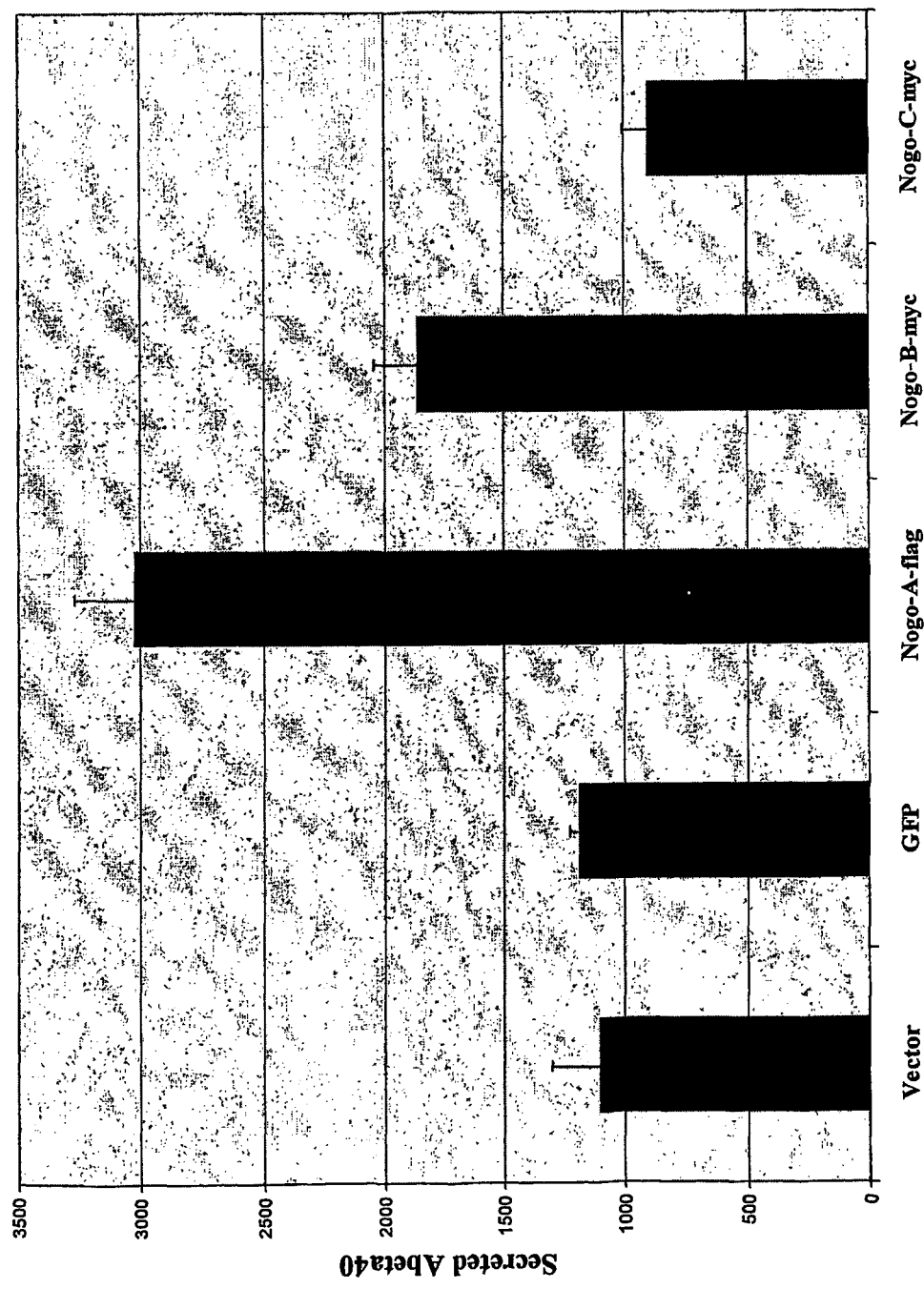

FIG. 21: NOGO A transfection leads to elevation of Aβ 40 peptide levels in SHSY5Y-APPwt cells FIG. 22: NOGO A transfection leads to elevation of Aβ 42 peptide levels in SHSY5Y-APPwt cells FIG. 23: Effect of NOGO A expression on Aβ 40 peptide levels FIG. 24: Effect of NOGO A expression on Aβ 42 peptide levels FIG. 25: Effect of NOGO A, NOGO-B and NOGO-C expression on Aβ 40 and Aβ 42

Figure 26:
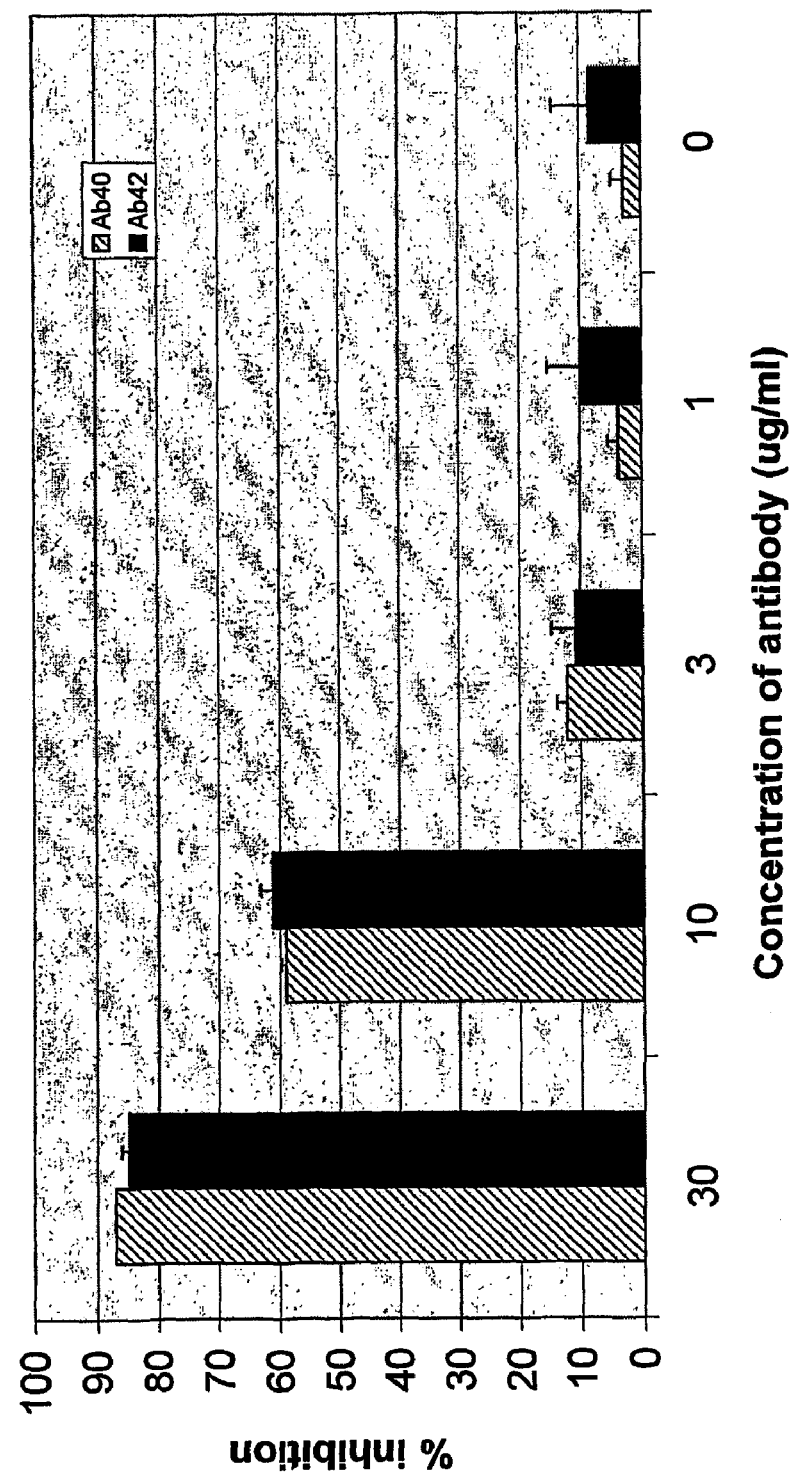

FIG. 26. Anti-NOGO A antibody 2A10-BR inhibits Aβ secretion from SHSY5Y-APPwt cells FIG. 27. Effect of control IgG1 on Aβ secretion from SHSY5Y-APPwt cells FIG. 28. Effect of control IgG1 on Aβ secretion from SHSY5Y-APPswe cells FIG. 29. Effect of control anti-NOGO (non function-blocking) antibody 6D5 on Aβ secretion from SHSY5Y-APPwt cells FIG. 30. Effect of control anti-NOGO (non function-blocking) antibody 6D5 on Aβ secretion from SHSY5Y-APPswe cells FIG. 31. Function-blocking anti-NOGO A monoclonal antibody 2A10 inhibits Aβ secretion from SHSY5Y-APPwt cells FIG. 32. Function-blocking anti-NOGO A monoclonal antibody 2A10 inhibits Aβ secretion from SHSY5Y-APPswe cells FIG. 33. Function-blocking anti-NOGO A monoclonal antibody 2C4 inhibits Aβ secretion from SHSY5Y-APPwt cells FIG. 34. Effect of anti-NOGO A static culture antibody preparations and additional control antibodies on Aβ secretion from SHSY5Y-APPwt cells. 2A10, 2C4 and 15C3 are the static culture antibodies. All others are BR (Bioreactor) purified controls or commercially available controls.

Figure 35A:
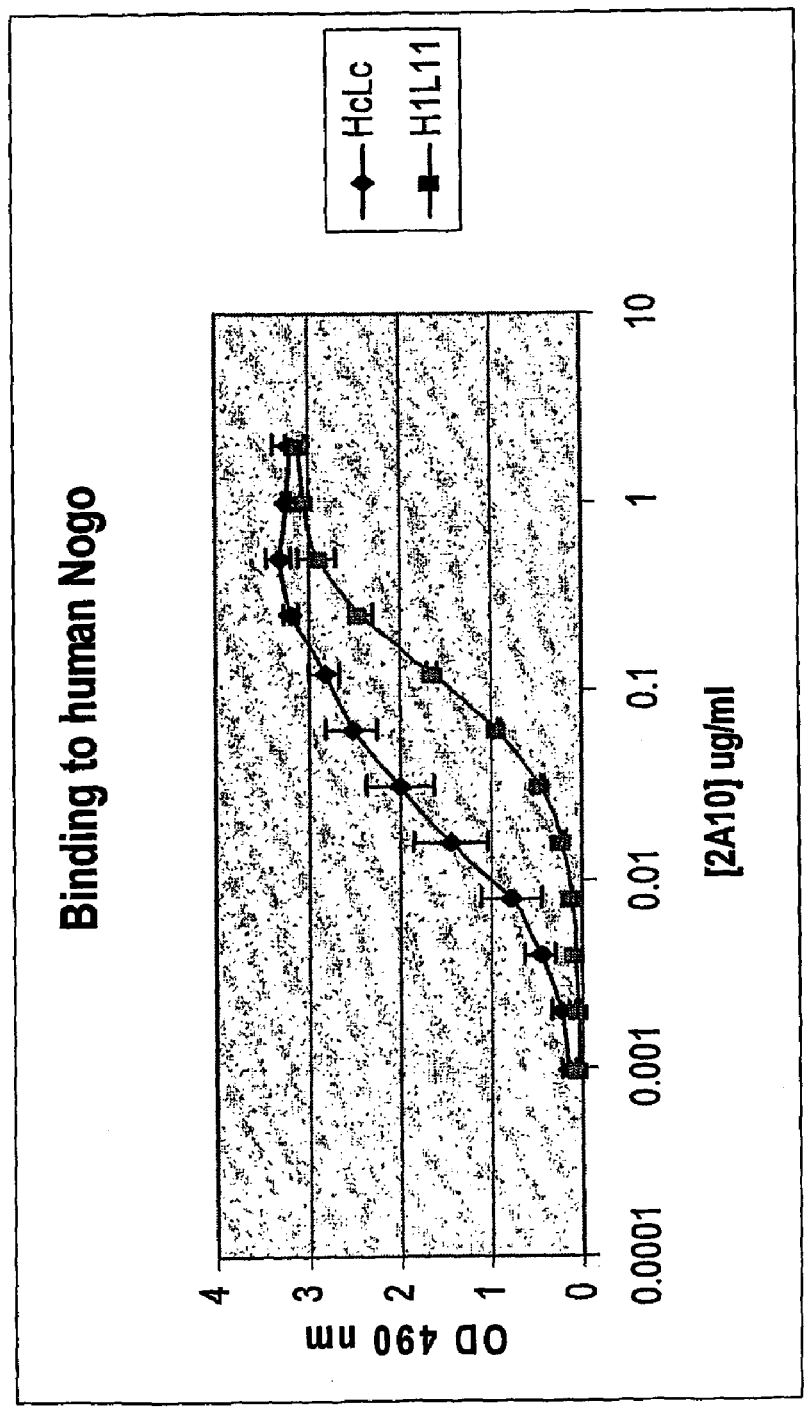
Figure 35B:
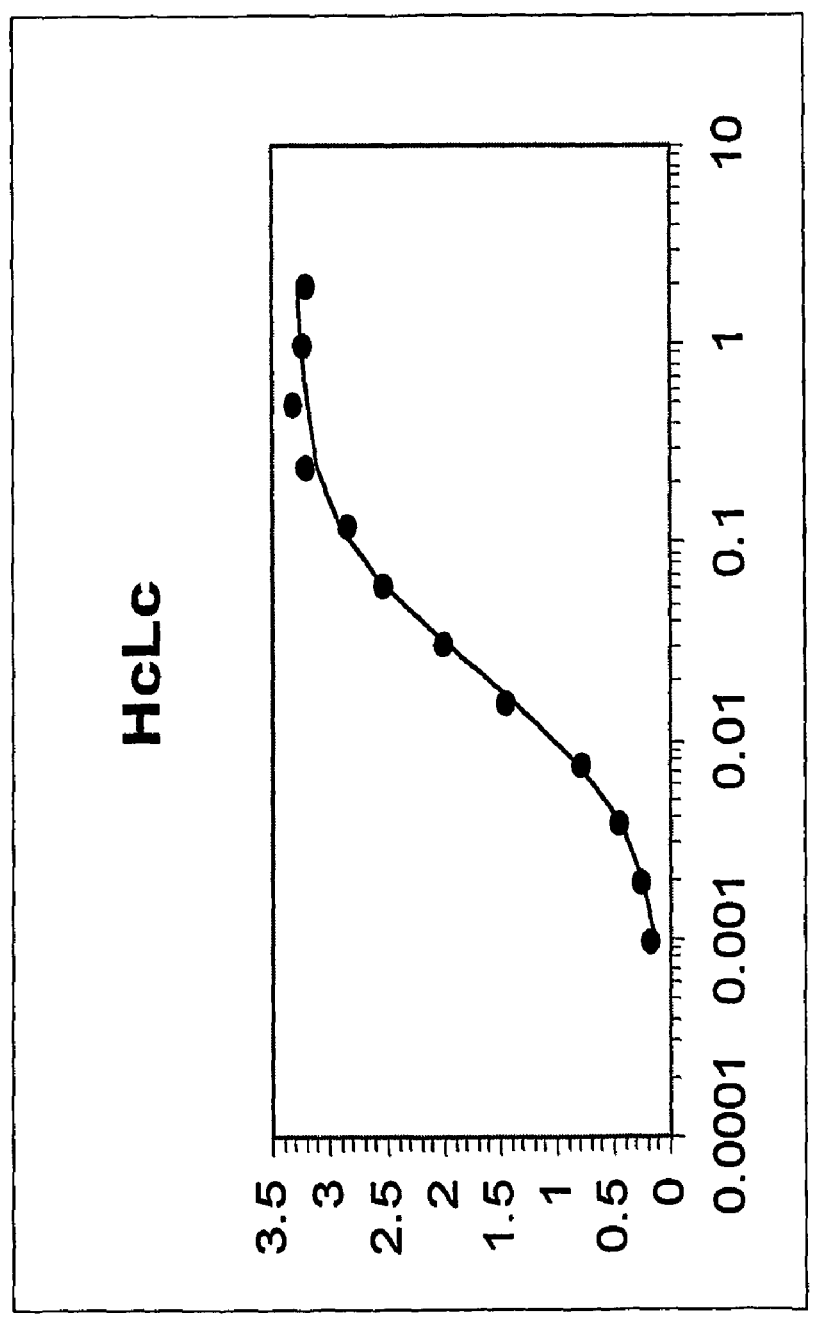
Figure 35C:
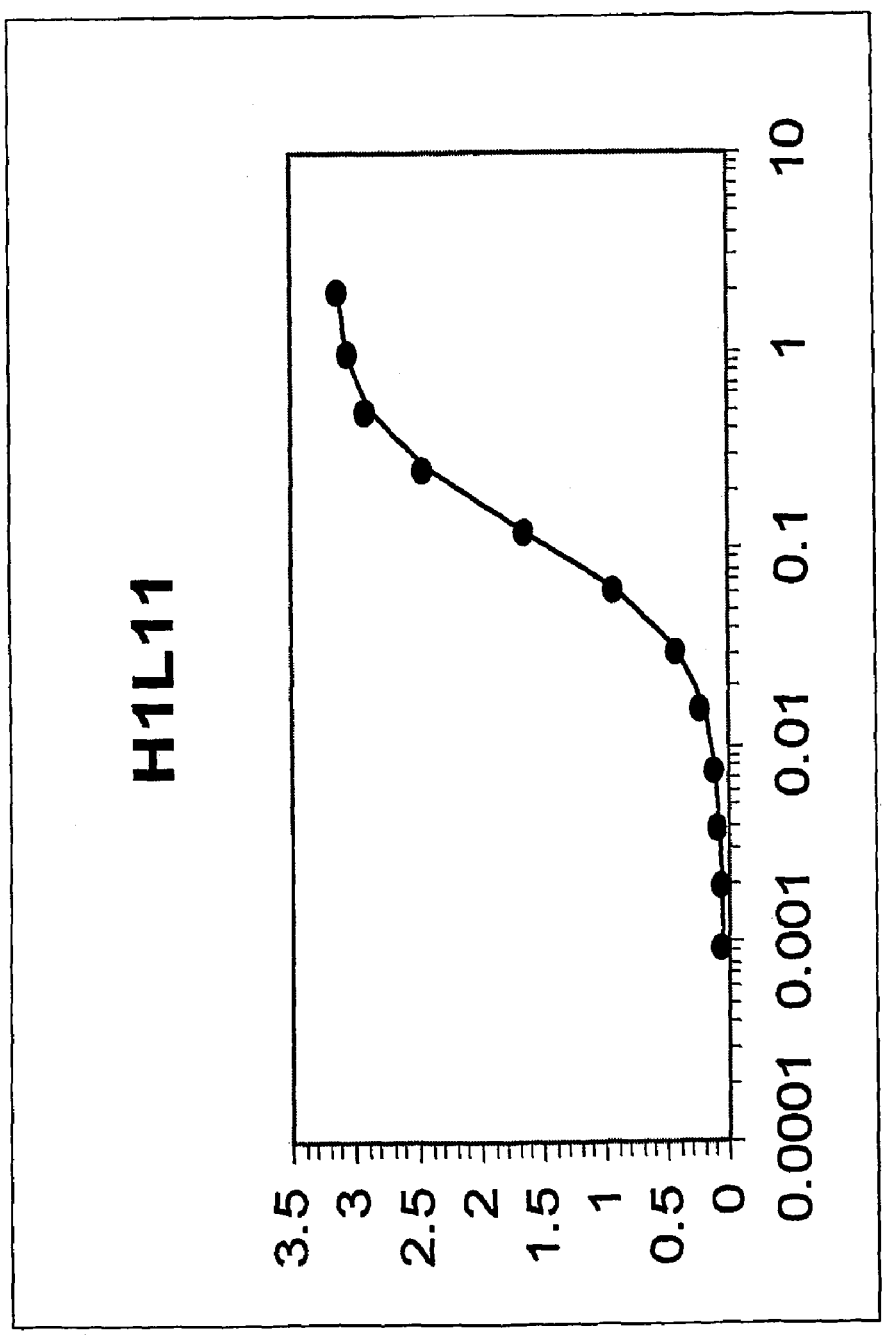

FIGS. 35A to C illustrates the dose-dependent binding of humanised antibody H1L11 in comparison with the chimera (HcLc) to human NOGO-A56 in an ELISA assay. The Y-axis shows the measured optical density (OD) at 490 nm, a quantitative measure of antibody captured in the wells. The X-axis shows the concentration of antibody used (ug/ml) per well at each data point.

Figure 36:
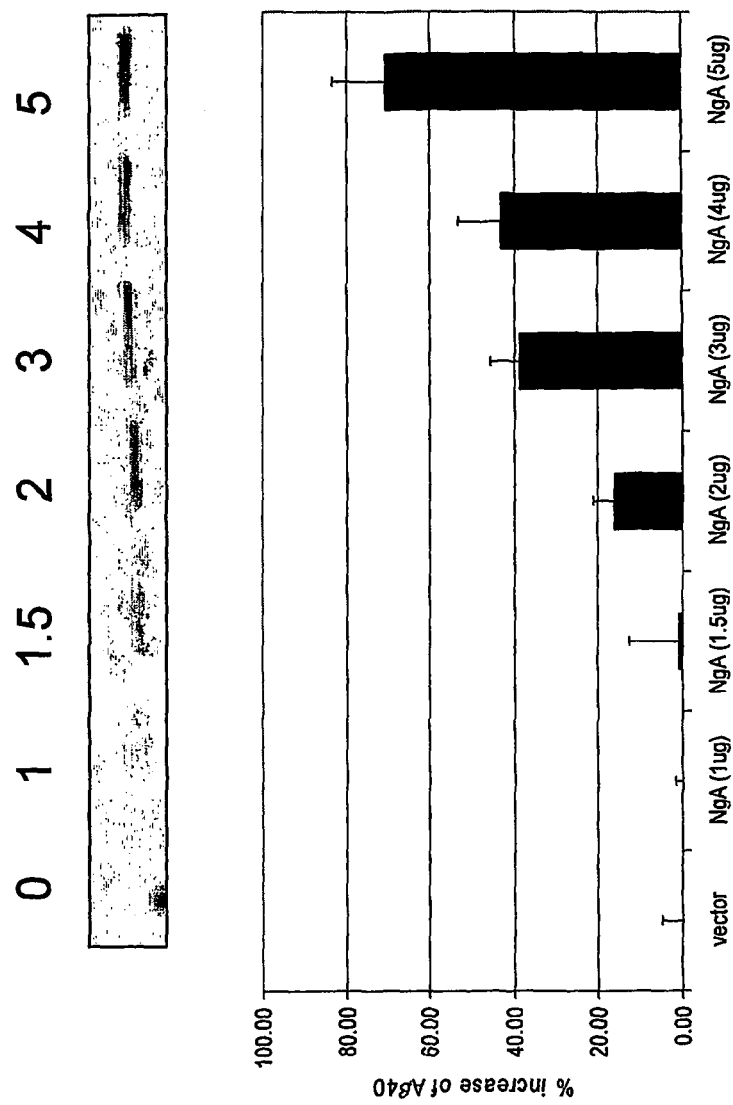

FIG. 36. Increased NogoA expression elevates Aβ levels in a dose-dependent manner. The Y axis of the graph is % increase of Aβ40. The X-axis shows the increasing concentration of myc-tagged NogoA cDNA. Above the graph is a gel showing the increased amount of NogoA protein expression as shown by western blotting using an anti-NogoA antibody

DETAILED DESCRIPTION OF THE INVENTION

Antibodies of the invention are typically monoclonal antibodies (mAb) and are preferably chimeric, humanised, fully human or reshaped. Of these humanised and fully human are particularly preferred.

Antibodies of the invention typically have the structure of a natural antibody or functional fragment thereof. The antibody may therefore comprise a full length antibody, a. (Fab')₂ fragment, a Fab fragment, a light chain dimer or a heavy chain dimer. The antibody may be an IgG1, IgG2, IgG3, or IgG4; or IgM; IgA, IgE or IgD or a modified variant thereof. The constant domain of the antibody heavy chain may be selected accordingly. The light chain constant domain may be a kappa or lambda constant domain. Furthermore, the antibody may comprise modifications of all classes eg IgG dimers, Fc mutants that no longer bind Fc receptors or mediate C1q binding. The antibody may also be a chimeric antibody of the type described in WO86/01533 which comprises an antigen binding region and a non-immunoglobulin region. The antigen binding region is an antibody light chain variable domain or heavy chain variable domain. Typically the antigen binding region comprises both light and heavy chain variable domains. The non-immunoglobulin region is fused at its C terminus to the antigen binding region. The non-immunoglobulin region is typically a non-immunoglobulin, protein and may be an enzyme, a toxin or protein having known binding specificity. The two regions of this type of chimeric antibody may be connected via a cleavable linker sequence. Immunoadhesins having the CDRs as hereinbefore described are also contemplated in the present invention.

The constant region is selected according to the functionality required. Normally an IgG1 will demonstrate lytic ability through binding to complement and/or will mediate ADCC (antibody dependent cell cytotoxicity). An IgG4 will be preferred if a non-cytotoxic blocking antibody is required. However, IgG4 antibodies can demonstrate instability in production and therefore it may be more preferable to modify the generally more stable IgG1. Suggested modifications are described in EP0307434 preferred modifications include at positions 235 and 237. The invention therefore provides a lytic or a non-lytic form of an antibody according to the invention.

In preferred forms therefore the antibody of the invention is a full length (i.e. H2L2 tetramer) non-lytic IgG1 antibody having the CDRs described supra. In most preferred forms we provide a full length non-lytic IgG1 antibody having the CDRs of SEQ ID NOs 1 to 6; SEQ ID NOs 7 to 12 or SEQ ID NOs 13 to 18.

In a further aspect, the invention provides polynucleotides encoding the. CDRs. For example the invention provides polynucleotides encoding CDRH1, CDRH2, CDRH3, CDRL1, CDRL2 and CDRL3 as disclosed in tables 1 to 6. Preferred polynucleotide sequences are shown below in tables 7 to 12.

TABLE 7

Antibody 2A10/3 light chain CDRs

| CDR | |
|---|---|
| L1 | AGGTCTAGTAAGAGTCTCCTATATAAGGATG (SEQ ID NO: 19) GGAAGACATACTTGAAT |
| L2 | TTGATGTCCACCCGTGCATCA (SEQ ID NO: 20) |
| L3 | CAACAACTTGTAGAGTATCCGCTCACG (SEQ ID NO: 21) |

TABLE 8

Antibody 2A10/3 heavy chain CDRs

| CDR | |
|---|---|
| H1 | AGCTACTGGATGCAC (SEQ ID NO: 22) |
| H2 | AATATTAATCCTAGCAATGGTGGTACTAACTAC AATGAGAAGTTCAAGAGC (SEQ ID NO: 23) |
| H3 | GGACAGGGCTAC (SEQ ID NO: 24) |

TABLE 9

Antibody 2C4/1 light chain CDRs

| CDR | |
|---|---|
| L1 | AGATCTAGTCAGAGCCTTGTACACAGTAATG (SEQ ID NO: 25) GAAACACCTATTTACAT |
| L2 | AAAGTTTCCAACCGATTTTCT (SEQ ID NO: 26) |
| L3 | TCTCAGAGTACACATGTTCCG (SEQ ID NO: 27) CTCACG |

TABLE 10

Antibody 2C4/1 heavy chain CDRs

| CDR | |
|---|---|
| H1 | TTCAGTTGCTATGCCATGTCT (SEQ ID NO: 28) |
| H2 | TCCATTAGTGATGGTGGTAGTTACACCTACTAT CCAGACAATGTAAAGGGC (SEQ ID NO: 29) |
| H3 | GAACTACTTTTTGACTAC (SEQ ID NO: 30) |

TABLE 11

Antibody 15C3/3 light chain CDRs

| CDR | |
|---|---|
| L1 | AGGTCTAGTAAGAGTCTCCTGCATAGTAATGGCAACACTTACTTGT AT (SEQ ID NO:31) |
| L2 | CGGATGTCCAACCTTGCCTCA (SEQ ID NO:32) |
| L3 | ATGCAACATCTAGAATATCCGCTCACG (SEQ ID NO:33) |

TABLE 12

Antibody 15C/3 heavy chain CDRs

| CDR | |
|---|---|
| H1 | AGCTACTGGATGAAC (SEQ ID NO:34) |
| H2 | CAGATTTATCCTGGAGATGGTGATACTAACTACAACGGAAAGTTCAA GGGC (SEQ ID NO:35) |
| H3 | CGCTTTGACTAT (SEQ ID NO:36) |

In a further aspect of the invention, there is provided a polynucleotide encoding a light chain variable region of an anti-NOGO antibody including at least one CDR selected from CDRL1, CDRL2 and CDRL3 in table 1, 3, 5, more preferably including all 3 CDRs in table 1 or all 3 CDRs in table 3 or all 3 CDRs in table 5.

In a further aspect of the invention, there is provided a polynucleotide encoding a heavy chain variable region of an anti-NOGO antibody including at least one CDR selected from CDRH1, CDRH2 and CDRH3, more preferably including all 3 CDRs in table 2 or all 3 CDRs in table 4 or all 3 CDRs in table 6.

The invention further provides an anti-NOGO antibody, or functional fragment thereof, that binds to and neutralises the activity of NOGO, preferably human NOGO and more preferably human NOGO-A which comprises a heavy chain variable region comprising one of the following amino acid sequences:

(SEQ ID NO:37)
QVQLQQPGTELVKPGASVKLSCKASGYTFTSYWMHWVKQRPGQGLEWIGN
INPSNGGTNYNEKFKSKATLTVDKSSSTAYMQLSSLTSEDSAVYYCELGQ
GYWGQGTTLTVSS;
or (SEQ ID NO:38)
EVQLVESGGGLVKPGGSLKLSCAASGFTFSCYAMSWVRQTPEKRLEWVAS
ISDGGSYTYYPDNVKGRFTISRDNAKNNLYLQMSHLKSEDTAMYYCAKEL
LFDYWGQGTTLTVSS;
or (SEQ ID NO:39)
QVQLQQSGAELVKPGASVKISCKASGYAFSSYWNNWVKQRPGKGLEWIGQ
IYPGDGDTNYNGKFKGKATLTADKSSSTAYMQLSSLTSEDSAVYFCAVRF
DYWGQGTTLTVSS.

The invention further provides an anti-NOGO antibody, or functional fragment thereof, that binds to and neutralises NOGO which comprises a light chain variable region comprising one of the following amino acid sequences:

(SEQ ID NO:40)
DIVITQDELSNPVTSGESVSISCRSSKSLLYKDGKTYLNWFLQRPGQSPQ
LLIYLMSTRASGVSDRFSGSGSGTDFTLEISRVKAEDVGVYYCQQLVEYP
LTFGAGTKLELK (SEQ ID NO:41)
DVVMTQTPLSLPVSLGDQASISCRSSQSLVHSNGNTYLHWYLQKPGQSPK
LLIYKVSNRFSGVPDRFSGSGSGTDFTLKISRVEAEDLGVYFCSQSTHVP
LTFGAGTKLELK.

(SEQ ID NO:42)
DIVMTQAAPSVPVTPGESVSISCRSSKSLLHSNGNTYLYWFLQRPGQSPQ
LLIYRMSNLASGVPDRFSGSGSGTAFTLRISRVEAEDVGVYYCMQHLEYP
LTFGAGTKLELK.

In a further aspect of the invention there is provided an anti-NOGO antibody, or functional fragment thereof, which binds to and neutralises the activity of NOGO, preferably human NOGO, more preferably human NOGO-A which comprises:
a) a heavy chain variable region of SEQ ID NO:37 together with a light chain variable region comprising the amino acid sequence of SEQ ID NO:40; or
b) a heavy chain variable region of SEQ ID NO:38 together with a light chain variable region comprising the amino acid sequence of SEQ ID NO:41; or
c) a heavy chain variable region of SEQ ID NO:39 together with a light chain variable region comprising the amino acid sequence of SEQ ID NO:42.

In a further aspect of the present invention there is provided an anti-NOGO antibody, or functional fragment thereof, comprising:
a heavy chain variable fragment comprising SEQ ID NO:37, and a constant part or fragment thereof of a human heavy chain and
a light chain variable fragment comprising SEQ ID No:40 and a constant part or fragment thereof of a human light chain; or
a heavy chain variable fragment comprising SEQ ID NO:38 and a constant part or fragment thereof of a human heavy chain; and
a light chain variable fragment comprising SEQ ID No:41 and a constant part or fragment thereof of a human light chain or a heavy chain variable fragment comprising SEQ ID NO:39 and a constant part or fragment thereof of a human heavy chain; and
a light chain variable fragment comprising SEQ ID No:42 and a constant part or fragment thereof of a human light chain.

In a further aspect, the invention provides polynucleotides encoding the heavy chain variable region comprising the amino acid sequences of SEQ ID NOs 37 to 39 and light chain variable regions comprising the amino acid sequences of SEQ ID NOs 40 to 42.

A preferred polynucleotide sequence encoding the amino acid sequence of SEQ ID NO: 37 is (SEQ ID NO:43)
CAGGTCCAACTGCAGCAGCCTGGGACTGAACTGGTGAAGCCTGGGGCTTC

AGTGAAGCTGTCCTGCAAGGCTTCTGGCTACACCTTCACCAGCTACTGGA

TGCACTGGGTGAAGCAGAGGCCTGGACAAGGCCTTGAGTGGATTGGAAAT

ATTAATCCTAGCAATGGTGGTACTAACTACAATGAGAAGTTCAAGAGCAA

GGCCACACTGACTGTAGACAAATCCTCCAGCACAGCCTACATGCAGCTCA

GCAGCCTGACATCTGAGGACTCTGCGGTCTATTATTGTGAACTGGGACAG

GGCTACTGGGGCCAAGGCACCACTCTCACAGTCTCCTCA

A preferred polynucleotide sequence encoding the amino acid sequence of SEQ ID NO: 38 is:

(SEQ ID NO:44)
GAAGTGCAGCTGGTGGAGTCTGGGGGAGGCTTAGTGAAGCCTGGAGGGTC

CCTGAAACTCTCCTGTGCAGCCTCTGGATTCACTTTCAGTTGCTATGCCA

TGTCTTGGGTTCGCCAGACTCCGGAAAAGAGGCTGGAGTGGGTCGCATCC

ATTAGTGATGGTGGTAGTTACACCTACTATCCAGACAATGTAAAGGGCCG

ATTCACCATCTCCAGAGACAATGCCAAGAACAACCTGTACCTGCAAATGA

GCCATCTGAAGTCTGAGGACACAGCCATGTATTACTGTGCAAAGGAACTA

CTTTTTGACTACTGGGGCCAAGGCACCACTCTCACAGTCTCCTCA

A preferred polynucleotide sequence encoding the amino acid sequence of SEQ ID NO: 39 is:

(SEQ ID NO:45)
CAGGTTCAGCTGCAGCAGTCTGGGGCTGAGCTGGTGAAGCCTGGGGCCTC

AGTGAAGATTTCCTGCAAAGCTTCTGGCTACGCATTCAGTAGCTACTGGA

TGAACTGGGTGAAGCAGAGGCCTGGAAAGGGTCTTGAGTGGATTGGACAG

ATTTATCCTGGAGATGGTGATACTAACTACAACGGAAAGTTCAAGGGCAA

GGCCACACTGACTGCAGACAAATCCTCCAGCACAGCCTACATGCAGCTCA

GCAGCCTGACCTCTGAGGACTCTGCGGTCTATTTCTGTGCAGTACGCTTT

GACTATTGGGGCCAAGGCACCACTCTCACAGTCTCCTCA

A preferred polynucleotide sequence encoding the amino acid sequence of SEQ ID NO: 40 is:

(SEQ ID NO:46)
GATATTGTGATAACCCAGGATGAACTCTCCAATCCTGTCACTTCTGGAGA

ATCAGTTTCCATCTCCTGCAGGTCTAGTAAGAGTCTCCTATATAAGGATG

-continued
GGAAGACATACTTGAATTGGTTTCTGCAGAGACCAGGACAATCTCCTCAG

CTCCTGATCTATTTGATGTCCACCCGTGCATCAGGAGTCTCAGACCGGTT

TAGTGGCAGTGGGTCAGGAACAGATTTCACCCTGGAAATCAGTAGAGTGA

AGGCTGAGGATGTGGGTGTGTATTACTGTCAACAACTTGTAGAGTATCCG

CTCACGTTCGGTGCTGGGACCAAGCTGGAGCTGAAA

A preferred polynucleotide sequence encoding the amino acid sequence of SEQ ID NO: 41 is:

(SEQ ID NO:47)
GATGTTGTGATGACCCAAACTCCACTCTCCCTGCCTGTCAGTCTTGGAGA

TCAAGCCTCCATCTCTTGCAGATCTAGTCAGAGCCTTGTACACAGTAATG

GAAACACCTATTTACATTGGTACCTGCAGAAGCCAGGCCAGTCTCCAAAG

CTCCTGATCTACAAAGTTTCCAACCGATTTTCTGGGGTCCCAGACAGGTT

CAGTGGCAGTGGATCAGGGACAGATTTCACACTCAAGATCAGCAGAGTGG

AGGCTGAGGATCTGGGAGTTTATTTCTGCTCTCAGAGTACACATGTTCCG

CTCACGTTCGGTGCTGGGACCAAGCTGGAGCTGAAA

A preferred polynucleotide sequence encoding the amino acid sequence of SEQ ID NO: 42 is:

(SEQ ID NO:48)
GATATTGTGATGACTCAGGCTGCACCCTCTGTACCTGTCACTCCTGGAGA

GTCAGTATCCATCTCCTGCAGGTCTAGTAAGAGTCTCCTGCATAGTAATG

GCAACACTTACTTGTATTGGTTCCTGCAGAGGCCAGGCCAGTCTCCTCAG

CTCCTGATATATCGGATGTCCAACCTTGCCTCAGGAGTCCCAGACAGGTT

CAGTGGCAGTGGGTCAGGAACTGCTTTCACACTGAGAATCAGTAGAGTGG

AGGCTGAGGATGTGGGTGTTTATTACTGTATGCAACATCTAGAATATCCG

CTCACGTTCGGTGCTGGGACCAAGCTGGAGCTGAAA

Anti-NOGO antibody 2A10 comprises a heavy chain variable region having the amino acid sequence of SEQ ID NO: 37 and a light chain variable region having the amino acid sequence of SEQ ID NO: 40.

Anti-NOGO antibody 2C4 comprises a heavy chain variable region having the amino acid sequence of SEQ ID NO: 38 and a light chain variable region having the amino acid sequence of SEQ ID NO: 41.

Anti-NOGO antibody 15C3 comprises a heavy chain variable region having the amino acid sequence of SEQ ID NO: 39 and a light chain variable region having the amino acid sequence of SEQ ID NO: 42.

"NOGO" refers to any NOGO polypeptide, including variant forms. This includes, but is not limited to, NOGO-A having 1192 amino acid residues (GenBank accession no. AJ251383); NOGO-B, a splice variant which lacks residues 186 to 1004 in the putative extracellular domain (GenBank accession no. AJ251384) and a shorter splice variant, NOGO-C, which also lacks residues 186 to 1004 and also has smaller, alternative amino terminal domain (GenBank accession no. AJ251385) (Prinjha et al (2000) supra). All references to "NOGO" herein is understood to include any and all variant forms of NOGO such as NOGO-A and the splice variants described, unless a specific form is indicated.

"Neutralising" and grammatical variations thereof refers to inhibition, either total or partial, of NOGO function including its binding to neurones and inhibition of neurite growth.

"Altered antibody" refers to a protein encoded by an altered immunoglobulin coding region, which may be obtained by expression in a selected host cell. Such altered antibodies include engineered antibodies (e.g., chimeric, reshaped, humanized or vectored antibodies) or antibody fragments lacking all or part of an immunoglobulin constant region, e.g., Fv, Fab, or F(ab)2 and the like.

"Altered immunoglobulin coding region" refers to a nucleic acid sequence encoding altered antibody. When the altered antibody is a CDR-grafted or humanized antibody, the sequences that encode the complementarity determining regions (CDRs) from a non-human immunoglobulin are inserted into a first immunoglobulin partner comprising human variable framework sequences. Optionally, the first immunoglobulin partner is operatively linked to a second immunoglobulin partner.

"First immunoglobulin partner" refers to a nucleic acid sequence encoding a human framework or human immunoglobulin variable region in which the native (or naturally-occurring) CDR-encoding regions are replaced by the CDR-encoding regions of a donor antibody. The human variable region can be an immunoglobulin heavy chain, a light chain (or both chains), an analog or functional fragments thereof. Such CDR regions, located within the variable region of antibodies (immunoglobulins) can be determined by known methods in the art. For example Kabat et al. (Sequences of Proteins of Immunological Interest, 4 th Ed., U.S. Department of Health and Human Services, National Institutes of Health (1987)) disclose rules for locating CDRs. In addition, computer programs are known which are useful for identifying CDR regions/structures.

"Second immunoglobulin partner" refers to another nucleotide sequence encoding a protein or peptide to which the first immunoglobulin partner is fused in frame or by means of an optional conventional linker sequence (i.e., operatively linked). Preferably it is an immunoglobulin gene. The second immunoglobulin partner may include a nucleic acid sequence encoding the entire constant region for the same (i.e., homologous—the first and second altered antibodies are derived from the same source) or an additional (i.e., heterologous) antibody of interest. It may be an immunoglobulin heavy chain or light chain (or both chains as part of a single polypeptide). The second immunoglobulin partner is not limited to a particular immunoglobulin class or isotype. In addition, the second immunoglobulin partner may comprise part of an immunoglobulin constant region, such as found in a Fab, or F(ab)2 (i.e., a discrete part of an appropriate human constant region or framework region). Such second immunoglobulin partner may also comprise a sequence encoding an integral membrane protein exposed on the outer surface of a host cell, e.g., as part of a phage display library, or a sequence encoding a protein for analytical or diagnostic detection, e.g., horseradish peroxidase, β-galactosidase, etc.

The terms Fv, Fc, Fd, Fab, or F(ab)$_2$ are used with their standard meanings (see, e.g., Harlow et al., Antibodies A Laboratory Manual, Cold Spring Harbor Laboratory, (1988)).

As used herein, an "engineered antibody" describes a type of altered antibody, i.e., a full-length synthetic antibody (e.g., a chimeric, reshaped or humanized antibody as opposed to an antibody fragment) in which a portion of the light and/or heavy chain variable domains of a selected acceptor antibody are replaced by analogous parts from one or more donor antibodies which have specificity for the selected epitope. For example, such molecules may include antibodies characterized by a humanized heavy chain associated with an unmodified light chain (or chimeric light chain), or vice versa. Engineered antibodies may also be characterized by alteration of the nucleic acid sequences encoding the acceptor antibody light and/or heavy variable domain framework regions in order to retain donor antibody binding specificity. These antibodies can comprise replacement of one or more CDRs (preferably all) from the acceptor antibody with CDRs from a donor antibody described herein.

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., Queen et al., Proc. Natl Acad Sci USA, 86:10029-10032 (1989), Hodgson et al., Bio/Technology, 9:421 (1991)). A suitable human acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanised antibodies—see for example EP-A-0239400 and EP-A-054951

"Reshaped human antibody" refers to an altered antibody in which minimally at least one CDR from a first human monoclonal donor antibody is substituted for a CDR in a second human acceptor antibody. Preferably all six CDRs are replaced. More preferably an entire antigen combining region (e.g., Fv, Fab or F(ab')$_2$ ) from a first human donor monoclonal antibody is substituted for the corresponding region in a second human acceptor monoclonal antibody. Most preferrably the Fab region from a first human donor is operatively linked to the appropriate constant regions of a second human acceptor antibody to form a full length monoclonal antibody.

A "vectored antibody" refers to an antibody to which an agent has been attached to improve transport through the blood brain barrier (BBB). (Review see Pardridge; Advanced Drug Delivery Review 36, 299-321, 1999). The attachment may be chemical or alternatively the moiety can be engineered into the antibody. One example is to make a chimera with an antibody directed towards a brain capillary endothelial cell receptor e.g. an anti-insulin receptor antibody or anti-transferrin receptor antibody (Saito et al (1995) Proc. Natl. Acad. Sci. USA 92 10227-31; Pardridge et al (1995) Pharm. Res. 12 807-816; Broadwell et al (1996) Exp. Neurol. 142 47-65; Bickel et al (1993) Proc Natl. Acad. Sci. USA 90, 2618-2622; Friden et al (1996) J. Pharm. Exp. Ther. 278 1491-1498, U.S. Pat. No. 5,182,107, U.S. Pat. No. 5,154,924, U.S. Pat. No. 5,833,988, U.S. Pat. No. 5,527,527). Once bound to the receptor, both components of the bispecific antibody pass across the BBB by the process of transcytosis. Alternatively the agent may be a ligand which binds such cell surface receptors eg insulin, transferrin or low density lipoprotein (Descamps et al (1996) Am. J. Physiol. 270 H1149-H1158; Duffy et al (1 987) Brain Res. 420 32-38; Dehouck et al (1997) J. Cell Biol. 1997 877-889). Naturally occuring peptides such as penetratin and SynB1 and Syn B3 which are known to improve transport across the BBB can also be used (Rouselle et al (2000) Mol. Pharm. 57, 679-686 and Rouselle et al (2001) Journal of Pharmacology and Experimental Therapeutics 296, 124-131).

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal and/or recombinant) heterologous to the donor antibody, which contributes all (or any portion, but preferably all) of the amino acid sequences encoding its heavy and/or light chain framework regions and/or its heavy and/or light chain constant regions to the first immunoglobulin partner. Preferably a human antibody is the acceptor antibody.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883. For convenience the CDR's as defined by Kabat in SEQ ID Nos 37-42 are boxed.

CDRs provide the majority of contact residues for the binding of the antibody to the antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

A "functional fragment" is a partial heavy or light chain variable sequence (e.g., minor deletions at the amino or carboxy terminus of the immunoglobulin variable region) which retains the same antigen binding specificity and the same or similar neutralizing ability as the antibody from which the fragment was derived.

An "analog" is an amino acid sequence modified by at least one amino acid, wherein said modification can be chemical or a substitution or a rearrangement of a few amino acids (i.e., no more than 10), which modification permits the amino acid sequence to retain the biological characteristics, e.g., antigen specificity and high affinity, of the unmodified sequence. For example, (silent) mutations can be constructed, via substitutions, when certain endonuclease restriction sites are created within or surrounding CDR-encoding regions. The present invention contemplates the use of analogs of the antibody of the invention. It is well known that minor changes in amino acid or nucleic acid sequences may lead eg to an allelic form of the original protein which retains substantially similar properties. Thus analogs of the antibody of the invention includes those in which the CDRs in the hypervariable region of the heavy and light chains are at least 80% homologous, preferably at least 90% homologous and more preferably at least 95% homologous to the CDRs as defined above as CDRH1, CDRH2, CDRH3, CDRL1, CDRL2 and CDRL3 in tables 1 to 6 and retain NOGO neutralising activity. Amino acid sequences are at least 80% homologous if they have 80% identical amino acid residues in a like position when the sequences are aligned optimally, gaps or insertions being counted as non-identical residues. The invention also contemplates analogs of the antibodies of the invention wherein the framework regions are at least 80%, preferably at least 90% and more preferably at least 95% homologous to the framework regions set forth in SEQ ID NOs 37 to 42. Amino acid sequences are at least 80% homologous if they have 80% identical amino acid residues in a like position when the sequences are aligned optimally, gaps or insertions being counted as non-identical residues.

Analogs may also arise-as allelic variations. An "allelic variation or modification" is an alteration in the nucleic acid sequence. Such variations or modifications may be due to degeneracy in the genetic code or may be deliberately engineered to provide desired characteristics. These variations or modifications may or may not result in alterations in any encoded amino acid sequence.

The term "effector agents" refers to non-protein carrier molecules to which the altered antibodies, and/or natural or synthetic light or heavy chains of the donor antibody or other fragments of the donor antibody may be associated by conventional means. Such non-protein carriers can include conventional carriers used in the diagnostic field, e.g., polystyrene or other plastic beads, polysaccharides, e.g., as used in the BIAcore [Pharmacia] system, or other non-protein substances useful in the medical field and safe for administration to humans and animals. Other effector agents may include a macrocycle, for chelating a heavy metal atom, or radioisotopes. Such effector agents may also be useful to increase the half-life of the altered antibodies, e.g., polyethylene glycol.

Alternatively, one can construct antibodies, altered antibodies and fragments, by immunizing a non-human species (for example, bovine, ovine, monkey, chicken, rodent. (e.g., murine and rat), etc.) to generate a desirable immunoglobulin upon presentation with native NOGO from any species against which antibodies cross react with human NOGO can be generated, eg human or chicken. Conventional hybridoma techniques are employed to provide a hybridoma cell line secreting a non-human mAb to NOGO. Such hybridomas are then screened for binding using NOGO coated to 384- or 96-well plates, with biotinylated NOGO bound to a streptavidin coated plate or in a homogenous europium-APC linked immunoassay using biotinylated NOGO.

A native human antibody can be produced in a human antibody mouse such as the "Xenomouse™" (Abgenix) where the mouse immunoglobulin genes have been removed and genes encoding the human immunoglobulins have been inserted into the mouse chromosome. The mice are immunised as normal and develop an antibody reponse that is derived from the human genes. Thus the mouse produces human antibodies obviating the need to humanize the after selection of positive hybridomas. (See Green L. L., J Immunol Methods Dec. 10, 1999; 231(1-2):11-23).

The present invention also includes the use of Fab fragments or $F(ab')_2$ fragments derived from mAbs directed against NOGO. A Fab fragment contains the entire light chain and amino terminal portion of the heavy chain; and an $F(ab')_2$ fragment is the fragment formed by two Fab fragments bound by disulfide bonds. Fab fragments and, $F(ab')_2$ fragments can be obtained by conventional means, e.g., cleavage of mAb with the appropriate proteolytic enzymes, papain and/or pepsin, or by recombinant methods. The Fab and $F(ab')_2$ fragments are useful themselves as therapeutic or prophylactic, and as donors of sequences including the variable regions and CDR sequences useful in the formation of recombinant or humanized antibodies as described herein.

The Fab and $F(ab')_2$ fragments can also, be constructed via a combinatorial phage library (see, e.g., Winter et al., Ann. Rev. Immunol., 12:433-455 (1994)) or via immunoglobulin chain shuffling (see, e.g., Marks et al., Bio/Technology, 10:779-783 (1992), which are both hereby incorporated by reference in their entirety.

Thus human antibody fragments (Fv, scFv, Fab) specific for NOGO can be isolated using human antibody fragment phage display libraries. A library of bacteriophage particles, which display the human antibody fragment proteins, are panned against the NOGO protein. Those phage displaying antibody fragments that bind the NOGO are retained from the library and clonally amplified. The human antibody genes are then excised from the specific bacteriophage and inserted into human IgG expression constructs containing the human IgG constant regions to form the intact human IgG molecule with the variable regions from the isolated bacteriophage specific for NOGO.

The donor antibodies may contribute sequences, such as variable heavy and/or light chain peptide sequences, framework sequences, CDR'sequences, functional fragments, and analogs thereof, and the nucleic acid sequences encoding them, useful in designing and obtaining various altered antibodies which are characterized by the antigen binding specificity of the donor antibody.

Taking into account the degeneracy of the genetic code, various coding sequences may be constructed which encode the variable heavy and light chain amino acid sequences, and CDR sequences as well as functional fragments and analogs thereof which share the antigen specificity of the donor antibody. Isolated nucleic acid sequences, or fragments thereof, encoding the variable chain peptide sequences or CDRs can be used to produce altered antibodies, e.g., chimeric or humanized antibodies, or other engineered antibodies when operatively combined with a second immunoglobulin partner.

Altered immunoglobulin molecules can encode altered antibodies which include engineered antibodies such as chimeric antibodies and humanized antibodies. A desired altered immunoglobulin coding region contains CDR-encoding regions that encode peptides having the antigen specificity of an anti-NOGO antibody, preferably a high affinity antibody, inserted into a first immunoglobulin partner (a human framework or human immunoglobulin variable region).

Preferably, the first immunoglobulin partner is operatively linked to a second immunoglobulin partner. The second immunoglobulin partner is defined above, and may include a sequence encoding a second antibody region of interest, for example an Fc region. Second immunoglobulin partners may also include sequences encoding another immunoglobulin to which the light or heavy chain constant region is fused in frame or by means of a linker sequence. Engineered antibodies directed against functional fragments or analogs of NOGO may be designed to elicit enhanced binding.

The second immunoglobulin partner may also be associated with effector agents as defined above, including non-protein carrier molecules, to which the second immunoglobulin partner may be operatively linked by conventional means.

Fusion or linkage between the second immunoglobulin partners, e.g., antibody sequences, and the effector agent may be by any suitable means, e.g., by conventional covalent or ionic bonds, protein fusions, or hetero-bifunctional cross-linkers, e.g., carbodiimide, glutaraldehyde, and the like. Such techniques are known in the art and readily described in conventional chemistry and biochemistry texts.

Additionally, conventional linker sequences which simply provide for a desired amount of space between the second immunoglobulin partner and the effector agent may also be constructed into the altered immunoglobulin coding region. The design of such linkers is well known to those of skill in the art. In further aspects of the invention we provide diabodies (bivalent or bispecific), triabodies, tetrabodies and other multivalent scFV protein species having one or more CDRs as described supra that bind to and neutralise NOGO function.

In still a further embodiment, the antibody of the invention may have attached to it an additional agent. For example, the procedure of recombinant DNA technology may be used to produce an engineered antibody of the invention in which the Fc fragment or CH2-CH3 domain of a full length antibody molecule has been replaced by an enzyme or other detectable molecule (i.e., a polypeptide effector or reporter molecule).

The second immunoglobulin partner may also be operatively linked to a non-immunoglobulin peptide, protein or fragment thereof heterologous to the CDR-containing sequence having the antigen specificity of anti-NOGO antibody. The resulting protein may exhibit both anti-NOGO antigen specificity and characteristics of the non-immunoglobulin upon expression. That fusion partner characteristic may be, e.g., a functional characteristic such as another binding or receptor domain, or a therapeutic characteristic if the fusion partner is itself a therapeutic protein, or additional antigenic characteristics.

Another desirable protein of this invention may comprise a full length antibody molecule, having full length heavy and light chains, or any discrete fragment thereof, such as the Fab or F(ab')$_2$ fragments, a heavy chain dimer, or any minimal recombinant fragments thereof such as an Fv or a single-chain antibody (SCA) or any other molecule with the same specificity as the selected donor mAb. Such protein may be used in the form of an altered antibody, or may be used in its unfused form.

Whenever the second immunoglobulin partner is derived from an antibody different from the donor antibody, e.g. any isotype or class of immunoglobulin framework or constant regions, an engineered antibody results. Engineered antibodies can comprise immunoglobulin (Ig) constant regions and variable framework regions from one source, e.g., the acceptor antibody, and one or more (preferably all) CDRs from the donor antibody. In addition, alterations, e.g., deletions, substitutions, or additions, of the acceptor mAb light and/or heavy variable domain framework region at the nucleic acid or amino acid levels, or the donor CDR regions may be made in order to retain donor antibody antigen binding specificity.

Such engineered antibodies are designed to employ one (or both) of the variable heavy and/or light chains of the anti-NOGO mAb or one or more of the heavy or light chain CDRs. The engineered antibodies may be neutralising, as above defined.

Such engineered antibodies may include a humanized antibody containing the framework regions of a selected human immunoglobulin or subtype, or a chimeric antibody containing the human heavy and light chain constant regions fused to the anti-NOGO antibody functional fragments. A suitable human (or other animal) acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody.

Desirably the heterologous framework and constant regions are selected from human immunoglobulin classes and isotypes, such as IgG (subtypes 1 through 4), IgM, IgA, and IgE. However, the acceptor antibody need not comprise only human immunoglobulin protein sequences. For instance a gene may be constructed in which a DNA sequence encoding part of a human immunoglobulin chain is fused to a DNA sequence encoding a non-immunoglobulin amino acid sequence such as a polypeptide effector or reporter molecule.

Preferably, in a humanized antibody, the variable domains in both human heavy and light chains have been engineered by one or more CDR replacements. It is possible to use all six CDRs, or various combinations of less than the six CDRs. Preferably all six CDRs are replaced. It is possible to replace the CDRs only in the human heavy chain, using as light chain the unmodified light chain from the human acceptor antibody. Alternatively, a compatible light chain may be selected from another human antibody by recourse to the conventional antibody databases. The remainder of the engineered antibody may be derived from any suitable acceptor human immunoglobulin.

The engineered humanized antibody thus preferably has the structure of a natural human antibody or a fragment thereof, and possesses the combination of properties required for effective therapeutic use.

It will be understood by those skilled in the art that an engineered antibody may be further modified by changes in variable domain amino acids without necessarily affecting the specificity and high affinity of the donor antibody (i.e., an analog). It is anticipated that heavy and light chain amino acids may be substituted by other amino acids either in the variable domain frameworks or CDRs or both.

In addition, the constant region may be altered to enhance or decrease selective properties of the molecules of the instant invention. For example, dimerization, binding to Fc receptors, or the ability to bind and activate complement (see, e.g., Angal et al., Mol. Immunol, 30:105-108 (1993), Xu et al., J. Biol. Chem, 269:3469-3474 (1994), Winter et al., EP 307, 434-B).

An altered antibody which is a chimeric antibody differs from the humanized antibodies described above by providing the entire non-human donor antibody heavy chain and light chain variable regions, including framework regions, in association with immunoglobulin constant regions from other species, preferably human for both chains.

Preferably, the variable light and/or heavy chain sequences and the CDRs of suitable donor mAbs, and their encoding nucleic acid sequences, are utilized in the construction of altered antibodies, preferably humanized antibodies, of this invention, by the following process. The same or similar techniques may also be employed to generate other embodiments of this invention.

A hybridoma producing a selected donor mAb is conventionally cloned, and the DNA of its heavy and light chain variable regions obtained by techniques known to one of skill in the art, e.g., the techniques described in Sambrook et al., (Molecular Cloning (A Laboratory Manual), 2nd edition, Cold Spring Harbor Laboratory (1989)). The variable heavy and light regions containing at least the CDR-encoding regions and those portions of the acceptor mAb light and/or heavy variable domain framework regions required in order to retain donor mAb binding specificity, as well as the remaining immunoglobulin-derived parts of the antibody chain derived from a human immunoglobulin are obtained using polynucleotide primers and reverse transcriptase. The CDR-encoding regions are identified using a known database and by comparison to other antibodies.

A mouse/human chimeric antibody may then be prepared and assayed for binding ability. Such a chimeric antibody contains the entire non-human donor antibody VH and VL regions, in association with human Ig constant regions for both chains.

Homologous framework regions of a heavy chain variable region from a human antibody may be identified using computerized databases, e.g., KABAT®, and a human antibody having homology to the donor antibody will be selected as the acceptor antibody. A suitable light chain variable framework region can be designed in a similar manner.

A humanized antibody may be derived from the chimeric antibody, or preferably, made synthetically by inserting the donor mAb CDR-encoding regions from the heavy and light chains appropriately within the selected heavy and light chain framework. Alternatively, a humanized antibody can be made using standard mutagenesis techniques. Thus, the resulting humanized antibody contains human framework regions and donor mAb CDR-encoding regions. There may be subsequent manipulation of framework residues. The resulting humanized antibody can be expressed in recombinant host cells, e.g., COS, CHO or myeloma cells.

A conventional expression vector or recombinant plasmid is produced by placing these coding sequences for the antibody in operative association with conventional regulatory control sequences capable of controlling the replication and expression in, and/or secretion from, a host cell. Regulatory sequences include promoter sequences, e.g., CMV promoter, and signal sequences, which can be derived from other known antibodies. Similarly, a second expression vector can be produced having a DNA sequence which encodes a complementary antibody light or heavy chain. Preferably this second expression vector is identical to the first except insofar as the coding sequences and selectable markers are concerned, so to ensure as far as possible that each polypeptide chain is functionally expressed. Alternatively, the heavy and light chain coding sequences for the altered antibody may reside on a single vector.

A selected host cell is co-transfected by conventional techniques with both the first and second vectors (or simply transfected by a single vector) to create the transfected host cell of the invention comprising both the recombinant or synthetic light and heavy chains. The transfected cell is then cultured by conventional techniques to produce the engineered antibody of the invention. The antibody which includes the association of both the recombinant heavy chain and/or light chain is screened from culture by appropriate assay, such as ELISA or RIA. Similar conventional techniques may be employed to construct other altered antibodies and molecules.

Suitable vectors for the cloning and subcloning steps employed in the methods and construction of the compositions of this invention may be selected by one of skill in the art. For example, the conventional pUC series of cloning vectors may be used. One vector, pUC19, is commercially available from supply houses, such as Amersham (Buckinghamshire, United Kingdom) or Pharmacia (Uppsala, Sweden). Additionally, any vector which is capable of replicating readily, has an abundance of cloning sites and selectable genes (e.g., antibiotic resistance), and is easily manipulated may be used for cloning. Thus, the selection of the cloning vector is not a limiting factor in this invention.

Similarly, the vectors employed for expression of the antibodies may be selected by one of skill in the art from any conventional vector. The vectors also contain selected regulatory sequences (such as CMV or RSV promoters) which direct the replication and expression of heterologous DNA sequences in selected host cells. These vectors contain the above described DNA sequences which code for the antibody or altered immunoglobulin coding region. In addition, the vectors may incorporate the selected immunoglobulin sequences modified by the insertion of desirable restriction sites for ready manipulation.

The expression vectors may also be characterized by genes suitable for amplifying expression of the heterologous DNA sequences, e.g., the mammalian dihydrofolate reductase gene (DHFR). Other preferable vector sequences include a poly A signal sequence, such as from bovine growth hormone (BGH) and the betaglobin promoter sequence (betaglopro). The expression vectors useful herein may be synthesized by techniques well known to those skilled in this art.

The components of such vectors, e.g. replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast, and fungal expression may also be selected for this purpose.

The present invention also encompasses a cell line transfected with a recombinant plasmid containing the coding sequences of the antibodies or altered immunoglobulin molecules thereof. Host cells useful for the cloning and other manipulations of these cloning vectors are also conventional. However, most desirably, cells from various strains of *E. coli* are used for replication of the cloning vectors and other steps in the construction of altered antibodies of this invention.

Suitable host cells or cell lines for the expression of the antibody of the invention are preferably mammalian cells such as NS0, Sp2/0, CHO (e.g. DG44), COS, a fibroblast cell (e.g., 3T3), and myeloma cells, and more preferably a CHO or a myeloma cell. Human cells may be used, thus enabling the molecule to be modified with human glycosylation patterns. Alternatively, other eukaryotic cell lines may be employed. The selection of suitable mammalian host cells and methods for transformation, culture, amplification, screening and product production and purification are known in the art. See, e.g., Sambrook et al., cited above.

Bacterial cells may prove useful as host cells suitable for the expression of the recombinant Fabs of the present invention (see, e.g., Plückthun, A., Immunol. Rev., 130:151-188 (1992)). However, due to the tendency of proteins expressed in bacterial cells to be in an unfolded or improperly folded form or in a non-glycosylated form, any recombinant Fab produced in a bacterial cell would have to be screened for retention of antigen binding ability. If the molecule expressed by the bacterial cell was produced in a properly folded form, that bacterial cell would be a desirable host. For example, various strains of *E. coli* used for expression are well-known as host cells in the field of biotechnology. Various strains of *B. subtilis, Streptomyces*, other bacilli and the like may also be employed in this method.

Where desired, strains of yeast cells known to those skilled in the art are also available as host cells, as well as insect cells, e.g. Drosophila and Lepidoptera and viral expression systems. See, e.g. Miller et al., Genetic Engineering, 8:277-298, Plenum Press (1986) and references cited therein.

The general methods by which the vectors may be constructed, the transfection methods required to produce the host cells of the invention, and culture methods necessary to produce the antibody of the invention from such host cell are all conventional techniques. Typically, the culture method of the present invention is a serum-free culture method, usually by culturing cells serum-free in suspension. Likewise, once produced, the antibodies of the invention may be purified from the cell culture contents according to standard procedures of the art, including ammonium sulfate precipitation, affinity columns, column chromatography, gel electrophoresis and the like. Such techniques are within the skill of the art and do not limit this invention. For example, preparation of altered antibodies are described in WO 99/58679 and WO 96/16990.

Yet another method of expression of the antibodies may utilize expression in a transgenic animal, such as described in U.S. Pat. No. 4,873,316. This relates to an expression system using the animal's casein promoter which when transgenically incorporated into a mammal permits the female to produce the desired recombinant protein in its milk.

In a further aspect of the invention there is provided a method of producing an antibody of the invention which method comprises the step of culturing a host cell transformed or transfected with a vector encoding the light and/or heavy chain of the antibody of the invention and recovering the antibody thereby produced.

In accordance with the present invention there is provided a method of producing an anti-NOGO antibody which specifically binds to and neutralises the activity of human NOGO-A which method comprises the steps of;

(a) providing a first vector encoding a heavy chain of the antibody;
(b) providing a second vector encoding the light chain of the antibody;
(c) tranforming a mammalian host cell (e.g. CHO) with said first and second vectors;
(d) culturing the host cell of step (c) under conditions conducive to the secretion of the antibody from said host cell into said culture media;
(e) recovering the secreted antibody of step (d).

Once expressed by the desired method, the antibody is then examined for in vitro activity by use of an appropriate assay. Presently conventional ELISA assay formats are employed to assess qualitative and quantitative binding of the antibody to NOGO. Additionally, other in vitro assays may also be used to verify neutralizing efficacy prior to subsequent human clinical studies performed to evaluate the persistence of the antibody in the body despite the usual clearance mechanisms.

The therapeutic agents of this invention may be administered as a prophylactic or following the stroke event/on-set of clinical symptoms, or as otherwise needed. The dose and duration of treatment relates to the relative duration of the molecules of the present invention in the human circulation, and can be adjusted by one of skill in the art depending upon the condition being treated and the general health of the patient. It is envisaged that repeated dosing (e.g. once a week or once every two weeks) over an extended time period (e.g. four to six months) maybe required to achieve maximal therapeutic efficacy.

The mode of administration of the therapeutic agent of the invention may be any suitable route which delivers the agent to the host. The antagonists and antibodies, and pharmaceutical compositions of the invention are particularly useful for parenteral administration, i.e., subcutaneously, intrathecally, intraperitoneally, intramuscularly, intravenously, or intranasally, of which intravenously is particularly preferred.

Therapeutic agents of the invention may be prepared as pharmaceutical compositions containing an effective amount of the antagonist or antibody of the invention as an active ingredient in a pharmaceutically acceptable carrier. In the prophylactic agent of the invention, an aqueous suspension or solution containing the engineered antibody, preferably buffered at physiological pH, in a form ready for injection is preferred. The compositions for parenteral administration will commonly comprise a solution of the antagonist or antibody of the invention or a cocktail thereof dissolved in a pharmaceutically acceptable carrier, preferably an aqueous carrier. A variety of aqueous carriers may be employed, e.g., 0.9% saline, 0.3% glycine, and the like. These solutions are sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc. The concentration of the antagonist or antibody of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and between about 1 ng to about 100 mg, e.g. about 50 ng to about 30 mg or more preferably, about 5 mg to about 25 mg, of an antagonist or antibody of the invention. Similarly, a pharmaceutical composition of the invention for intravenous infusion could be made up to contain about 250 ml of sterile Ringer's solution, and about 1 to about 30 and preferably 5 mg to about 25 mg of an engineered antibody of the invention. Actual methods for preparing parenterally administrable compositions are well known or will be apparent to those skilled in the art and are described in more detail in, for example, Remington's Pharmaceutical Science, 15th ed., Mack Publishing Company, Easton, Pa. For the preparation of intravenously administrable antibody formulations of the invention see Lasmar U and Parkins D "The formulation of Biopharmaceutical products", Pharma. Sci. Tech. today, page 129-137, Vol. 3 ($3^{rd}$ April 2000), Wang, W "Instability, stabilisation and formulation of liquid protein pharmaceuticals", Int. J. Pharm 185 (1999) 129-188, Stability of Protein Pharmaceuticals Part A and B ed Ahem T. J., Manning M. C., New York, N.Y. Plenum Press (1992), Akers, M. J. "Excipient-Drug interactions in Parenteral Formulations", J. Pharm Sci 91 (2002) 2283-2300, Imamura, K et al "Effects of types of sugar on stabilization of Protein in the dried state", J Pharm Sci 92 (2003) 266-274, Izutsu, Kkojima, S. "Excipient crystalinity and its protein-structure-stabilizing effect during freeze-drying", J Pharm. Pharmacol, 54 (2002) 1033-1039, Johnson, R, "Mannitol-sucrose mixtures-versatile formulations for protein lyophilization", J. Pharm. Sci, 91 (2002) 914-922.

Ha, E Wang W, Wang Y. j. "Peroxide formation in polysorbate 80 and protein stability", J. Pharm Sci, 91, 2252-2264, (2002) the entire contents of which are incorporated herein by reference and to which the reader is specifically referred.

It is preferred that the therapeutic agent of the invention, when in a pharmaceutical preparation, be present in unit dose forms. The appropriate therapeutically effective dose can be determined readily by those of skill in the art. To effectively treat stroke and other neurological diseases in a human, one dose of up to 700 mg per 70 kg body weight of an antagonist or antibody of this invention should be administered parenterally, preferably i.v. or i.m. (intramuscularly). Such dose may, if necessary, be repeated at appropriate time intervals selected as appropriate by a physician. As disclosed in the examples, the present inventors have been able to demonstrate a positive effect on functional recovery in the rat model therein when antibodies of the invention were administered intravenously.

The antibodies described herein can be lyophilized for storage and reconstituted in a suitable carrier prior to use. This technique has been shown to be effective with conventional immunoglobulins and art-known lyophilization and reconstitution techniques can be employed.

Antibodies of the invention may also be used in combination (i.e. simultaneously, sequentially or separately) with a neurotrophic factor such as nerve growth factor (NGF), for example brain derived neurotrophic factor (BDNF), anti-inflammatory agents such as corticosteroids, and/or tPA. Combinations of a NOGO antibody of the invention and e.g. tPA maybe assessed in the MCAO model set forth in the examples below.

In another aspect, the invention provides a pharmaceutical composition comprising anti-NOGO antibody of the present invention or a functional fragment thereof and a pharmaceutically acceptable carrier for treatment or prophylaxis of stroke and other neurological diseases.

In a yet further aspect, the invention provides a pharmaceutical composition comprising the anti-NOGO antibody of the present invention or a functional fragment thereof and a pharmaceutically acceptable carrier for inhibiting neurodegeneration and/or promoting functional recovery in a human patient suffering, or at risk of developing, a stroke or other neurological disease.

The invention further provides a method of treatment or prophylaxis of stroke (particularly ischemic stroke) and other neurological diseases/disorders, in particular Alzheimer's disease, in a human which comprises administering to said human in need thereof an effective amount of an anti-NOGO antibody or a functional fragment thereof. Antibodies of the invention may be used in methods of treatment to slow or halt the progression and/or onset of Alzheimer's disease in addition to (or as an alternative to) treating established disease in a human patient.

Further the invention provides the use of an anti-NOGO antibody, or a functional fragment thereof, in the preparation of a medicament for treatment or prophylaxis of stroke and other neurological diseases/disorders, in particular Alzheimer's disease.

The invention also provides a method of inhibiting neurodegeneration and/or promoting functional recovery in a human patient suffering, or at risk of developing, a stroke or other neurological disease/disorder, in particular Alzheimer's disease, which comprises administering to said human in need thereof an effective amount of an anti-NOGO antibody or a functional fragment thereof.

In addition the invention provides the use of an anti-NOGO antibody or a functional fragment thereof in the preparation of a medicament for inhibiting neurodegeneration and/or promoting functional recovery in a human patient afflicted with, or at risk of developing, a stroke and other neurological disease/disorder, in particular Alzheimer's disease.

The invention further provides a method of treating or prophylaxis of stroke or other neurological disease/disorder, in particular Alzheimer's disease, in a human comprising the step of parenteral administration of a therapeutically effective amount of an anti-NOGO antibody. Preferably the anti-NOGO antibody is administered intravenously.

Neurological diseases or disorders as used hereinabove includes, but is not limited to traumatic brain injury, spinal cord injury, fronto-temporal dementias (tauopathies), peripheral neuropathy, Parkinson's disease, Huntington's disease, multiple sclerosis and in particular Alzheimer's disease.

The invention also provides a method of promoting axonal sprouting comprising the step of contacting a human axon with an anti-NOGO antibody. This method may be performed in-vitro or in-vivo, preferably the method is performed in-vivo.

In a further aspect therefore there is provided the use of an anti-NOGO antibody or functional fragment thereof of the invention comprising CDR's of table 1 and 2; CDR's of Table 3 and 4; or CDR's of table 5 and 6 in intravenously administrable form in the manufacture of a medicament for the treatment of stroke (particularly ischemic stroke), brain injury, spinal cord injury, fronto-temporal dementias (tauopathies), peripheral neuropathy, Parkinson's disease, Huntington's disease, multiple sclerosis and in particular Alzheimer's disease in a human patient.

In a further aspect therefore there is provided a method of treating stroke (particularly ischemic stroke), brain injury, spinal cord injury, fronto-temporal dementias (tauopathies), peripheral neuropathy, Parkinson's disease, Huntington's disease, multiple sclerosis and in particular Alzheimer's disease in a human patient which method comprises the intravenous administration of a therapeutically effective amount of an anti-NOGO antibody of the invention.

In a further aspect of the present invention there is provided a method of promoting axon sprouting of neurons within the central nervous system of a human subject (e.g. patient) which method comprises administering (e.g. intravenously administering) a therapeutically effective amount of an anti-NOGO antibody (e.g. an anti-NOGO antibody comprising CDRs as set forth herein).

In a further aspect of the present invention there is provided the use of an anti-NOGO antibody (e.g. an anti-NOGO antibody comprising the CDRs set forth herein) in the manufacture of an intravenously administrable medicament for the treatment of stroke (particularly ischemic stroke), brain injury, spinal cord injury, fronto-temporal dementias (tauopathies), peripheral neuropathy, Parkinson's disease, Huntington's disease, multiple sclerosis and in particular Alzheimer's disease in a human patient.

In a further aspect of the invention there is provided a method of regenerating axon processes in neurons of the central nervous system in a human patient afflicted with (or susceptible to) stroke (particularly ischemic stroke), brain injury, spinal cord injury, fronto-temporal dementias (tauopathies), peripheral neuropathy, Parkinson's disease, Huntington's disease, multiple sclerosis and in particular Alzheimer's disease which method comprises the step of administering (e.g. intravenously) a therapeutically effective amount of an anti-NOGO antibody (e.g. an anti-NOGO antibody having the CDRs set forth herein).

In a further aspect of the invention there is provided the use of an anti-NOGO antibody (e.g. an anti-NOGO antibody having the CDRs set forth herein) in the manufacture of an intravenously administrable pharmaceutical composition for regenerating axon processes in neurons of the central nervous system in a human patient afflicted with (or susceptible to) stroke (particularly ischemic stroke), brain injury, spinal cord injury, fronto-temporal dementias (tauopathies), peripheral neuropathy, Parkinson's disease, Huntington's disease, multiple sclerosis and in particular Alzheimer's disease.

In a further aspect of the invention there is provided a method of modulating the production of an amyloidogenic peptide comprising contacting a cell which is expressing the precursor from which the amyloidogenic peptide is derived and a NOGO polypeptide (e.g. human NOGO-A) with an anti-NOGO antibody (e.g. an anti-NOGO antibody comprising the CDRs set forth herein, particularly 2A10 and fully human or humanised versions thereof). In typical embodiments, the precursor is APP. In further typical embodiments the amyloidogenic peptide is Aβ, most preferably Aβ40, Aβ42 or a combination of both.

As used herein, the term "functional recovery" refers to a motor and/or sensory and/or behavioural improvement in a subject following e.g. an ischemic event or injury or on-set of clinical symptoms. Functional recovery in humans may be evaluated by instruments designed to measure elemental neurological functions such as motor strength, sensation and coordination, cognitive functions such as memory, language and the ability to follow directions, and functional capacities such as basic activities of daily living or instrumental activities. Recovery of elemental neurological function can be measured with instruments such as the NIH Stroke Scale (NIHSS), recovery of cognitive function can be measured with neuropsychological tests such as Boston Naming Test, Trail-making Tests, and California Verbal Learning Test, and activities of daily living may be measured with instruments such as the ADCS/ADL (Alzheimer's Disease Clinical Studies/Activities of Daily Living) scale or the Bristol Activities of Daily Living Scale, all tests and scales known in the art.

The following examples illustrate but do not limit the invention.

Exemplification.

EXAMPLE 1

Preparation and Selection of the Hybridomas

Anti-NOGO monoclonal antibodies are produced by hybridoma cells, the result of the fusion of mouse myeloma cells with B lymphocytes from mice immunised with the target antigen. The hybridoma cell is immortalised by the myeloma fusion partner while the capacity to produce antibodies is provided by the B lymphocyte. Each hybridoma cell makes only one individual antibody with unique specificity hence the term monoclonal.

SJL mice were immunised with 10 μg total protein (1:1, human NOGO-A splice (amino acids 186-1004) and rat NOGO-A splice (amino acids 173-975), produced as GST-fusion proteins in E.Coli BL21) using both CFA and RIBI adjuvants subcutaneously. The mice were then boosted with 5 μg of the same proteins using RIBI adjuvant after 4 and 8 days. After a further 3 days, immune cells were harvested from the locally draining lymph nodes and fused with mouse myeloma cells using PEG1500 to generate hybridomas. Individual hybridoma cell lines were cloned by two rounds of limiting dilution. By immunising the mice with both human and rat NOGO-A, antibodies may be raised that have good binding specificity and/or binding affinity for both rat as well as human NOGO-A. This in turn enables evaluation of such antibodies in rat and/or rodent models prior to administration to a human.

Initial hybridoma antibody selection was on the basis of direct binding to the NOGO protein(s) on microtitre plates. Subsequently approximately 60 hybridomas were selected based on the ability of soluble protein (consisting of human NOGO-A sequence cleaved from the GST moiety using Prescission™ protease) to compete for this binding activity in ELISA assays.

EXAMPLE 2

Cloning of the Variable Regions

Total RNA was extracted from the selected 2A10/3, 2C4/1 and 1 5C3/3 hybridoma cells followed by reverse transcription and polymerase chain reaction (RT-PCR) to extract heavy and light variable-domain cDNA sequence,. The forward primer for RT-PCR was a mixture of degenerate primers specific for murine immunoglobulin gene leader-sequences and the reverse primer was an isotype-specific antibody directed to the constant regions. PCR primers were designed to carry 5' restriction enzyme recognition sites to enable cloning into pUC19 for DNA sequencing.

RNA Extraction

Total RNA was extracted from pellets of $10^6$ cells of each hybridoma clone using the SV Total RNA Isolation System from Promega according to manufacturer's instructions.

Reverse Transcription

RNA was reverse transcribed to produce cDNA of the variable heavy and light domains using forward primers specific for the murine leader sequences and reverse primers to murine IgGκ constant regions. The IgGγ1 reverse primer was used for hybridomas 2C4/1 and 15C3/3; and the IgGγ2b for 2A10/3. Forward primers carry a SalI restriction enzyme recognition site at the 5' end, with four extra nucleotides added 5' to this for efficient restriction digestion. These primers were adapted from Jones S T and Bendig M M 1991 (Biotechnology 9, 88-89). Reverse primers carry a XmaI restriction enzyme recognition site plus and extra four nucleotides at the 5' ends.

Primers:

Murine $V_H$ Leader Sequence Forward Primers:

AG77:
(SEQ.I.D.NO:51)
5'-ACT AGT CGA CAT GAA ATG CAG CTG GGT CAT STT CTT C-3'

AG78:
(SEQ.I.D.NO:52)
5'-ACT AGT CGA CAT GGG ATG GAG CTR TAT CAT SYT CTT-3'

AG79:
(SEQ.I.D.NO:53)
5'-ACT AGT CGA CAT GAA GWT GTG GTT AAA CTG GGT TTT T-3'

AG80:
(SEQ.I.D.NO:54)
5'-ACT AGT CGA CAT GRA CTT TGG GYT CAG CTT GRT TT-3'

AG81:
(SEQ.I.D.NO:55)
5'-ACT AGT CGA CAT GGA CTC CAG GCT CAA TTT AGT TTT CCT T-3'

AG82:
(SEQ.I.D.NO:56)
5'-ACT AGT CGA CAT GGC TGT CYT RGS GCT RCT CTT CTG C-3'

AG83:
(SEQ.I.D.NO:57)
5'-ACT AGT CGA CAT GGR ATG GAG CKG GRT CTT TMT CTT-3'

AG84:
(SEQ.I.D.NO:58)
5'-ACT AGT CGA CAT GAG AGT GCT GAT TCT TTT GTG-3'

AG85:
(SEQ.I.D.NO:59)
5'-ACT AGT CGA CAT GGM TTG GGT GTG GAM CTT GCT ATT CCT G-3'

AG86:
(SEQ.I.D.NO:60)
5'-ACT AGT CGA CAT GGG CAG ACT TAC ATT CTC ATT CCT G-3'

AG87:
(SEQ.I.D.NO:61)
5'-ACT AGT CGA CAT GGA TTT TGG GCT GAT TTT TTT TAT TG-3'

AG89:
(SEQ.I.D.NO:62)
5'-ACT AGT CGA CAT GAT GGT GTT AAG TCT TCT GTA CCT G-3'

Murine $V_L$ Leader Sequence Forward Primers:

AG90:
(SEQ.I.D.NO:63)
5'-ACT AGT CGA CAT GAA GTT GCC TGT TAG GCT GTT GGT GCT G-3'

AG91:
(SEQ.I.D.NO:64)
5'-ACT AGT CGA CAT GGA GWC AGA CAC ACT CCT GYT ATG GGT-3'

AG92:
(SEQ.I.D.NO:65)
5'-ACT AGT CGA CAT GAG TGT GCT CAC TCA GGT CCT GGC GTT G-3'

AG93:
(SEQ.I.D.NO:66)
5'-ACT AGT CGA CAT GAG GRC CCC TGC TCA GWT TYT TGG MWT CTT G-3'

AG94:
(SEQ.I.D.NO:67)
5'-ACT AGT CGA CAT GGA TTT WCA GGT GCA GAT TWT CAG CTT C-3'

AG95:
(SEQ.I.D.NO:68)
5'-ACT AGT CGA CAT GAG GTK CYY TGY TSA GYT YCT GRG G-3'

AG96:
(SEQ.I.D.NO:69)
5'-ACT AGT CGA CAT GGG CWT CAA GAT GGA GTC ACA KWY YCW GG-3'

AG97:
(SEQ.I.D.NO:70)
5'-ACT AGT CGA CAT GTG GGG AYC TKT TTY CMM TTT TTC AAT TG-3'

AG98:
(SEQ.I.D.NO:71)
5'-ACT AGT CGA CAT GGT RTC CWC ASC TCA GTT CCT TG-3'

AG99:
(SEQ.I.D.NO:72)
5'-ACT AGT CGA CAT GTA TAT ATG TTT GTT GTC TAT TTC T-3'

AG100:
(SEQ.I.D.NO:73)
5'-ACT AGT CGA CAT GGA AGC CCC AGC TCA GCT TCT CC-3'

MKV12:
(SEQ.I.D.NO:74)
5'-ACT AGT CGA CAT GAA GTT TCC TTC TCA ACT TCT GCT C-3'

Murine γ1 Constant Region Reverse Primer:

AG102:
(SEQ.I.D.NO:75)
5'-GGA TCC CGG GCC AGT GGA TAG ACA GAT G-3'

Murine γ2b Constant Region Reverse Primer:

AG104:
(SEQ.I.D.NO:76)
5'-GGA TCC CGG GAG TGG ATA GAC TGA TGG-3'

Murine κ Constant Region Reverse Primer:

AG101:
(SEQ.I.D.NO:77)
5'-GGA TCC CGG GTG GAT GGT GGG AAG ATG-3'

Pools of murine $V_H$ or $V_L$ leader sequence forward primers were prepared at 50 μM. Solutions of the murine γ or κ constant region reverse primers were also prepared at 50 μM.

Reverse Transcriptase PCR (RT-PCR).

Reverse transcription of the RNA encoding the variable heavy and light regions was carried out in duplicate using the Access RT-PCR System from Promega according to manufacturer's instructions. Approximately 200 ng RNA was included in a 50 μl reaction containing RT-PCR buffer supplied, 0.2 mM dNTPs, 1 μM of each primer set, 1 μM MgSO4 and 5U each of AMV Reverse transcriptase and Tfl DNA polymerase.

RT-PCR cycle: 1-48° C. for 45 min
2-94° C. for 2 min
3-94° C. for 30 sec
4-50° C. for 1 min
5-68° C. for 2 min
6-68° C. for 7 min
steps 3 to 5: repeat 30 times.

pUC19 Cloning

The variable region RT-PCR products were purified using a Qiagen MinElute Qiagen PCR Purifcation kit according to their instructions and digested sequentially with XmaI and SalI from New England Biolabs according to manufacture's instructions. They were then loaded on a preparative 1% agarose gel containing 0.5% ethidium bromide and run in TAE buffer at 50 mA for 1 hour and the V region bands excised under ultra-violet light. The DNA fragments were purified from the gel using the MinElute Gel extraction kit from Qiagen according to manufacturers instructions. pUC19 vector arms were prepared by digesting pUC19 with SalI and XmaI, then purified using the MinElute Reaction Clean up kit from Qiagen and dephosphorylated using Shrimp alkaline phosphatase (USB) according to the manufacturer's instructions. The concentration of the vector arms and the V-region fragments was estimated from an analytical 1% agarose/ ethidium bromide gel, mixed in a molar ratio of 1:2 and ligated using Promega's Quick Ligation kit acording to the manufacturer's instructions. Ligated plasmids were transformed into DH5α cells (Invitrogen) according manufacturer's instructions. Colonies which grew on L-agar plates containing 100 µg/ml ampicillin were selected for DNA sequence analysis.

Variable Region Sequencing

Colonies were cultured overnight at 37° C. in 5 ml LB medium supplemented with 100 µg/ml ampicillin and plasmid DNA was extracted and purified using the Qiagen QIAprep Spin Miniprep kit according to manufacturer's instructions. The $V_H$ and $V_L$ regions were DNA sequenced using standard M13 forward and reverse primers.

The results of the sequencing determination are shown as SEQ ID NOs 43 to 48.

EXAMPLE 3

Recombinant Anti-NOGO Antibodies

Recombinant antibodies having murine 2a/k constant regions could be purified from cells transfected with plasmids comprising the light and heavy variable regions cloned onto mouse IgG2a/k constant region gene segments. The cloned murine V regions were amplified by PCR to introduce restriction sites required for cloning into mammalian expression vectors RId and RIn. Hind III and Spe I sites were designed in, frame with the $V_H$ domain to allow cloning into a modified RId vector containing the mouse γ2a constant region. Hind III and BsiW I sites were designed in frame the $V_L$ domain and allow cloning into a modified RIn vector containing the mouse κ constant region.

PCR Primers

2A10 $V_H$ Forward Primer:

(SEQ.ID.NO:78)
5'-ACTCATAAGCTTGCCACCATGGGATGGAGCTGTATCATCCTCTTTTT
GGTAG-3'

$V_H$ Reverse Primer:

(SEQ.I.D.NO:79)
5'-ACTATGACTAGTGTGCCTTGGCCCCAGTAG-3'

$V_L$ Forward Primer:

(SEQ.I.D.NO:80)
5'-ACTCATAAGCTTGCCACCATGAGGTGCTCTCTTCAGTTTCTG-3'

$V_L$ Reverse Primer:

(SEQ.I.D.NO:81)
5'-ACTATGCGTACGTTTCAGCTCCAGCTTGG-3'

PCR was performed using Hercules (Stratagene) according to the manufacturer's instructions in 50 µl volume containing approx 10 ng of the pUC19 miniprep containing the V-region, 2% DMSO, 400 µM dNTPs, 1 µM each primer and buffer supplied. PCR was carried out as follows 1-95° C. 2 mins, 2-95° C. 1 min, 3-56° C. 1 min, 4-72° C. 1 min. Steps 2-4 30 cycles.

Cloning Into Expression Vectors

The PCR products were purified using the MinElute PCR Purification kit from Qiagen according to manufacturers instructions. The $V_H$ PCR product and RId (IgG2a) mammalian expression vector were digested Hind III-Spe I. The $V_L$ PCR product and RIn (k) mammalian expression vector were digested Hind III-BsiW I (NEB) according to manufacturer's instructions. Vectors were ligated to inserts in a 1:2 molar ratio using the Promega Quick Ligation kit. Ligation mixes were transfected into DH5α cells and colonies growing on ampicillin selection were grown up and sent for DNA sequence verification.

Sequencing of Recombinant Anti-NOGO Antibody 2A10/3

The sequence of the 2A10 heavy chain between the HindIII and EcoRI cloning sites was determined to be:

(SEQ ID NO:49)
AAGCTTGCCACCATGGGATGGAGCTGTATCATCCTCTTTTTGGTAGCAGC

AGCTACAGGTGTCCACTCCCAGGTCCAACTGCAGCAGCCTGGGACTGAAC

TGGTGAAGCCTGGGGCTTCAGTGAAGCTGTCCTGCAAGGCTTCTGGCTAC

ACCTTCACCAGCTACTGGATGCACTGGGTGAAGCAGAGGCCTGGACAAGG

CCTTGAGTGGATTGGAAATATTAATCCTAGCAATGGTGGTACTAACTACA

ATGAGAAGTTCAAGAGCAAGGCCACACTGACTGTAGACAAATCCTCCAGC

ACAGCCTACATGCAGCTCAGCAGCCTGACATCTGAGGACTCTGCGGTCTA

TTATTGTGAACTGGGACAGGGCTACTGGGGCCAAGGCACACTAGTCACCG

TCTCCTCAGCCAAAACAACAGCCCCATCGGTCTATCCACTGGCCCCTGTG

TGTGGAGATACAACTGGCTCCTCGGTGACTCTAGGATGCCTGGTCAAGGG

TTATTTCCCTGAGCCAGTGACCTTGACCTGGAACTCTGGATCCCTGTCCA

GTGGTGTGCACACCTTCCCAGCTGTCCTGCAGTCTGACCTCTACACCCTC

AGCAGCTCAGTGACTGTAACCTCGAGCACCTGGCCCAGCCAGTCCATCAC

CTGCAATGTGGCCCACCCGGCAAGCAGCACCAAGGTGGACAAGAAATTG

AGCCCAGAGGGCCCACAATCAAGCCCTGTCCTCCATGCAAATGCCCAGCA

CCTAACCTCCTGGGTGGCCCATCCGTCTTCATCTTCCCTCCAAAGATCAA

GGATGTACTCATGATCTCCCTGAGCCCCATAGTCACATGTGTGGTGGTGG

ATGTGAGCGAGGATGACCCAGATGTCCAGATCAGCTGGTTTGTGAACAAC

GTGGAAGTACACACAGCTCAGACACAAACCCATAGAGAGGATTACAACAG

TACTCTCCGGGTGGTCAGTGCCCTCCCCATCCAGCACCAGGACTGGATGA

GTGGCAAGGAGTTCAAATGCAAGGTCAACAACAAAGACCTCCCAGCGCCC

ATCGAGAGAACCATCTCAAAACCCAAAGGGTCAGTAAGAGCTCCACAGGT

ATATGTCTTGCCTCCACCAGAAGAAGAGATGACTAAGAAACAGGTCACTC

TGACCTGCATGGTCACAGACTTCATGCCTGAAGACATTTACGTGGAGTGG

ACCAACAACGGGAAAACAGAGCTAAACTACAAGAACACTGAACCAGTCCT

GGACTCTGATGGTTCTTACTTCATGTACAGCAAGCTGAGAGTGGAAAAGA

AGAACTGGGTGGAAAGAAATAGCTACTCCTGTTCAGTGGTCCACGAGGGT

CTGCACAATCACCACACGACTAAGAGCTTCTCCCGGACTCCGGGTAAATG

AGAATTC

The sequence of the 2A10 light chain between the HindIII and EcoRI cloning sites was determined to be:

(SEQ ID NO: 50)
```
AAGCTTGCCACCATGAGGTGCTCTCTTCAGTTTCTGGGGGTGCTTATGTT
CTGGATCTCTGGAGTCAGTGGGGATATTGTGATAACCCAGGATGAACTCT
CCAATCCTGTCACTTCTGGAGAATCAGTTTCCATCTCCTGCAGGTCTAGT
AAGAGTCTCCTATATAAGGATGGGAAGACATACTTGAATTGGTTTCTGCA
GAGACCAGGACAATCTCCTCAGCTCCTGATCTATTTGATGTCCACCCGTG
CATCAGGAGTCTCAGACCGGTTTAGTGGCAGTGGGTCAGGAACAGATTTC
ACCCTGGAAATCAGTAGAGTGAAGGCTGAGGATGTGGGTGTGTATTACTG
TCAACAACTTGTAGAGTATCCGCTCACGTTCGGTGCTGGGACCAAGCTGG
AGCTGAAACGTACGGATGCTGCACCGACTGTATCCATCTTCCCACCATCC
AGTGAGCAGTTAACATCTGGAGGTGCCTCAGTCGTGTGCTTCTTGAACAA
CTTCTACCCCAAAGACATCAATGTCAAGTGGAAGATTGATGGCAGTGAAC
GACAAAATGGCGTCCTGAACAGTTGGACTGATCAGGACAGCAAAGACAGC
ACCTACAGCATGAGCAGCACCCTCACGTTGACCAAGGACGAGTATGAACG
ACATAACAGCTATACCTGTGAGGCCACTCACAAGACATCAACTTCACCCA
TTGTCAAGAGCTTCAACAGGAATGAGTGTTAAGAATTC
```

A chimaera of 2A10 was also constructed as is referred to herein as HcLc.

EXAMPLE 4

Mouse Anti-NOGO Antibody Binds to NOGO

GST-human NOGO-A56 at 5 µg/ml in 50 mM Tris pH9.5 was coated onto Nunc Immunosorp plates (100 µl per well) at 4° C. overnight. Wells were rinsed once with PBS then incubated with 1% BSA in PBS to block non-specific binding sites at room temperature for 1 hour. Antibodies were diluted in PBS to 2 µg/ml and ⅓ dilutions made from this. Antibodies were added to wells in triplicate and incubated at 4 C overnight. Wells were washed three times with PBS then incubated with Anti-Mouse-HRP (1:1000) for 1 hour. Washed five times with PBS and then incubated with 100 µl TMB substrate (Sigma) per well for 10 minutes. The colour reaction was stopped by the addition of 50 µl concentrated HCl. Optical density at 450 nm was measured using a plate reader. Background values read from wells with no antibody were subtracted.

FIG. 8 shows the dose-dependent binding of all three mouse anti-NOGO-A monoclonal antibodies, 2A10, 2C4 and 15C3, to human NOGO-A56 in an ELISA assay.

The Y-axis shows the measured optical density (OD) at 450 nm, a quantitative measure of antibody captured in the wells. The X-axis shows the concentration of antibody used (ng/ml) per well at each data point. Antibody 2A10 shows the highest signal at a range of concentrations suggestive of a higher affinity for human NOGO-A.

EXAMPLE 5

Production of Inhibitory NOGO-A Fragment (NOGO-A56, SEQ.I.D.NO:87)

A cDNA sequence encoding amino acids 586-785 (MQESLYPAAQLCPSFEESEATPSPVLP-DIVMEAPLNSAVPSAGASVIQPSSSPLEASSV NYESIKHEPENPPPYEEAMSVSLKKVS-GIKEEIKEPENINAALQETEAPYISIACDLIKE TKL-SAEPAPDFSDYSEMAKVEQPVPDH-SELVEDSSPDSEPVDLFSDDSIPDVPQKQDETV MLVKESLTETSFESMIEYENKE—SEQ.I.D.NO:87) of human NOGO-A was cloned into the BamHI-XhoI sites of pGEX-6P1 to generate a GST-tagged fusion protein designated NOGO-A56. Plasmid was expressed in BL21 cells in 2XTY medium with 100 µg/ml ampicillin following induction with IPTG to 0.5 mM at 37 C for 3 hours. Cell pellets were lysed by sonication and the fusion protein purified using Glutathione-sepharose (Amersham Pharmacia) following manufacturers instructions. Purified protein was eluted using reduced glutathione and extensively dialysed against PBS, quantitated using BSA standards and a BioRad coomassie based protein assay and then stored in aliquots at −80 C. Thus the present invention provides an antibody or functional fragment thereof which binds to NOGO-A, particularly human NOGO-A wherein said antibody or functional fragment thereof neutralises the activity of a NOGO protein comprising the polypeptide encoded by SEQ.I.D.NO:87 wherein said antibody binds to SEQ.I.D.NO:87 of said protein. In typical forms, antibodies of the invention bind between amino acids 586-785 of human NOGO-A and neutralise the activity of NOGO-A.

EXAMPLE 6

Neurite-Outgrowth Assay

Control GST only or GST-NOGOA56 fusion proteins were thawed on ice and diluted in 0.5× tissue culture grade PBS to 3 pmol/µl. 5 µl spots were dried onto the centre of each well of BD-Biocoat poly-d-lysine coated 96 well plates in the tissue-culture cabinet. Once dried, purified antibodies, hybridoma conditioned tissue-culture supernatant or compounds were diluted in HBSS (Life Technologies) and 50 µl applied to wells in replicates of between 4 and 8 wells. Control wells of GST alone and GST-NOGO-A56 were treated with HBSS without supplements. After 2 hours pretreatment at 37 C purified, dissociated cerebellar granule neurons from postnatal day 8 rat brains were added at 20-40,000 neurons per well in a volume of 100 µl and incubated at 37 C for 24 hours. Cultures were fixed using 4% paraformaldehyde/10% sucrose in PBS for 1 hour then neurites were stained using a polyclonal anti-beta-III-tubulin antibody.

Neurite-outgrowth was quantitated using automated image capture and analysis on the Cellomics Arrayscan system.

The results are shown in FIGS. 1 to 6.

Figure 1:
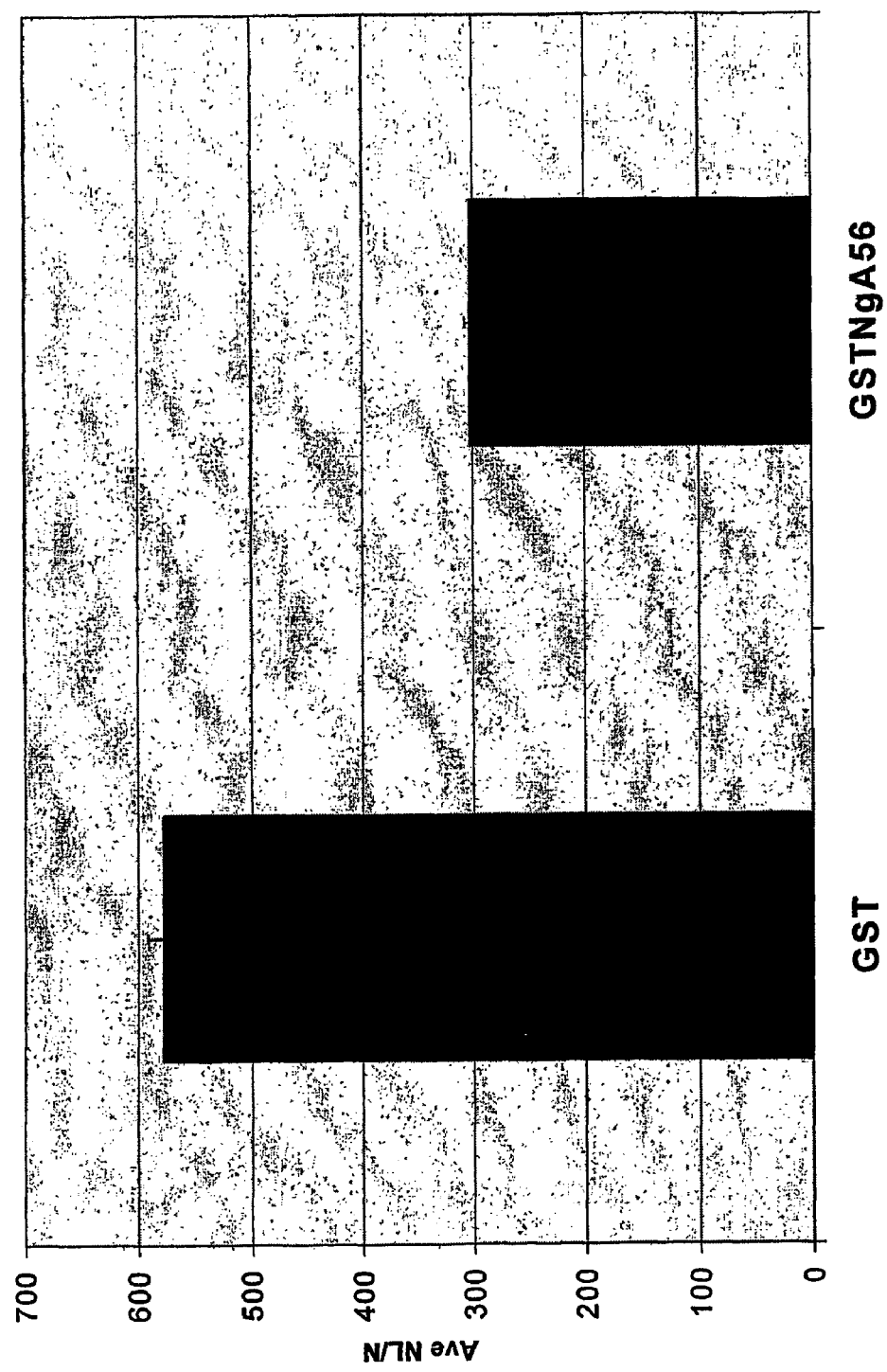
FIG. 1 shows the inhibitory effect of the GST-NOGO-A56 fusion protein on neurite outgrowth. The Y axis shows the average neurite length/neurite (NL/N) in arbitrary units.
Figure 2:
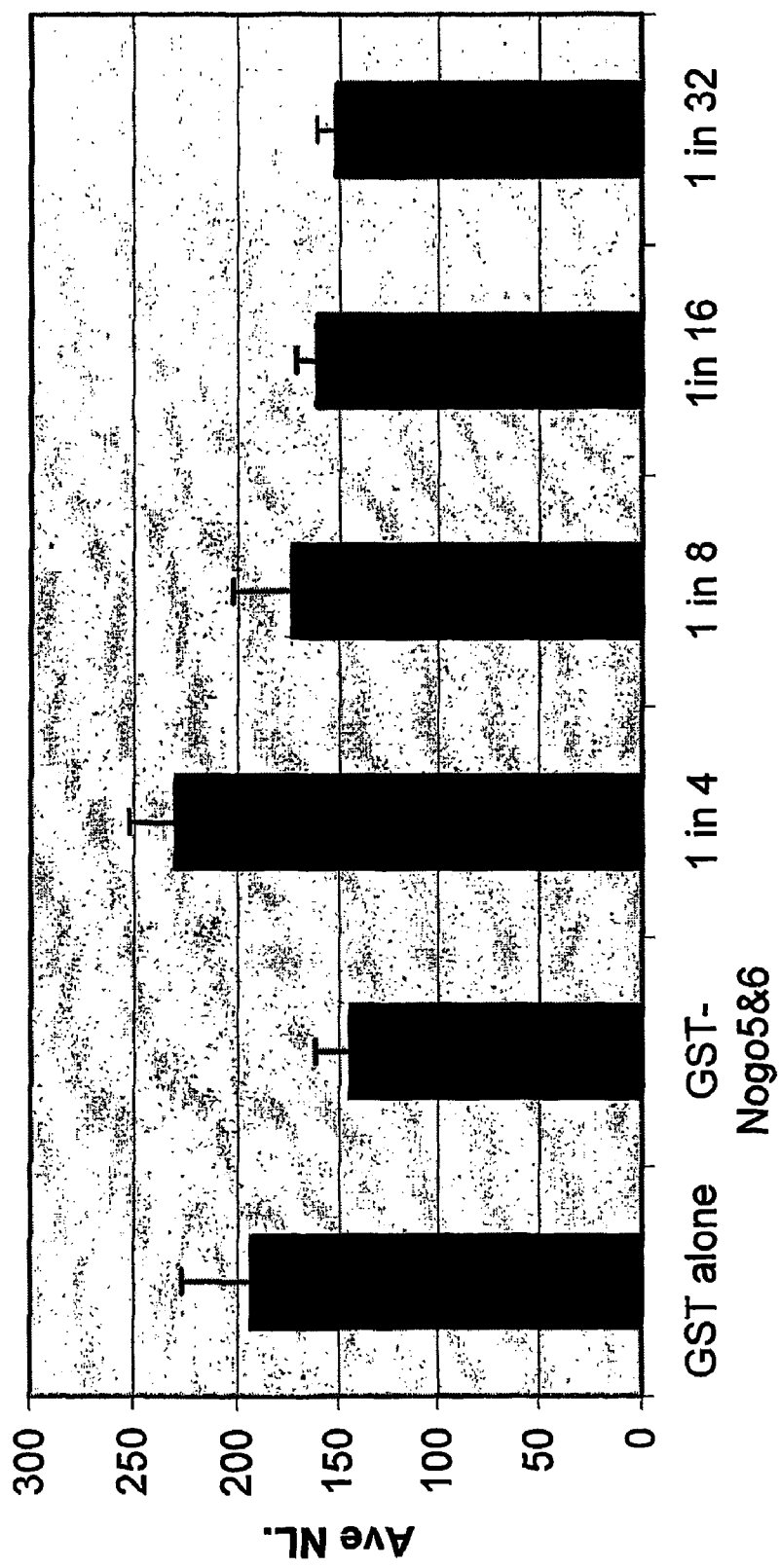
FIG. 2 shows the blocking effect by the supernatant of the hybridoma 2A10 on the neurite outgrowth inhibitory activity of NOGO-A56 (GST-Nogo5&6). The Y axis is as for FIG. 1.
Figure 3:
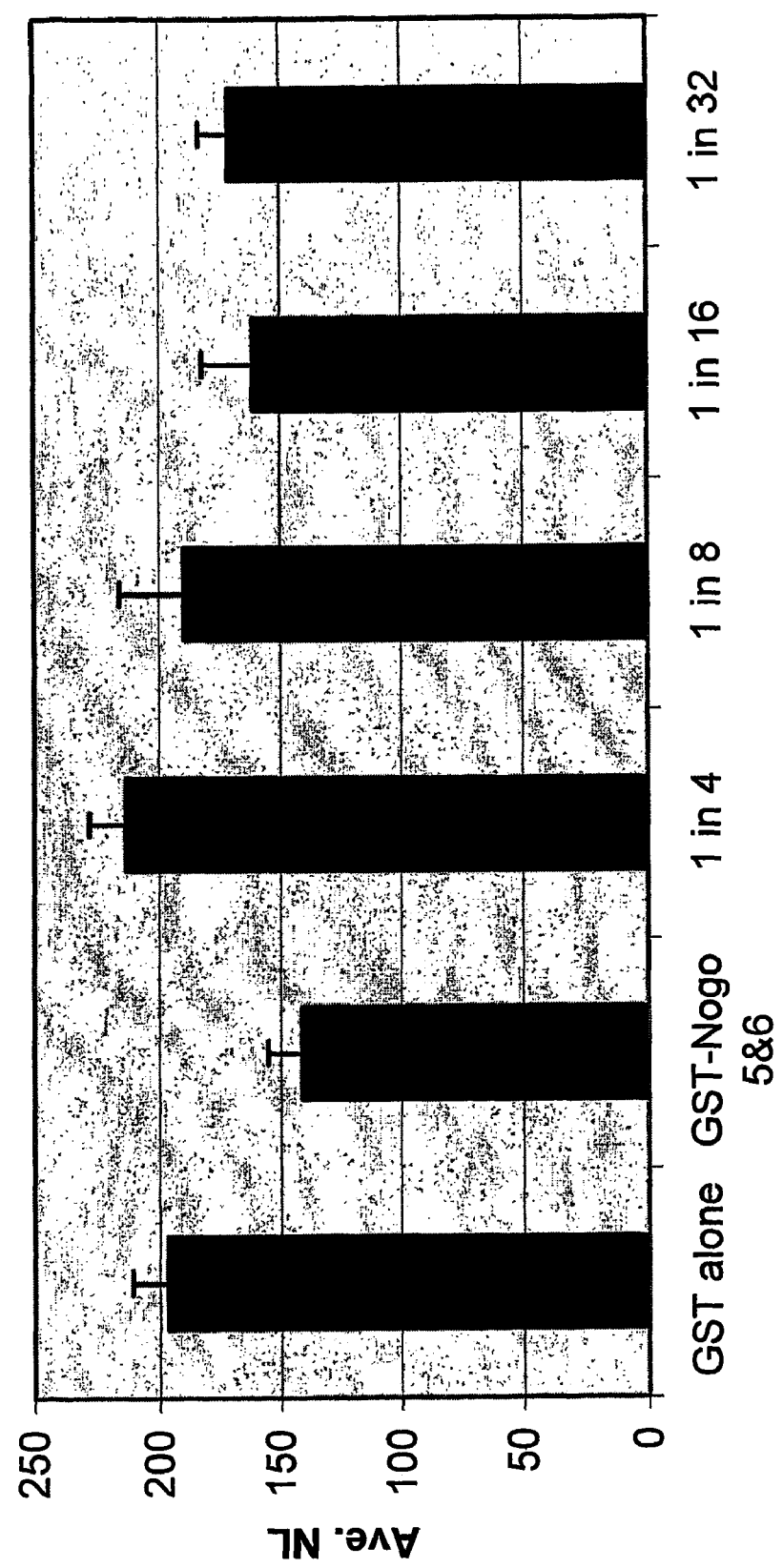
FIG. 3 shows the blocking effect by the supernatant of the hybridoma 2C4 on the neurite outgrowth inhibitory activity of NOGO-A56 (GST-Nogo5&6). The Y axis is as for FIG. 1.
Figure 4:
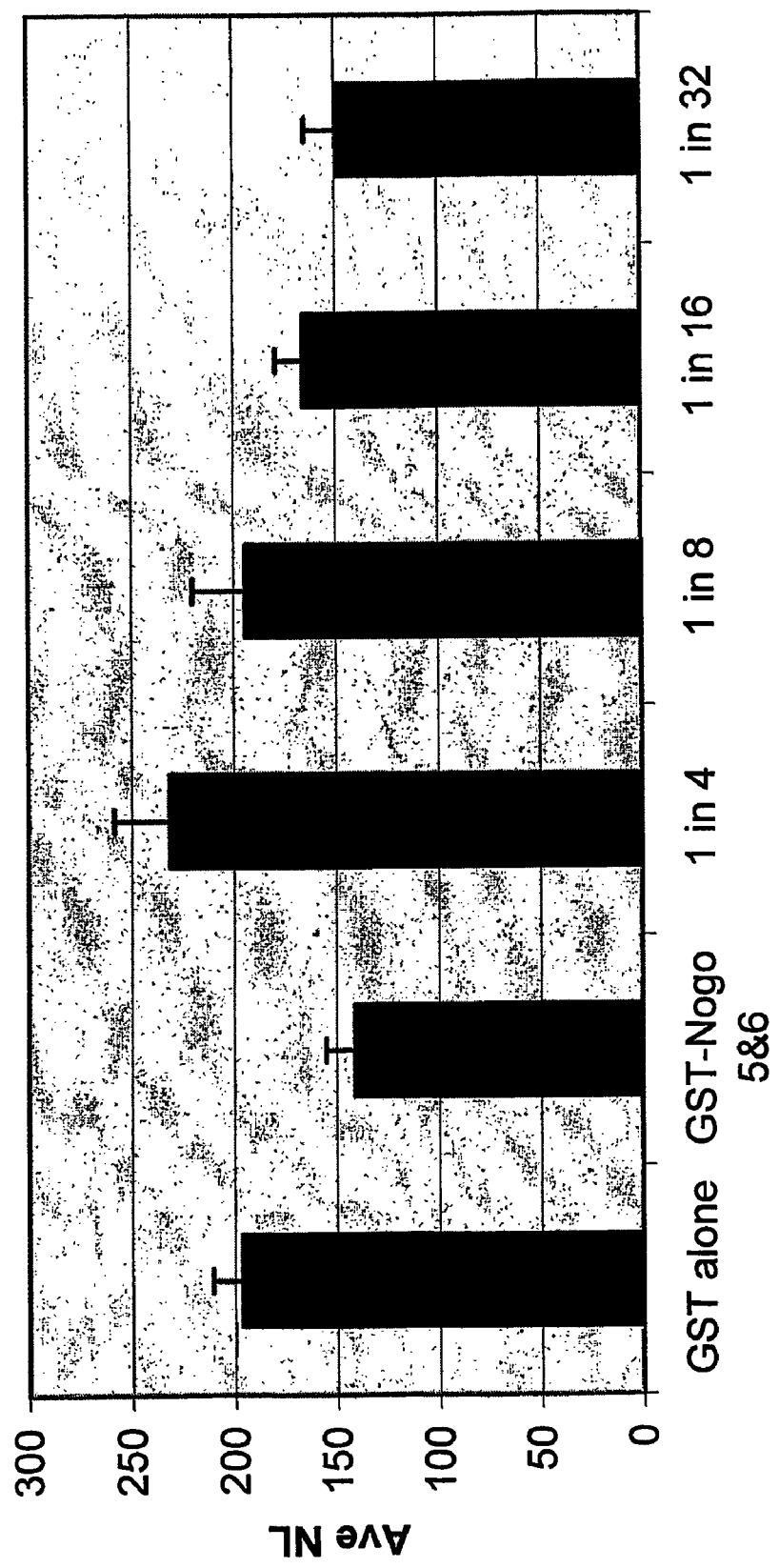
FIG. 4 shows the blocking effect by the supernatant of the hybridoma 15C3 on the neurite outgrowth inhibitory activity of NOGO-A56 (GST-Nogo5&6). The Y axis is as for FIG. 1.
Figure 5:
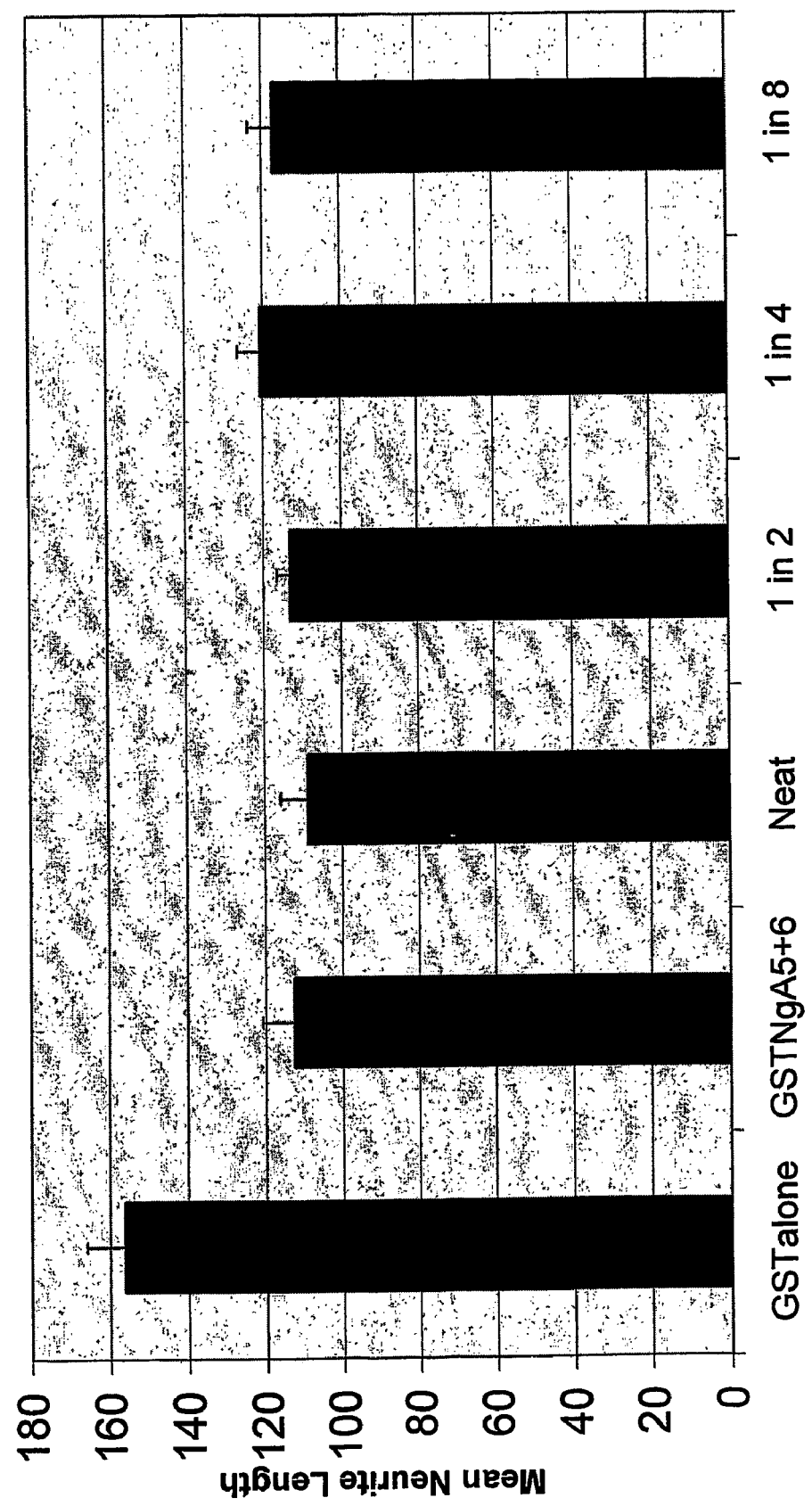
FIG. 5 is the control hybridoma supernatant 12G3 which has no NOGO-A56 blocking activity. The Y axis is as for FIG. 1.

FIG. 1 shows the inhibitory effect of NOGO-A56 on neurite outgrowth compared with the control protein GST alone.

FIGS. 2 through 5 show the identification of function-blocking anti-NOGO antibodies 2A10/3, 2C4/1 and 15C3/3 together with a non-function blocking control antibody 12G3. Antibody 12G3 binds to NOGO56 but does not inhibit neurite outgrowth activity. The graphs show the average neurite length in cultures exposed to unpurified antibodies (in supernatants). The data shows the blocking effect of 2A10/3, 2C4/1 and 15C3/3 of the neurite outgrowth inhibitory activity of NOGO-A56. The control is GST alone.

Figure 6:
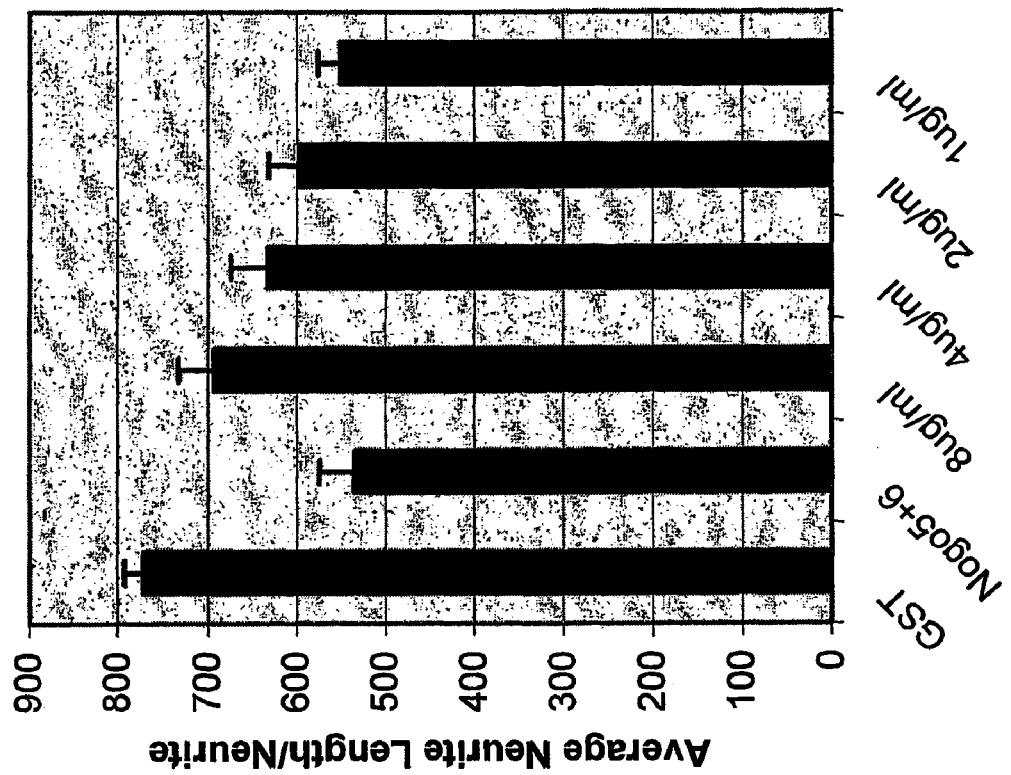
FIG. 6 shows the NOGO-A56-blocking effect of purified 2A10 at 4 concentrations. The Y axis is as for FIG. 1.

FIG. 6 shows the blocking of the neurite outgrowth inhibitory effect of NOGO-A56 by purified 2A10/3.

EXAMPLE 7

IN-1 has no Blocking Activity Against Human NOGO

Figure 7:
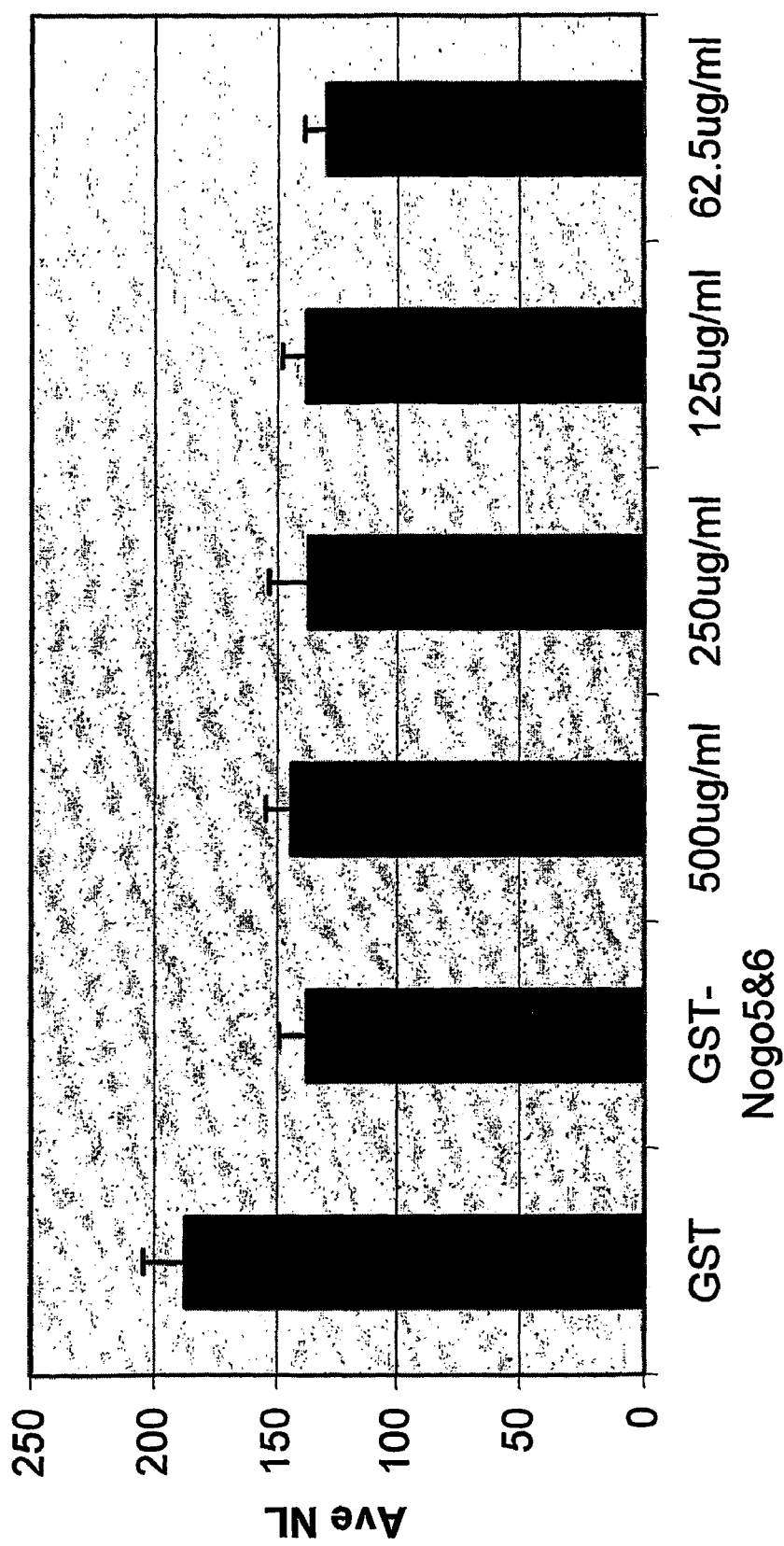
FIG. 7 shows that recombinant IN-1 monoclonal antibody does not show any blocking activity towards NOGO-A56 (GST-NOGO5&6). Y axis is as for FIG. 1.

The neurite outgrowth assay as described in example 5, when carried out with the IN-1 antibody, shows that IN-1 does not block the inhibitory activity of human NOGO-A (FIG. 7).

EXAMPLE 8

Humanisation of 2A10

Humanised $V_H$ and $V_L$ constructs were prepared de novo by build up of overlapping oligonucleotides including restriction sites for cloning into RId and RIn mammalian expression vectors as well as a human signal sequence. Hind III and Spe I restriction sites were introduced to frame the $V_H$ domain containing the CAMPATH-1H signal sequence for cloning into RId containing the human γ1 mutated constant region. Hind III and BsiW I restriction sites were introduced to frame the $V_L$ domain containing the CAMPATH-1H signal sequence for cloning into RIn containing the human kappa constant region.

```
CAMPATH-1H
signal sequence:
MGWSCIILFLVATAWGVHS      (SEQ.I.D.NO: 82)
```

Heavy Chain

One human germline sequence with 66% identity to the 2A10 $V_H$ amino acid sequence was identified. The framework sequence of U84162 was selected for humanisation:

QVQLVQSGAEVKKPGASVKVSCKASGYTFTSYYMHWVRQAPGQGLEWMGIINPSGGSTSY    (SEQ.I.D.NO: 83)

AQKFQGRVTMTRDTSTSTVYMELSSLRSEDTAVYYCARGQWLVIINFDYWGQGTLVTVSS.

The present invention therefore provides the use of SEQ.I.D.NO:83 (or a framework with less than 10 amino acid differences with SEQ.I.D.NO:83 e.g. less than 8 amino acids differences, preferably less than 6 amino acid differences, more preferably less than 4 amino acid differences e.g. 2 or 1 amino acid difference(s)) in the production of a humanised anti-NOGO antibody (particularly an anti-NOGO antibody which binds to human NOGO-A and comprises the CDRs set forth in Table 2 and/or binds to the epitope set forth above) Positions 93 and 94 were identified as potentially important residues in maintaining CDR conformation.

| Position (Kabat#) | 2A10 $V_H$ | U84162 |
|---|---|---|
| 93–94 | EL | AR |

It was noted that the EL motif at these positions are unusual. The following humanised construct was designed:

Humanised $V_H$ construct H1:

QVQLVQSGAEVKKPGASVKVSCKASGYT-    (SEQ.I.D.NO: 84)
FTSYWMHWVRQAPGQGLEWMGNINPSNGGTNY

NEKFKSRVTMTRDTSTSTVYMELSSLRSEDTAVYYCELGQGYWGQGTTVTVSS.

Light Chain

A human germline sequences with 66% identity to the 2A10 $V_L$ amino acid sequence were identified. The framework sequence of CM85593 was selected for humanisation:

Framework: CM85593 to DIVMTQSPLSLPVTLGQPA-SISCRSSQGLVYSDGDTYLNWFQQR-PGQSPRRLIYKVSNRD SGVPDRFSGGGSGTD-FTLKISRVEAEDVGVYYCMQGTHWPYTFGQGTKLEIK (SEQ.I.D.NO:85). Thus the present invention provides the use of SEQ.I.D.NO:85 (or a framework with less than 8 amino acid differences e.g. 6 amino acid differences, preferably less than 4 amino acid differences e.g. 2 or 1 amino acid difference(s)) in the production of a humanised anti-NOGO antibody which humanised antibody binds to NOGO-A (particularly an antibody which comprises the light chain of one or more (e.g. all) CDRs set forth in table 1 above and/or binds to the epitope of NOGO-A set forth above) and neutralises the activity of NOGO-A, particularly human NOGO-A.

The following framework residues were identified as potentially important in recovering affinity:

| Position (Kabat#) | 2A10 $V_L$ | AAK94811 |
|---|---|---|
| 4 | I | M |
| 45 | R | Q |
| 46 | R | L |

A humanised V$_L$ construct was designed:

| construct | framework template | position (Kabat#) | Amino acid human | mouse |
|---|---|---|---|---|
| L11 | CAA85593 | 4 | M | I |
|  |  | 45 | R | Q |
|  |  | 46 | R | L |

Humanised V$_L$ construct L11:

DIVITQSPLSLPVTLGQPASISCRSSK-SLLYKDGKTYLNWFQQRPGQSPQLLIYLMSTRA (SEQ.I.D.NO: 86)

SGVPDRFSGGGSGTDFTLKISRVEAEDVGVYYCQQLVEYPLTFGQGTKLEIK

Plasmids encoding SEQ.I.D.NO:84 and 86 were transiently co-transfected into CHO cells and expressed at small scale to produce antibody H1L11. Plasmids encoding SEQ.I.D.NO:92 and 86 may also be transiently co-transfected into CHO cells and expressed at small scale to produce antibody H7L11.

Thus the invention provides a humanised antibody that binds to and neutralises the activity of NOGO, particularly human NOGO, more particularly human, NOGO-A, which humanised antibody comprises a heavy chain variable region of SEQ.I.D.NO:84 and a light chain variable region of SEQ.I.D.NO:86. In a further aspect of the invention there is provided an antibody (particularly a fully human or humanised antibody) that binds to and neutralises the activity of NOGO, particularly human NOGO, more particularly human NOGO-A, which antibody competitively inhibits the binding of the humanised antibody comprising a heavy chain variable region of SEQ.I.D.NO:85 and a light chain variable region of SEQ.I.D.NO:86, at equimolar concentration, to human NOGO-A. Preferably the competing antibody inhibits at least 50% of the binding of the antibody comprising a heavy chain variable region of SEQ.I.D.NO:85 and light chain variable region of SEQ.I.D.NO:86 to human NOGO-A.

In accordance with the present invention there is provided an anti-NOGO antibody which specifically binds to and neutralises the activity of human NOGO-A which antibody comprises a heavy chain of SEQ.I.D.NO:88 and a light chain of SEQ.I.D.NO:89. The present invention also concerns pharmaceutical compositions comprising said antibody and methods of treating a human patient, particularly a patient afflicted with stroke (such as Ischemic stroke) or Alzheimer's disease. It will be apparent to those skilled in the art that SEQ.I.D.NO: 88 and SEQ.I.D.NO:89 represent the heavy chain and light chain respectively prior to any processing (e.g. host cell mediated processing) for removal of a signal sequence. Typically the processed form of SEQ.I.D.NO:88will begin at position 20 and the processed form of SEQ.I.D.NO:89 will begin at position 20.

SEQ.I.D.NO: 88
MGWSCIILFLVATATGVHSQVQLVQSGAEVKKPGASVKVSCKASGYTFTSYWMHWVRQAP

GQGLEWMGNINPSNGGTNYNEKFKSRVTMTRDTSTSTVYMELSSLRSEDTAVYYCELGQG

YWGQGTLVTVSSASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKKVEPKSCDKTHT

CPPCPAPELAGAPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTTPPVLDSDGSFF

LYSKLTVDKSRWQQGNVFSCSVNHEALHNHYTQKSLSLSPGK.

SEQ.I.D.NO: 89
MGWSCIILFLVATATGVHSDIVITQSPLSLPVTLGQPASISCRSSKSLLYKDGKTYLNWF

QQRPGQSPQLLIYIMSTRASGVPDRFSGGGSGTDFTLKISRVEAEDVGVYYCQQLVEYPL

TFGQGTKLEIKRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSFNRGEC.

A polynucleotide encoding SEQ.I.D.NO:88 is set forth in SEQ.I.D.NO:90:

AAGCTTTACAGTTACTCAGCACACAG-                                         (SEQ.I.D.NO: 90)
GACCTCACCATGGGATGGAGCTGTATCATCCTCT

TCTTGGTAGCAACAGCTACAGGTGTC-
CACTCCCAGGTGCAGCTGGTGCAGTCTGGGGCTG

AGGTGAAGAAGCCTGGGGCCTCAGT-
GAAGGTTTCCTGCAAGGCATCTGGATACACCTTCA

CCAGCTACTGGATGCACTGGGTGCGA-
CAGGCCCCTGGACAAGGGCTTGAGTGGATGGGAA

ATATTAATCCTAGCAATGGTGGTAC-
TAACTACAATGAGAAGTTCAAGAGCAGAGTCACCA

TGACCAGGGACACGTCCACGAGCA-
CAGTCTACATGGAGCTGAGCAGCCTGAGATCTGAGG

ACACGGCCGTGTATTACTGTGAACTGG-
GACAGGGCTACTGGGGCCAGGGAACACTAGTCA

CAGTCTCCTCAGCCTCCACCAAGGGC-
CCATCGGTCTTCCCCCTGGCACCCTCCTCCAAGA

GCACCTCTGGGGGCACAGCGGC-
CCTGGGCTGCCTGGTCAAGGACTACTTCCCCGAACCGG

TGACGGTGTCGTGGAACTCAGGCGCCCT-
GACCAGCGGCGTGCACACCTTCCCGGCTGTCC

TACAGTCCTCAGGACTCTACTCCCTCAG-
CAGCGTGGTGACCGTGCCCTCCAGCAGCTTGG

GCACCCAGACCTACATCTGCAACGT-
GAATCACAAGCCCAGCAACACCAAGGTGGACAAGA

AAGTTGAGCCCAAATCTTGTGA-
CAAAACTCACACATGCCCACCGTGCCCAGCACCTGAAC

TCGCGGGGGCACCGTCAGTCTTCCTCT-
TCCCCCCAAAACCCAAGGACACCCTCATGATCT

CCCGGACCCCTGAGGTCACATGCGTG-
GTGGTGGACGTGAGCCACGAAGACCCTGAGGTCA

AGTTCAACTGGTACGTGGACGGCGTG-
GAGGTGCATAATGCCAAGACAAAGCCGCGGGAGG

AGCAGTACAACAGCACGTACCGTGTGGT-
CAGCGTCCTCACCGTCCTGCACCAGGACTGGC

TGAATGGCAAGGAGTACAAGTGCAAG-
GTCTCCAACAAAGCCCTCCCAGCCCCCATCGAGA

AAACCATCTCCAAAGCCAAAGGGCAGC-
CCCGAGAACCACAGGTGTACACCCTGCCCCCAT

CCCGGGATGAGCTGACCAAGAACCAGGT-
CAGCCTGACCTGCCTGGTCAAAGGCTTCTATC

CCAGCGACATCGCCGTGGAGTGGGAGAG-
CAATGGGCAGCCGGAGAACAACTACAAGACCA

CGCCTCCCGTGCTGGACTCCGACGGCTC-
CTTCTTCCTCTACAGCAAGCTCACCGTGGACA

AGAGCAGGTGGCAGCAGGGGAACGTCT-
TCTCATGCTCCGTGATGCATGAGGCTCTGCACA

ACCACTACACGCAGAAGAGCCTCTCCCTGTCTCCGGGTAAATGAATTC

A polynucleotide encoding SEQ.I.D.NO:89 is set forth as SEQ.I.D.NO:91:

AAGCTTTACAGTTACTCAGCACACAGGACCTCACCATGGGATGGAGCTGTATCATCCTCTTCTTG  (SEQ.I.D.NO: 91)

GTAGCAACAGCTACAGGTGTCCACTCCGATATTGTGATAACCCAGTCTCCACTCTCCCTGCCCGT

CACCCTTGGACAGCCGGCCTCCATCTCCTGCAGGTCTAGTAAGAGTCTCCTATATAAGGATGGGA

-continued

```
AGACATACTTGAATTGGTTTCAGCAGAGGCCAGGCCAATCTCCACAGCTCCTAATTTATTTGATG

TCCACCCGTGCATCTGGGGTCCCAGACAGATTCAGCGGCGGTGGGTCAGGCACTGATTTCACACT

GAAAATCAGCAGGGTGGAGGCTGAGGATGTTGGGGTTTATTACTGCCAACAACTTGTAGAGTATC

CGCTCACGTTTGGCCAGGGGACCAAGCTGGAGATCAAACGTACGGTGGCTGCACCATCTGTCTTC

ATCTTCCCGCCATCTGATGAGCAGTTGAAATCTGGAACTGCCTCTGTTGTGCCTGCTGAATAA

CTTCTATCCCAGAGAGGCCAAAGTACAGTGGAAGGTGGACAACGCCCTCCAATCGGGTAACTCCC

AGGAGAGTGTCACAGAGCAGGACAGCAAGGACAGCACCTACAGCCTCAGCAGCACCCTGACGCTG

AGCAAAGCAGACTACGAGAAACACAAAGTCTACGCCTGCGAAGTCACCCATCAGGGCCTGAGCTC

GCCCGTCACAAAGAGCTTCAACAGGGGAGAGTGTTAGGAATTC
```

EXAMPLE 9

BiaCore Analysis of H1L11 Anti NOGO Monoclonal Antibody

The binding kinetics of the anti-NOGO monoclonal antibody (mAb) to recombinantly expressed human NOGO-A (hNOGO) was analysed using the Biacore3000 biosensor. The methodology was as followed:

Method hNOGO was immobilised to a CM5 chip by primary amine coupling using the Biacore Wizard program designed for targeted immobilisation levels. The CM5 sensor surface was activated by passing a solution of 50 mM N-hydroxy-succinimide (NHS) and 200 mM N-ethyl-N'-dimethylaminopropyl carbonide (EDC). Then using a 300 nM solution of hNOGO in 5 mM sodium acetate, pH5.0, a range of concentrations between 50-200 resonance units of hNOGO were immobilised. After immobilisation was complete any still activated esters were blocked by an injection of 1 M ethanolamine hydrochloride, pH8.5.

The H1L11 mAb (see example 8) was diluted down in HBS-EP (10 mM HEPES, pH 7.4, 150 mM NaCl, 3 mM EDTA, and 0.005% P-20 surfactant) and binding studies were carried out at concentrations ranging between 0.1-100 nM. For kinetic analysis a flowrate of 60 µl/minute was used, with no mass transfer effects seen. All concentrations were performed in duplicate, in a random order with buffer blanks included. Regeneration was achieved either by the single injection of a 15 µl pulse of 50 mM sodium hydroxide alone or the injection of 15 µl of 100 mM $H_3PO_4$, followed by a subsequent injection of 15 µl of 50 mM sodium hydroxide. Both regeneration protocols were run at a flowrate of 30 µl/minute; and both methods resulted in the complete removal of bound H1L11 but did not result in any loss of binding capacity of the hNOGO sensor surface. All runs were referenced against a blanked sensor surface (one that had been activated and blocked as described earlier but had no addition of ligand). Analysis of binding was carried out using the BIAevaluation kinetic analysis software version 4.1. Biacore analysis of other antibodies of the invention essentially followed the same protocol as described herein.

Results

| Antibody | ka (1/Ms) | kd (1/s) | KD (nM) |
|---|---|---|---|
| HcLc | $2.23 \times 10^6$ | $2.49 \times 10^{-3}$ | 1.26 |
| H1L11 | $1.0 \times 10^6$ | $2.15 \times 10^{-2}$ | 22.16 |

-continued

Results

| Antibody | ka (1/Ms) | kd (1/s) | KD (nM) |
|---|---|---|---|
| Mouse 2A10 | $2.9 \times 10^6$ | $1.84 \times 10^{-3}$ | 0.8 |
| Mouse 2C4 | $8.09 \times 10^6$ | $6.44 \times 10^{-4}$ | 8 |
| Mouse 15C3 | $4.07 \times 10^4$ | $8.28 \times 10^{-4}$ | 17.5 |

A similar analysis was carried out using rat NOGO-A.

Results:-

| Antibody | Ka (1/Ms) | Kd (1/s) | KD (nM) |
|---|---|---|---|
| Mouse 2C4 | $1.62 \times 10^5$ | $5.33 \times 10^{-4}$ | 3.9 |
| Mouse 15C3 | $4.6 \times 10^4$ | $8.7 \times 10^{-4}$ | 24.9 |
| Mouse 2A10 | $1.26 \times 10^6$ | $1.01 \times 10^{-3}$ | 1 |

EXAMPLE 10

Effect of Anti-NOGO Antibody (2C4) on Lesion Volume and Functional Recovery Following tMCAO Aim:

The aim of this study was to investigate the efficacy of an anti-NOGO monoclonal antibody (mab) dosed intracerebroventricularly (ICV) on lesion volume and functional recovery of rats post transient middle cerebral artery occlusion (tMCAO). Cylinder test, tapered beam and neurological score tasks were utilised to assess long term functional recovery following 90 minutes of transient ischaemia and brains were harvested for immunohistochemistry evaluation of regenerative processes and lesion volume assessment.

Methods:

Surgical Preparation

Male Sprague-Dawley rats (300-350 g) supplied by Charles River, were used in the study. Intra-cerebral ventricular (i.c.v.) cannulae were positioned in the left lateral cerebral ventricle under general anaesthesia. Following at least 4 days recovery from surgery, cannulae placement was confirmed by challenge with Angiotensin II administered ICV.

Induction of Focal Ischaemia

All animals underwent tMCAO under halothane/oxygen/nitrous oxide anaesthesia as described by Longa and co-workers (Stroke, 1989, 20, 84-91). Body temperature was monitored throughout the surgical procedure by a rectal thermometer, and the animals were maintained normothermic (37±0.50 C) via a heating blanket controlled by the thermometer. Actual core temperature values were recorded at the time of left middle cerebral artery (MCA) occlusion and at reperfusion.

Ninety minutes after MCA occlusion, the rats were re-anaesthetised and the filament slowly and completely withdrawn to allow reperfusion. The arteriotomy is closed with diathermy, haemostasis was re-checked, and the cervical wound sutured closed.

Post-Occlusion Recovery

Following MCA occlusion, anaesthesia was discontinued and the animals allowed to regain consciousness and righting reflex under strict observation in an incubator (23-25° C.) for 1 hour. The animals were then housed individually in the post-operative recovery room, where their overall health status was closely monitored throughout the survival period.

Behavioural Tasks:

1. Neurological Assessment:

Motor and behavioural changes following MCA occlusion were assessed using a 28 point grading scale at time points 1 hour, 24 hours and then weekly for 8 weeks after MCA occlusion.

Details of Neurological Assessment ("Neuroscore") Used:
Neuroscore of MCAO Animals when Compared to Other Rats within the Same Study—Maximum Score 28 Points Paw Placement Hold the animal lengthways at the edge of bench, cupping your hand over its head, and, one by one, take each paw and place it over the edge of the bench. Watch for paw retraction, and placement back on the bench.

Score: 1 for each successful paw placement (Max score=4)

Righting Reflex

Grasp the animal firmly, and rotate it until it is lying on its back in the palm of your hand. Release grip and see if the animal rights itself Score: 1 for successful righting Horizontal Bar Place the fore-paws of the animal on a ribbed bar and allow it to hang.

Score: 3 if both hindlimbs rise onto the bar 2 if one hindlimb rises to bar 1 if animal just hangs 0 if animal falls off (due to lack of grip)

Inclined Platform

Hold cage lid at 45°. Place animal 'downhill' on the lid

Score: 3 if the animal rotates to face 'uphill' within 15 seconds 2 if it takes 15-30 seconds 1 if it takes longer than 30 seconds 0 if the animal falls off the lid due to weak/absent grip, or remains pointing 'downhill'

Contralateral Rotation

Hold the animal by the base of the tail and rotate the animal clockwise then anticlockwise. Watch for the animal's ability to swivel up contralaterally to the direction of rotation Score: 1 for each side (Max score=2)

Visual Fore-Paw Reaching

Hold the animal by the base of the tail with its head just below the level of the bench top. Approach the bench until the animal's vibrissae are almost touching it. The animal should arch and attempt to place its forepaws on the bench surface.

Score: 1 for each successful paw placement (Max score=2)

Circling

Place the animal on the floor and look for circling

Score: 4 for non-circling 3 tends to one side 2 for large circles>50 cm radius 1 for medium circles>15<50 cm radius 0 for spinning/tight circles <15 cm radius Contralateral Reflex Hold animal by the base of the tail Score: 0 for a reflex 1 for no reflex Grip Strength Let animal hold onto bars on cage with front paws only.

Drag animal back by tail

Score: 2—normal grip strength.

1—weakened grip strength

0—no grip

Motility

Observe whilst on the floor for circling activity

Score: 3—for normal motility

2—if lively but circling

1—if unsteady

0—if reluctant to move

General Condition

Score: 3—normal (good coat condition, alert, moving about, weight gain normal)

2—Very good but weight gain less than normal

1—good

0—fair (e.g. dirty coat, may not be grooming much, hunched posture, aggressive, weak muscle tone)

Maximum Score (i.e. Normal Rat)=28

2. Cylinder Test:

Animals were assessed weekly in the cylinder test of forepaw placement. Animals were placed inside a transparent Perspex® cylinder 20 cm in diameter and 30 cm tall for a 3 minute period. The numbers of left and right forepaw placements are assessed in this period. This test was conducted in red light conditions.

3. Tapered Beam Walking:

For this test all the rats are trained in a red light room to cross a square tapered beam of 1 m length at an angle of approx 40 degrees running uphill towards its home cage. This task becomes progressively more difficult as the rat moves up the beam as the width of the beam decreases. The beam is marked so as to divide it into 3 sections for purposes of analysis, graded easy at the widest section (6 cm) through to hard at the tapered end (2 cm).

Pre operative training—for 2 days each rat was taken from its home cage and placed onto the beam at increasing distances (approx 4 times in total). When each rat could cross the beam without coaxing and with few foot faults it is classed as trained. Any poor performers were excluded from the test.

Testing—each rat was placed on the beam 3 times per test session and the latency to cross, number of foot slips, defined as a foot placement which does not achieve contact with the top surface of the beam, (hind and forelimb) was recorded manually and the average of these then taken. At weeks 5 for batch 1 and week 4 for batch two of the animals, analysis was changed to video recording of the test. Analysis from the recorded test was then carried out in order to increase sensitivity.

Test sessions for MCAO animals were prior to surgery, then post operative at day 7 and weekly thereafter until sacrifice at week 8.

Dosing Regime

Antibody was administered at 1 hour, 24 hours, 1 week and 2 weeks following occlusion.

Groups:
IgG1 control (5 μg) (Group D)
Antibody 2C4 (5 μg) (Group F)
Antibody 2C4 (15 μg) (Group E)

All preparations were made in sterile saline.

Groups were blinded prior to administration.

To avoid bias introduced by the order of rats used, a Latin square design was employed.

Antibodies were dosed in a volume of 5 μl stock (1 mg/ml and 3 mg/ml) delivered over 2 min with the aid of an infusion pump (2.5 μl/min). Following injection, cannulae remained in place for a further 2 min.

Neuropathology and Quantification of Ischaemic Damage 8 weeks after MCA occlusion, rats were perfusion fixed with ice-cold 4% paraformaledehyde. The animals were then decapitated and the brains stored in situ in ice-cold 4% paraformaledehyde, prior to dissection and processing for paraffin embedding and subsequent immunohistochemistry.

For brain volume analysis brains were serially sliced from the anterior pole to the cerebellum for paraffin processing at 2 mm intervals using a brain matrix. The brains are then paraffin processed and embedded in wax. 4 micron sections were collected that correspond to stereotactically pre-determined coronal planes from anterior +3 mm to posterior −7.5 mm relative to bregma. The sections were mounted on to poly lysine coated slides prior to staining with Haematoxylin and Eosin. The sections were analysed for lesion volume and swelling using a computer based image analysis system (Datacell, hardware. Optimas Software). Lesioned areas are comprised of tissue that has not been stained by the Haematoxylin and Eosin. Lesions are measured by tracing around the boundaries of the lesioned area and expressed as % lesioned area compared to contralateral non lesioned side of the brain.

Statistical Analysis:

The neuroscore and bodyweights data were analysed using a repeated measures ANOVA approach with time as the repeated measure. Lesion volume was analysed using a 1-way ANOVA and ANCOVA approach and lesion area was analysed using a repeated measures ANCOVA approach The foot slips data were analysed separately for the fore and hind limbs, to look for a group effect, using a repeated measures ANOVA approach with week and beam difficulty as the repeated measures. To look for differences between fore and hind limbs, the foot slips data were also analysed using a repeated measures ANOVA approach with week and leg as repeated measures, averaged across difficulty.

Three animals from group E (high dose Ab group) received one dose less than the other animals in this group (see below). Although, the analysis was carried out with and without these animals and it showed there was no significant effect on the results and the animals were therefore included in the analysis, it is important to note that in the case of the cylinder test and the body weight profiles, when comparing animals dosed 3 times and animals dosed 4 times with controls, only animals dosed 4 times are significantly different to animals dosed with control antibody.

It should be noted that during the course of this study, a number of rats died due to a putative infection. As a consequence, three animals in the highest dose group (group E) received one dose less than the other animals in this group.

Results:

Three animals from group E (high dose Ab group) received one dose less than the other animals in this group. The data was analysed with and without these animals and there was no significant effect on the results of the analysis unless stated in the text.

FIG. 9 shows the lesion volume as a percentage of total brain volume in the control and 5 μg and 15 μg test groups. The antibody had no effect on lesion volume when compared to the control group.

FIG. 10.

This figure shows neuroscore data represented as means±SEM. Due to the large range of data observed parametric analysis was deemed to be valid. There are significant differences between the 15 μg dosed group and control at weeks 1, 4, 7 and 8.

There are significant differences between the 15 μg dosed group and control at week 7 and 8 when analysed in this manner.

Cylinder Test

See FIGS. 11A, 11B, 11C, 11D. Cylinder data represented as mean±SEM for A) both paws, B) left paw, C) right paw and D) right paw split into rats that received 3 doses of 15 μg of anti-NOGO antibody, and those which received 4 doses of anti-NOGO antibody.

The 15 μg dose of the antibody produced a significant increase in the use of the right paw.

Figure 11A:
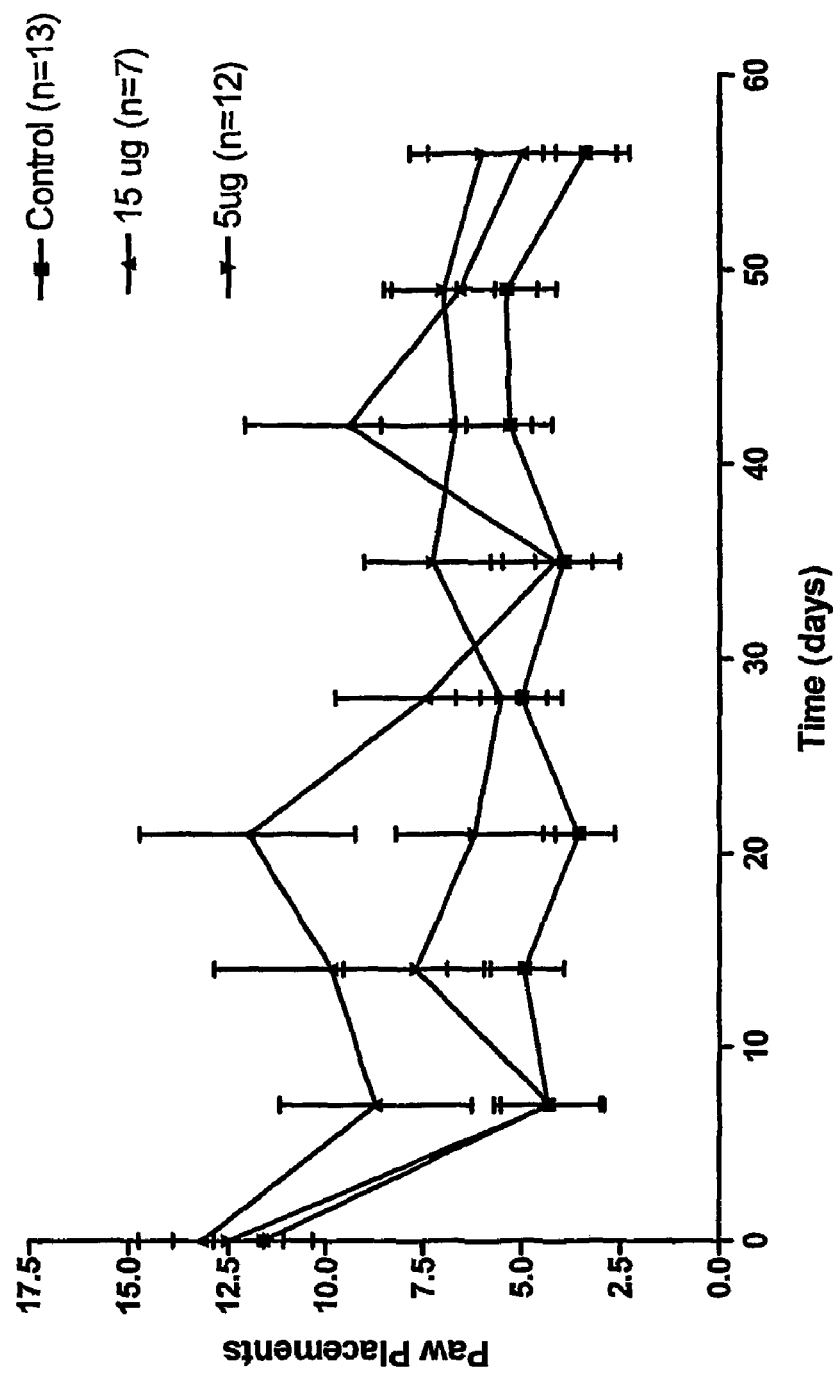
Figure 11B:
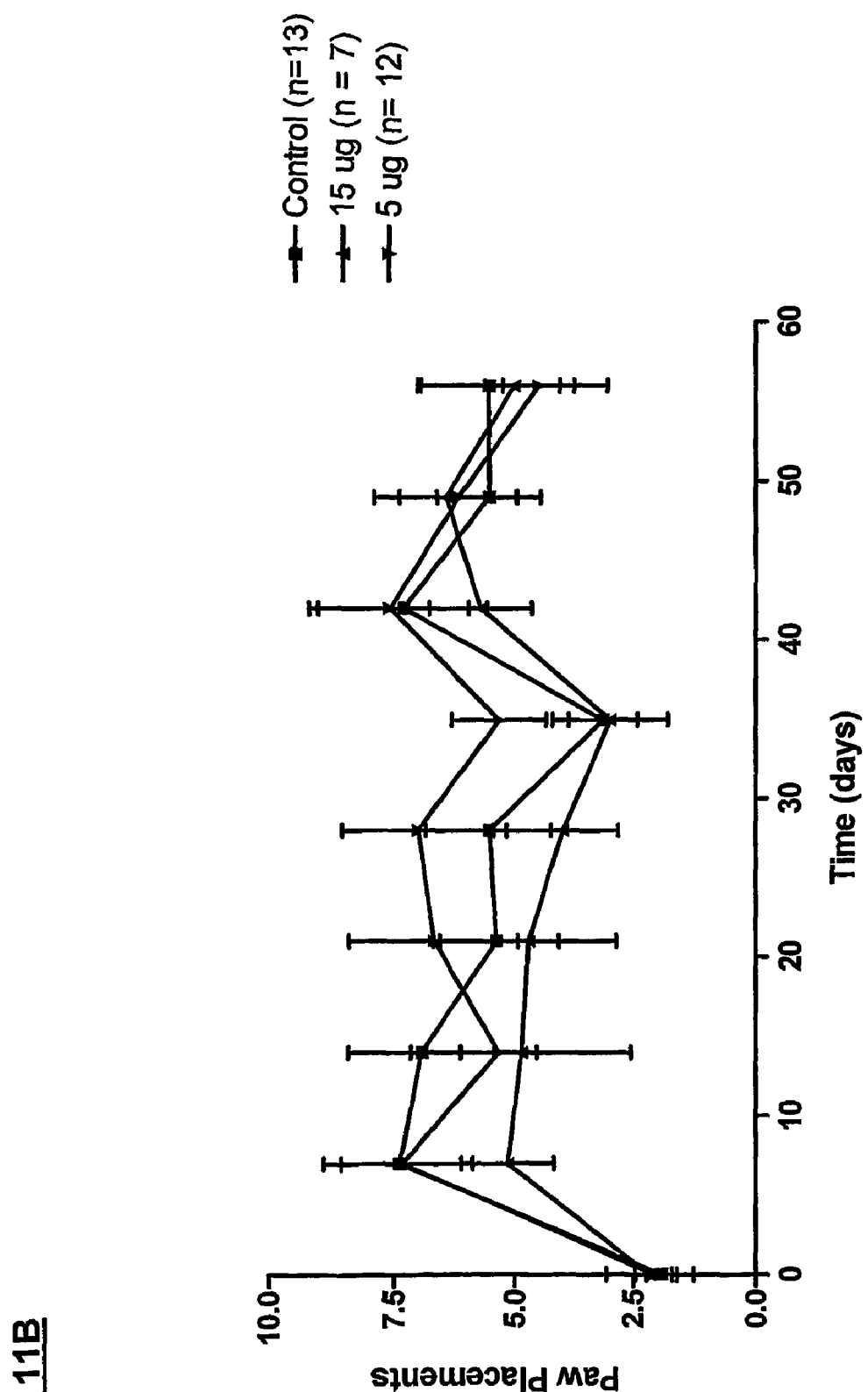
Figure 11C:
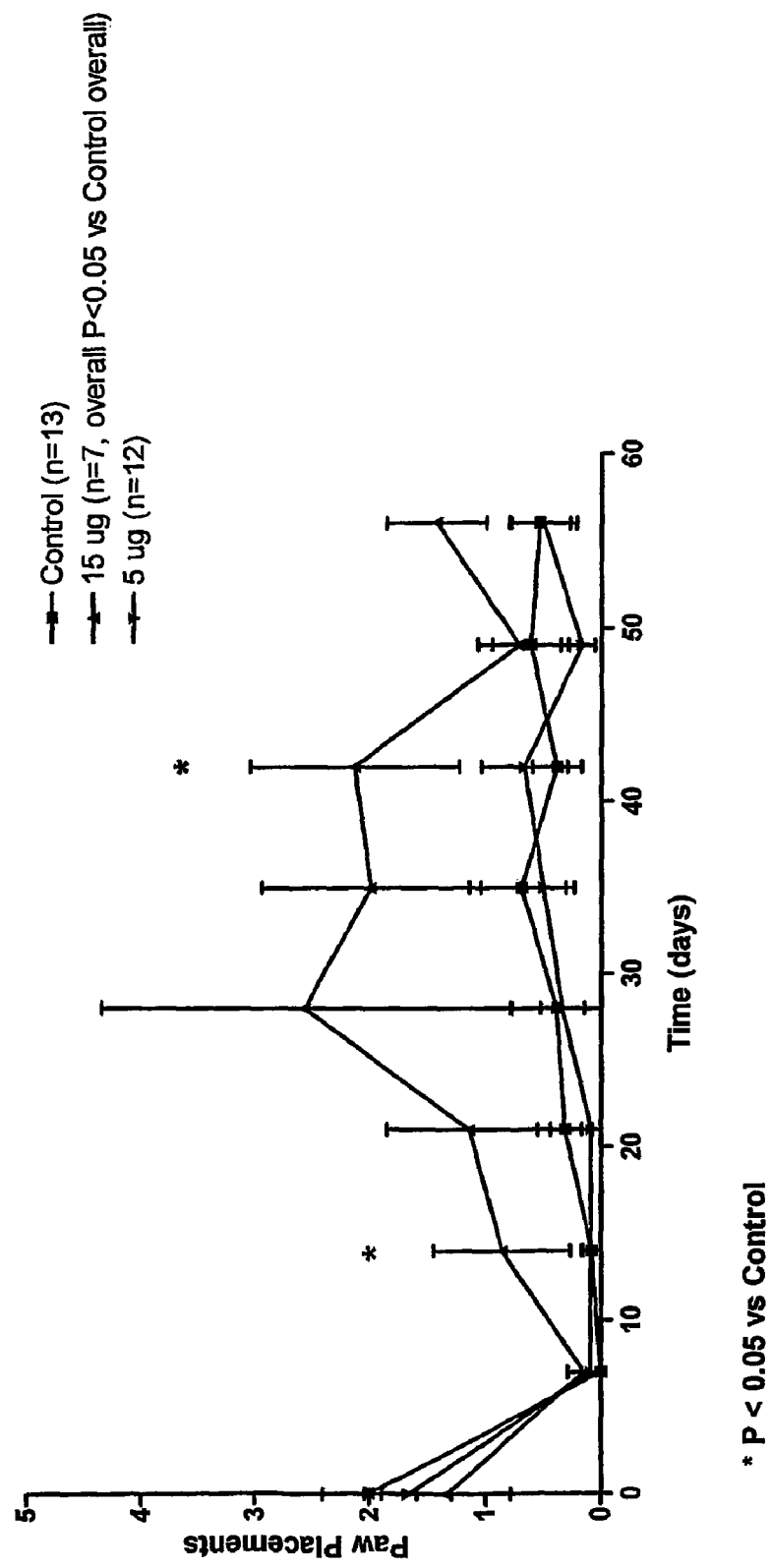
Figure 11D:
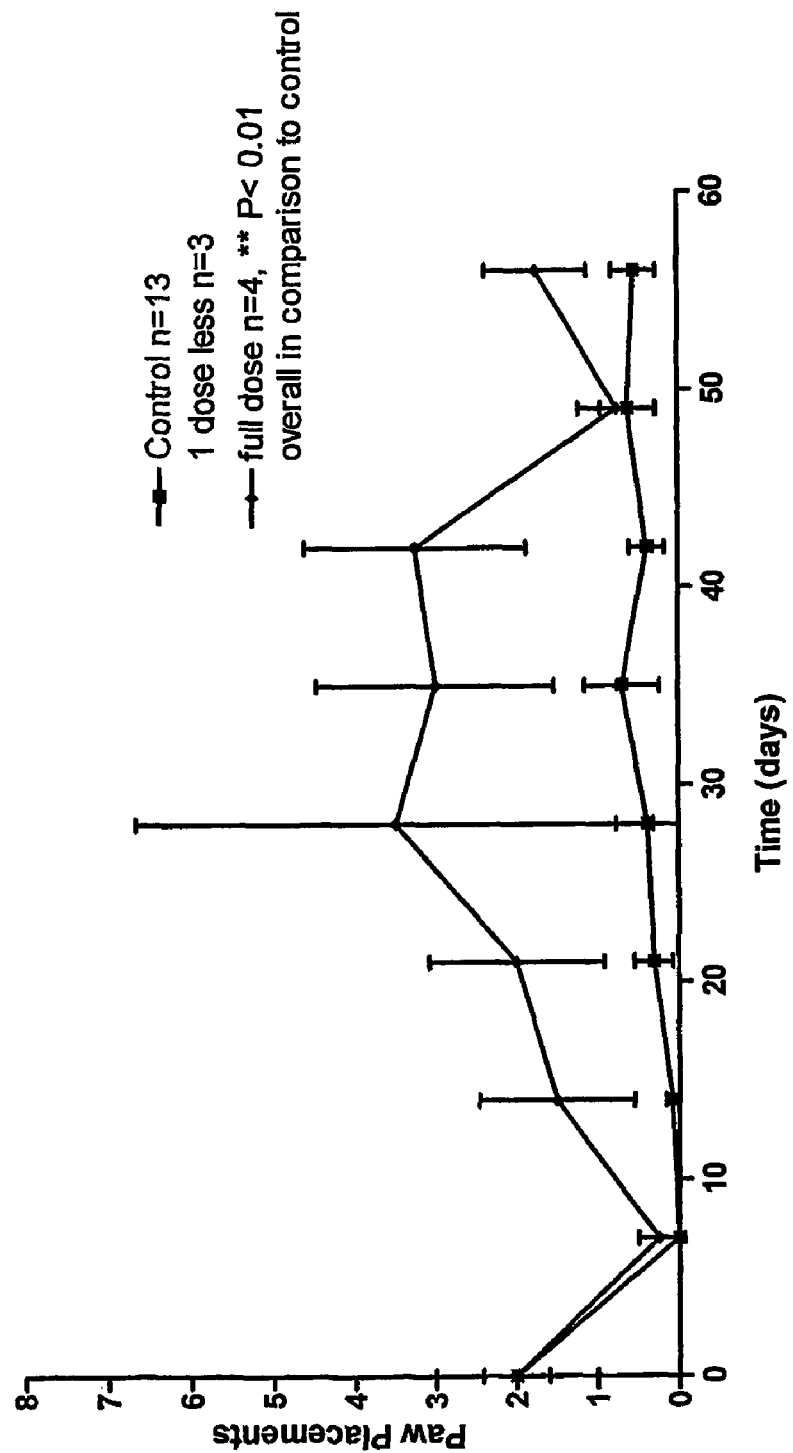

When the high dose group is divided into rats receiving all four doses versus rats receiving only three doses of the antibody, no significant difference is seen between the two subgroups. However as shown in FIG. 11D, when the 4 dose group is compared to the control group there exists a significant difference that is not seen when the 3 dose group is compared with control. Statistical analysis used Fisher's LSD test on repeated measures data.

Tapered Beam

See FIG. 12.

FIG. 12 shows forelimb foot slips represented as mean±95% confidence intervals.

In week 6, group F, the 5 μg dose is increasing the number of fore foot slips compared to group D, control, (p=0.0305).

Although not shown here, number of forepaw foot slips increased with increasing difficulty along the beam.

See FIG. 13.

FIG. 13 shows hindlimb footslips represented as mean±95% confidence intervals.

Group F, the 5 μg dose is significantly increasing the number of hind foot slips compared to group D, control, (p=0.0488) over the course of the study. In weeks 6 and 7, group F is significantly increasing the number of hind foot slips compared to group D, (p=0.0098 and p=0.0370 respectively).

Although not shown here, number of hindpaw foot slips increased with increasing difficulty along the beam.

The data for latency for animals to cross the beam shows that in the initial week's latency decreases as the animals recover, however no effect of treatment is observed.

FIG. 14A) shows body weights represented as means±SEM. Dosing animals with 15 μg of the antibody causes an increase in body weight at 24 hours, 1 week and at every time point from week 3 to the completion of the study.

FIG. 14B). Graph shows weights for the 15 μg dosed group split into animals dosed 3 times and those dosed four times. Data expressed as means±95% confidence intervals. *P<0.05, repeated measures ANOVA.

FIG. 14C). Graph shows weights for the 15 μg dosed group split into animals dosed 3 times and those dosed four times. Compared to animals dosed with 5 μg of the anti-NOGO antibody and animals dosed with control antibody. Data expressed as means±95% confidence intervals. *P<0.05, repeated measures ANOVA.

Although not significantly higher than the other groups, the high dose group had a high proportion of animals removed through euthanasia or death. This could account for the mean rise in body weight when compared to the control group.

Conclusions:

This study looked at the effect of two doses of the anti-NOGO antibody 2C4 on lesion volume and functional recovery after a 90 minute tMCAO when administered ICV at 1 hour, 24 hours, 1 week and 2 weeks.

The antibody treatment had no effect on lesion volume.

The antibody treatment had a modest, but significant effect on neurological score at the highest dose of 15 µg ICV. This dose significantly increased the neurological score at weeks 1, 4, 7 and 8 using the mean score (used as the data where spread over a large range, therefore justifying parametric analysis).

The antibody treatment had a significant effect on right paw use in the cylinder test at the highest dose, 15 µg ICV. This dose caused a significant increase in right paw use compared to control over the entire period of the study, there were also significant increases in right paw use specifically at weeks 2 and 6.

The antibody treatment had no positive effect on performance on the tapered beam walking test. However, it appears that the low dose antibody group (5 µg ICV) increased the number of footslips, especially at week 6. However no difference was seen when the number of footslips per difficulty section were analysed, nor when latency to cross the beam was analysed.

The antibody treatment had a significant effect on body weight at the highest dose, 15 µg ICV. This antibody group had a significantly increased body weight when compared to controls from 3 weeks onwards. Although not a functional outcome, body weight is a good reflection of general well being and this increase would reflect improved physiological recovery following tMCAO.

The last 3 rats in the group receiving the higher dose of the antibody did not receive the fourth and final dose for the reasons given above. In order to determine the importance of this final dose a comparison of rats in the highest antibody dose group receiving 3 doses as opposed to 4 doses was carried out.

Duration of Dosing

Animals dosed 4 times significantly increased number of right paw placements whereas animals dosed 3 times did not. In addition, dosing in the second week appears to accelerate the increase in body weight when compared to animals dosed 3 times. Dosing 4 times also produces a significant increase in weight compared to controls whereas dosing 3 times does not.

Dosing did not affect lesion volume, neurological score or performance in the tapered beam walking test Summary In summary, although the treatment had no effect on lesion volume, the highest dose of anti-NOGO antibody 2C4 (15 µg) had a positive effect on functional recovery, as assessed by neuroscore set forth herein, following 3 or 4 doses and paw placement and body weight following administration of 4 doses.

EXAMPLE 11

Effect of Intravenously Administered Anti-NOGO Monoclonal Antibodies on Lesion Volume and Functional Recovery Following tMCAO Aim:

The aim of this study was to investigate the efficacy of the anti-NOGO monoclonal antibodies (mabs) 2A10 and 2C4 dosed intravenously (IV) on lesion volume and functional recovery of rats post transient left middle cerebral artery occlusion (tMCAO). Cylinder test, tapered beam and neurological score tasks were utilised to assess long term functional recovery following 90 minutes of transient ischaemia and brains were harvested for immunohistochemistry evaluation of regenerative processes and lesion volume assessment.

Methods:

Induction of Focal Ischaemia

All animals underwent tMCAO under halothane/oxygen/nitrous oxide anaesthesia as described-by Longa and co-workers (Stroke, 1989, 20, 84-91). Body temperature was monitored throughout the surgical procedure by a rectal thermometer, and the animals were maintained normothermic (37±0.50 C) via a heating blanket controlled by the thermometer. Actual core temperature values were recorded at the time of MCA occlusion and at reperfusion. Ninety minutes after MCA occlusion, the rats were re-anaesthetised and the filament slowly and completely withdrawn to allow reperfusion. The arteriotomy is closed with diathermy, haemostasis was re-checked, and the cervical wound sutured closed.

Post-Occlusion Recovery

Following MCA occlusion, anaesthesia was discontinued and the animals allowed to regain consciousness under strict observation in an incubator (23-25° C.) for 1 hour. The animals were then housed individually in the post-operative recovery room, where their overall health status was closely monitored throughout the survival period.

Behavioural Tasks:

Neurological Assessment:

Motor and behavioural changes following MCA occlusion were assessed using a 28 point grading scale ("neuroscore", see example 10 for details) at time points 1 hour, 24 hours and then weekly for 8 weeks after MCA occlusion.

Cylinder Test:

Animals were assessed weekly in the cylinder test of forepaw placement. Animals were placed inside a transparent perspex cylinder 20 cm in diameter and 30 cm tall for a 3 minute period. The number of left, right and both forepaw placements whilst spontaneously rearing to explore the environment are assessed in this period. This test was conducted in red light conditions.

Tapered Beam Walking:

For this test all the rats are trained in a red light room to cross a square tapered beam of 1 m length at an angle of approx 40 degrees running uphill towards its homecage. This task becomes progressively more difficult as the rat moves up the beam as the width of the beam decreases.

Pre operative training—for 2 days each rat was taken from its homecage and placed onto the beam at increasing distances (approx 4 times in total). When each rat could cross the beam without coaxing and with few footfaults it is classed as trained. Any poor performers were excluded from the test.

Testing—each rat was placed on the beam 3 times per test session and the latency to cross, number of footslips, defined as a foot placement which does not achieve proper contact with the top surface of the beam, (hind and forelimb) was recorded by video, assessed at a later date and the average of these then taken. Test sessions for MCAO animals were prior to surgery, then post op at day 7 and weekly thereafter until sacrifice at week 8.

Dosing Regime (IV)

Antibody was administered intravenously at 1 hour, 24 hours, 1 week add 2 weeks following occlusion.

Groups:
A—2C4 3 mg/kg (4.7 mg/kg adjusted due to low MW fractions)
B—2A10 3 mg/kg
C—Control IgG2a 3 mg/kg
D—2A10 10 mg/kg All preparations were made in sterile saline.

Groups were blinded prior to administration.

To avoid bias introduced by the order of rats used, a Latin square design was employed. Animals were randomised and operators were blinded to treatment.

Neuropathology and Quantification of Ischaemic Damage 8 weeks after MCA occlusion, rats were perfusion fixed with ice-cold 4% paraformaledehyde. The animals were then decapitated and the brains stored in situ in ice-cold 4% paraformaledehyde for 48 hrs, prior to dissection and processing for paraffin embedding and subsequent histological analysis.

For brain volume analysis brains were serially sliced from the anterior pole to the cerebellum for paraffin processing at 2 mm intervals using a brain matrix. The brains are then paraffin processed and embedded in wax. 4 micron sections were collected that correspond to sterotactically pre-determined coronal planes from anterior +3 mm to posterior −7.5 mm relative to bregma. The sections were mounted on to poly lysine coated slides prior to staining with Haematoxylin and Eosin. The sections were analysed for lesion volume using a computer based image analysis system (Datacell, hardware. Optimas Software). Lesioned areas are delineated by areas of tissue with reduced Haematoxylin and Eosin. Lesions are measured by tracing around the boundaries of the lesioned area and expressed as % lesioned area compared to contralateral non lesioned side of the brain.

Statistical Analysis

The neuroscore and bodyweights data were analysed using a repeated measures ANOVA approach with time as the repeated measure. Lesion volume was analysed using a 1-way ANOVA and ANCOVA approach and lesion area was analysed using a repeated measures ANCOVA approach The footslips data were analysed separately for the fore and hind limbs, to look for a group effect, using a repeated measures ANOVA approach with week and beam difficulty as the repeated measures. To look for differences between fore and hind limbs, the footslips data were also analysed using a repeated measures ANOVA approach with week and leg as repeated measures, averaged across difficulty.

Results:
Lesion Volume:

FIG. 15 represents the lesion volume as a percentage of total brain volume. The antibody had no effect on lesion volume when compared to the control group.

Neuroscores

FIG. 16 shows the neuroscore data represented as means±SEM. Due to the large range of data observed parametric analysis was deemed by to be valid. *P<0.05 compared to control antibody, repeated measures ANOVA.

Cylinder Test

See FIGS. 17A, 17B and 17C. Cylinder data represented as mean±SEM for A) both paws, B) left paw, C) right paw. *P<0.05, **P<0.01 versus control antibody, repeated measures ANOVA.

Tapered Beam
Forelimb Footslips:

See FIG. 18. Forelimb footslips represented as mean±SEM. *P<0.05, **P<0.01 versus control antibody, repeated measures ANOVA.

Hind Limb Footslips

See FIG. 19. Hindlimb footslips represented as mean±SEM. *P<0.05 versus control antibody, repeated measures ANOVA.

Latency to Cross the Beam

See FIG. 20. Latency to cross beam represented as mean±SEM. *P<0.05 versus control antibody, repeated measures ANOVA.

Conclusions:

This study looked at the effect of two doses of the anti-NOGO antibody 2A10 (3 & 10 mg/kg) and one dose of 2C4 (3 mg/kg) on lesion volume and functional recovery after a 90 minute tMCAO when administered IV at 1 hour, 24 hours, 1 week and 2 weeks.

The antibody treatment had no effect on lesion volume.

The antibody treatment had a significant effect on neurological score at the highest dose of 2A10 (10 mg/kg) at 24 hours.

The 2A10 antibody treatment (3 mg/kg) had a significant effect on right paw use in the cylinder test specifically at weeks 1 and 2.

2A10 (3 mg/kg) had a clear effect of reducing the number of fore paw footslips at 1 and 2 weeks following tMCAO, 2A10 (10 mg/kg) had the effect of reducing hind paw footslips at 2 weeks following tMCAO, and both concentrations of 2A10 reduced latency to cross the beam at 1 week following tMCAO. 2C4 (3 mg/kg) reduced forepaw footslips at 3 weeks following tMCAO relative to control antibody.

Summary

In summary, although the treatment had no effect on lesion volume, intravenous injection of both the anti-NOGO monoclonal antibodies 2A10 and 2C4 had a positive effect on functional recovery, as assessed by neurological score, paw placement and tapered beam predominantly in the first two weeks following tMCAO.

EXAMPLE 12

Transfection of NOGO cDNA Into SHSY5Y-APP Cells

The day before transfection the SHSY5Y-APPwt cells were trypsinised, counted and replated at 200,000 to 1 million cells per well of a 6-well plate (Nunc). The NOGO expression construct (FLAG-tagged NOGO-A cDNA in pCDNA3 (Invitrogen); MYC-tagged NOGO-B and NOGO-C in pCDNA3.1A) was complexed with Plus™ reagent by diluting the DNA into serum free medium (OptiMEM-1), adding Plus™ reagent, mixing and incubating at room temperature for 15 min. (6 μl Plus reagent into a total volume of 100 μl with 2 μg DNA and OptiMEM-1 per well)

LipofectAMINE™ reagent was diluted into serum free medium (Optimem-I) in a second tube and mixed (4 μl Lipofectamine in 100 μl volume per well).

Pre-complexed DNA (from above) was combined with the diluted lipofectAMINE, mixed and incubated at room temp for 15 min.

Meanwhile the cells were washed with serum free medium (OptiMEM-I) and then fresh serum free medium was added to the cells (800μl per well).

The DNA-Plus-LipofectAMINE reagent complexes were then added to the cells (200 μl), mixed gently and the cells incubated at 37° C. for 5 hr in 5% $CO_2$.

After 5 hours 1 ml serum containing growth medium was added to the cells and the cells incubated overnight or 2 hours.

After 14 hours (or 2 hours) all medium was removed and replaced with 1 ml (OptiMEM-1) per well.

After 48 hours conditioning the medium was collected and assayed for amyloid content as described in example 13.

EXAMPLE 13

Detection of AB Peptide by IGEN ELISA

SHSY5Y cells overexpressing the human APPwt or Amyloid Precursor Protein Swedish variant sequence (APPswe) were seeded in 6 well or 96 well Nunc plates at the required density.

After 24 hours the reagents (eg. antibody, peptides, compounds etc) for testing were added to the cells in a final volume of 120 µl and cells incubated for 24 hr. The medium was removed from cells and 50 µl was assayed for Aβ x-40 and 50 µl for Aβ x-42 in an overnight ORIGEN immunoassay employing Aβ C-terminal specific antibodies. Briefly, Aβ peptides were captured using biotinylated 6E10 (Signet Labs). Ori-tagged labelled Aβ C-terminal specific antibodies were used to detect the Aβ x40 and Aβ x-42 species. Antibody-Aβ complexes were captured with streptavidin coated dynabeads and assayed in an IGEN M8 analyser. The viabiliy of the cells was checked using MTT (3-[4,5-Dimethylthiazol-2-yl]-2,5-diphenyltetrazolium bromide; Thiazolyl blue) reagent. Briefly, MTT reagent (5 mg/ml in phosphate buffered saline) was diluted 1:10 in culture medium and 100 µl added to each well. Following incubation at 37° C. for 4hr, 100 µl solubilising solution (20% SDS/50% Dimethyl Formamide) was added. Absorbance of plates was read using a Delfia Wallac plate reader at 590 nM.

The results are shown in FIGS. 21 to 34.

SHSY5Y-APPwt cells express wild-type APP. SHSY5Y-APPswe cells express the Swedish mutation form of APP.

EXAMPLE 14

The Effect of NOGO-A Expression on Levels of Secreted Aβ 40 and Aβ 42 Peptide When an expression construct expressing NOGO-A is introduced into either SHSY5Y-APPwt cells or SHSY5Y-APPswe cells the levels of Aβ 40 and Aβ 42 are seen to significantly increase suggesting that NOGO-A is in some way modulating, directly or indirectly, the proteolyic processing of APP and/Or degradation of Aβ peptides. The fact that the product of this altered APP processing is the peptide Aβ 40 could suggest that the effect of NOGO could be at the level of modulating β-secretase activity.

FIG. 21 shows the increase in the level of secreted Aβ40 when NOGO-A is expressed from an expression vector. The two left-hand bars are the controls (vector alone and vector carrying a control protein, green fluorescent protein (GFP)), showing the background levels of Aβ40 production in this cell-line. The remaining bars shows that significantly increased level of Aβ40 peptide are detected when NOGO-A, fused to a FLAG peptide, is expressed in the cells and also that a similar elevation, albeit less marked, when NOGO-B, fused to myc, is expressed.

Figure 22:
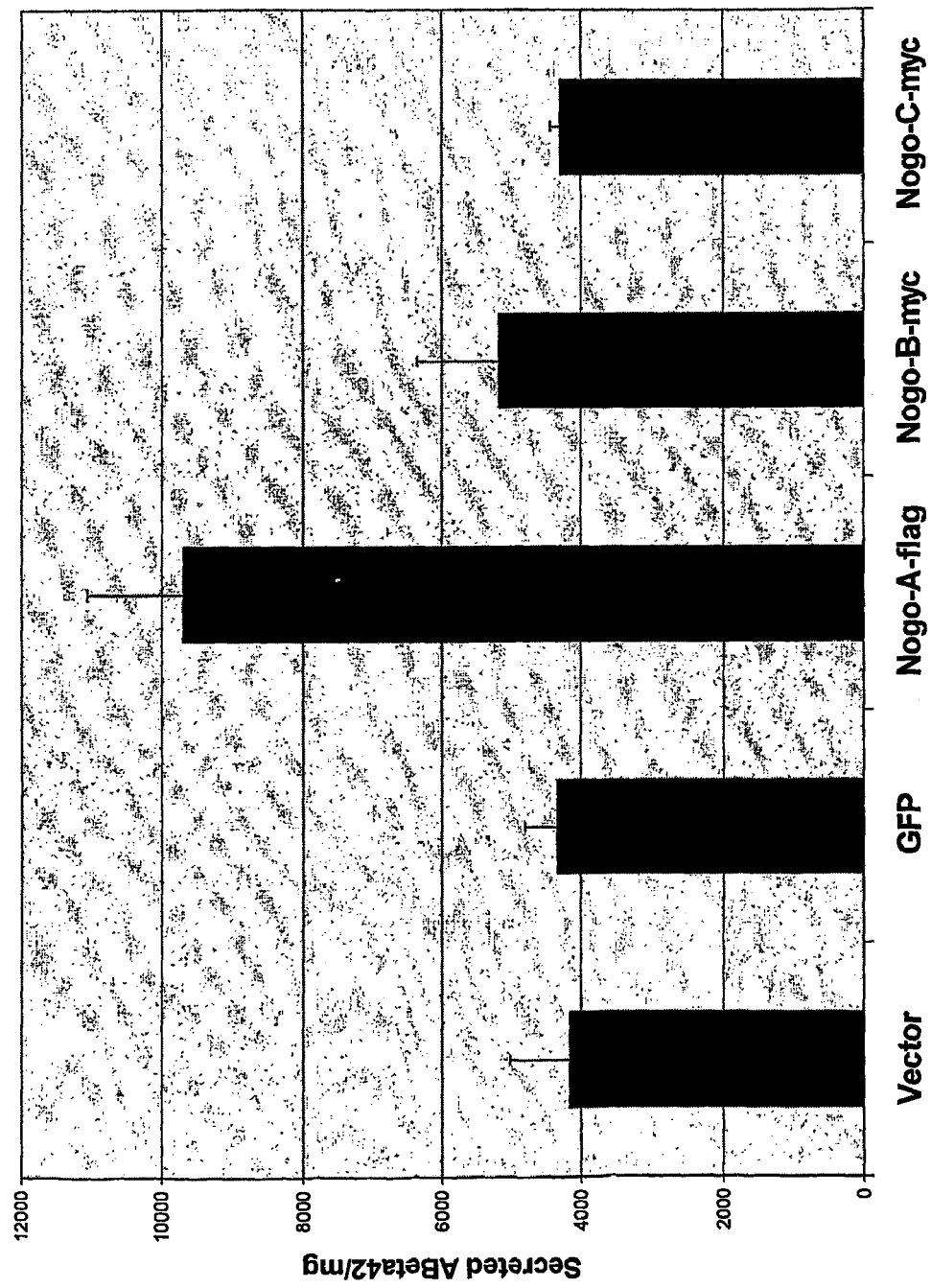

The same experiment was repeated using an ELISA specific for Aβ42. The results showed a similar elevation in levels of Aβ 42 peptide secretion as that seen in the earlier experiment using Aβ 40 ELISA. Again NOGO-B also showed increased secretion of Aβ 42 peptide and again the increase was less marked than with NOGO-A. The results are shown in FIG. 22.

Figure 23:
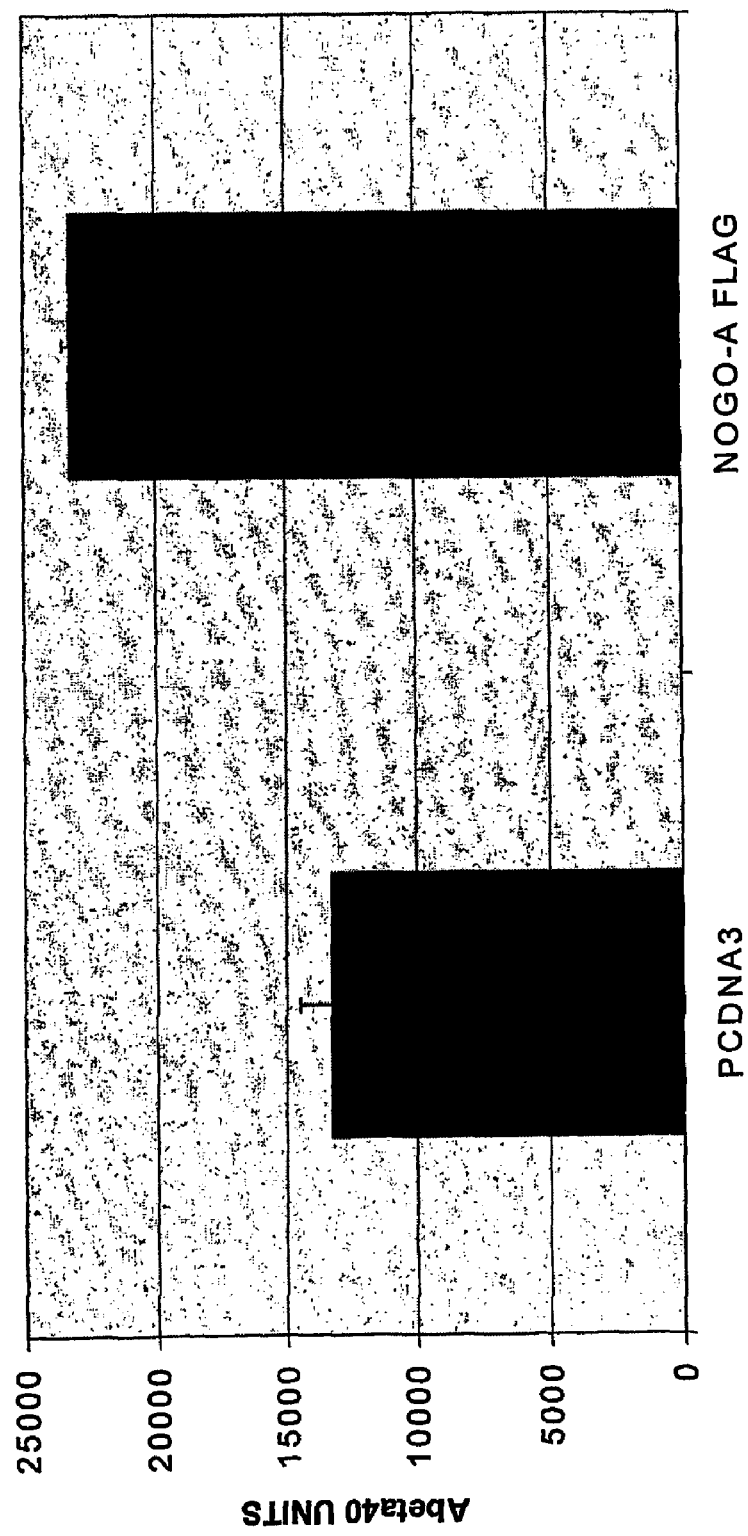
Figure 24:
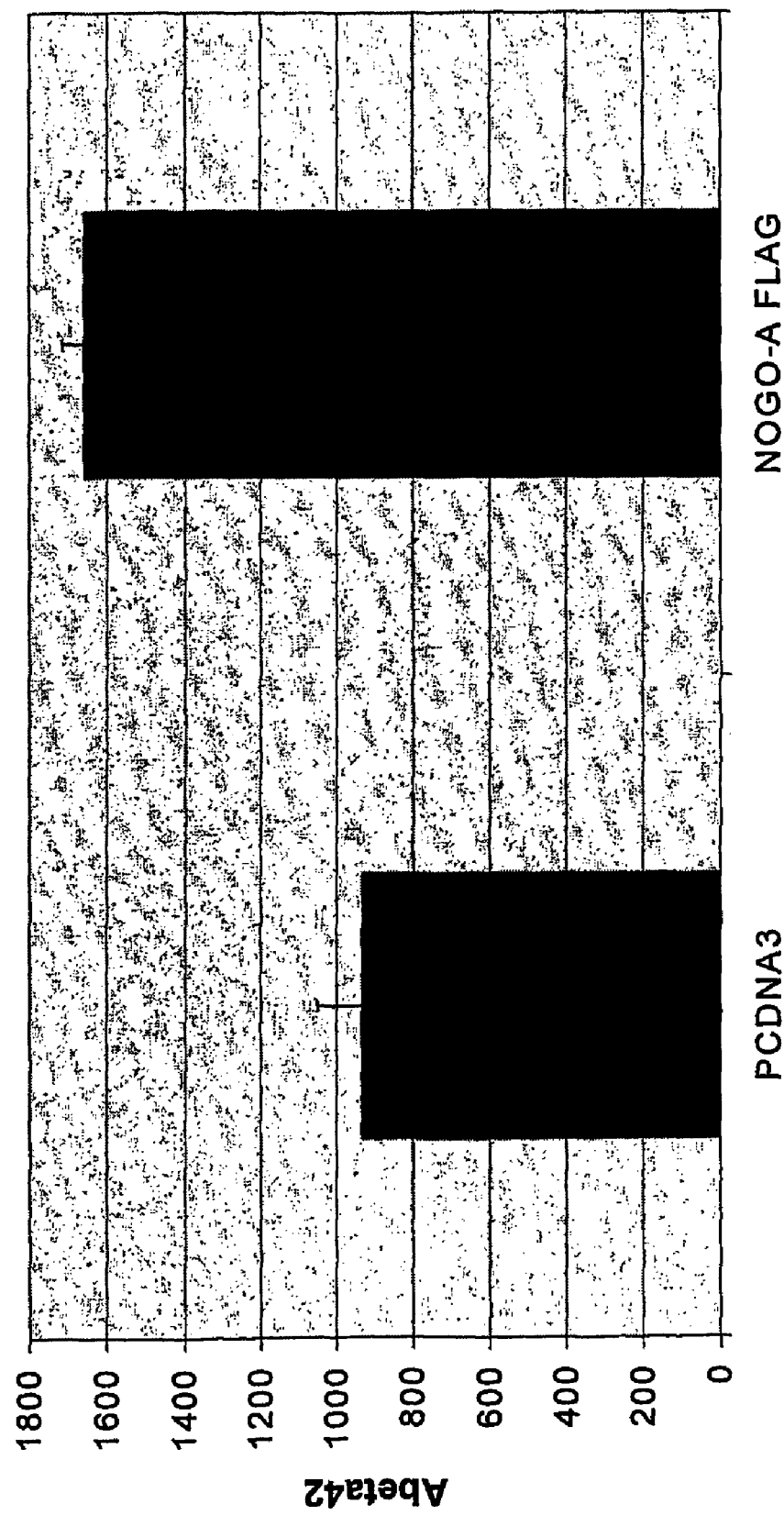

Repeat experiments comparing levels of secreted peptide from cells transfected with NOGO-A compared to vector pCDNA3 alone, are shown in FIGS. 23 (for Aβ 40) and 24 (for Aβ 42).

Figure 25:
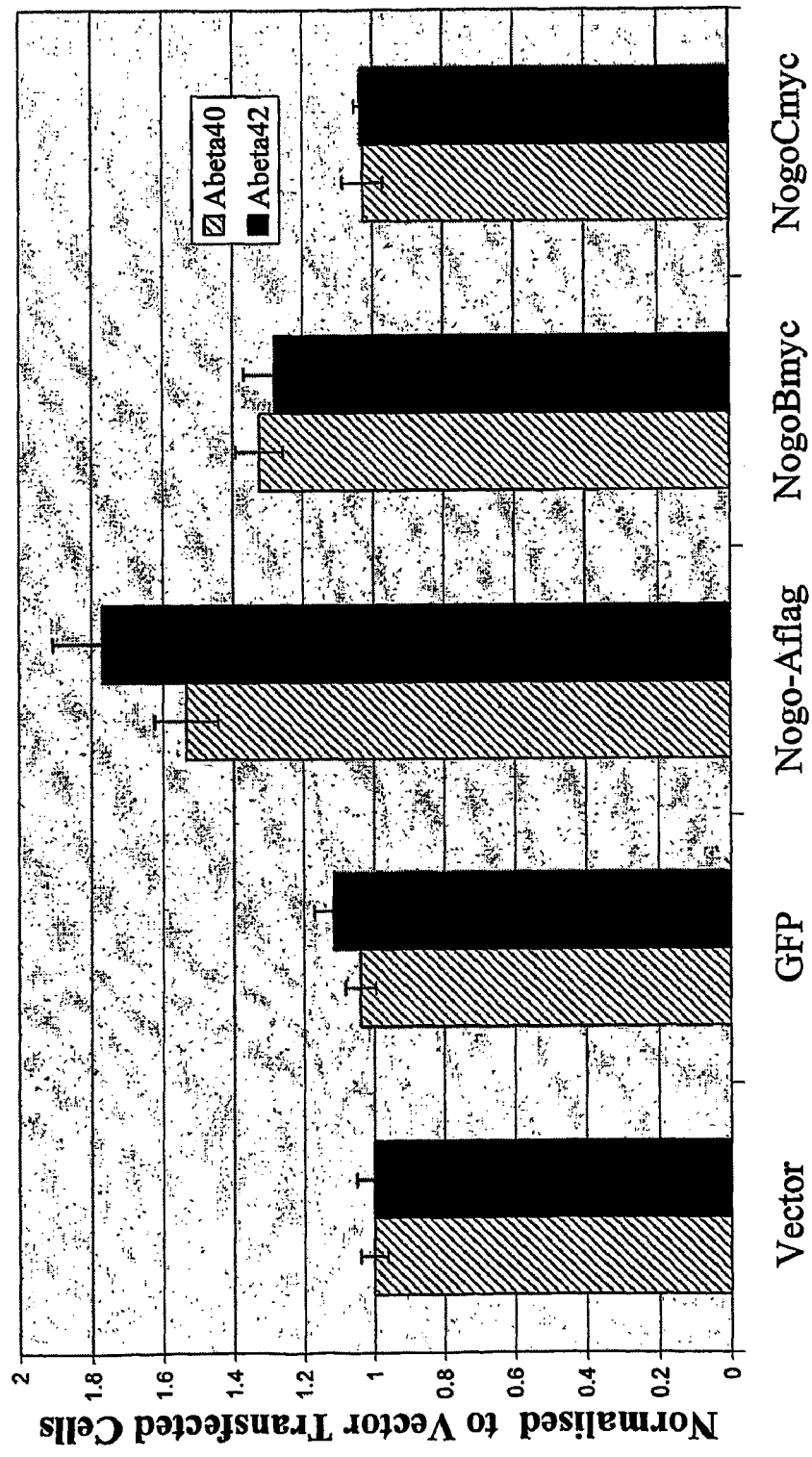

A direct comparison of levels of Aβ 40 and Aβ 42 peptide secreted is shown in FIG. 25. FIG. 25 is the average of three to five separate experiments to confirm the consistency of NOGO. Thus the invention provides the use of an anti-NOGO antibody (particularly an anti-NOGO-A and/or anti-NOGO-B antibody) in the manufacture of a medicament for the treatment of Alzheimer's disease.

EXAMPLE 15

Anti-NOGO-A Antibody Inhibits Aβ 40 and Aβ 42 Peptide Secretion from SHSY5Y-APPwt and SHSY5Yswe Cells FIG. 26 shows the dramatic reduction in levels of Aβ 40 and Aβ 42 peptide secreted from SHSY5Y-APPwt cells expressing endogenous NOGO-A when the anti-NOGO antibody 2A10 is introduced into the culture medium. The effect is seen in a dose-dependent manner, at 30 µg/ml reaching inhibition levels of almost 90%. There is no apparent difference in the effect between Aβ 40 and Aβ 42 peptides (white bars and black bars respectively in FIG. 26), in other words any effect of the anti-NOGO antibody on APP processing is not preferential for either the Aβ 40 or Aβ 42 peptides.

Figure 27:
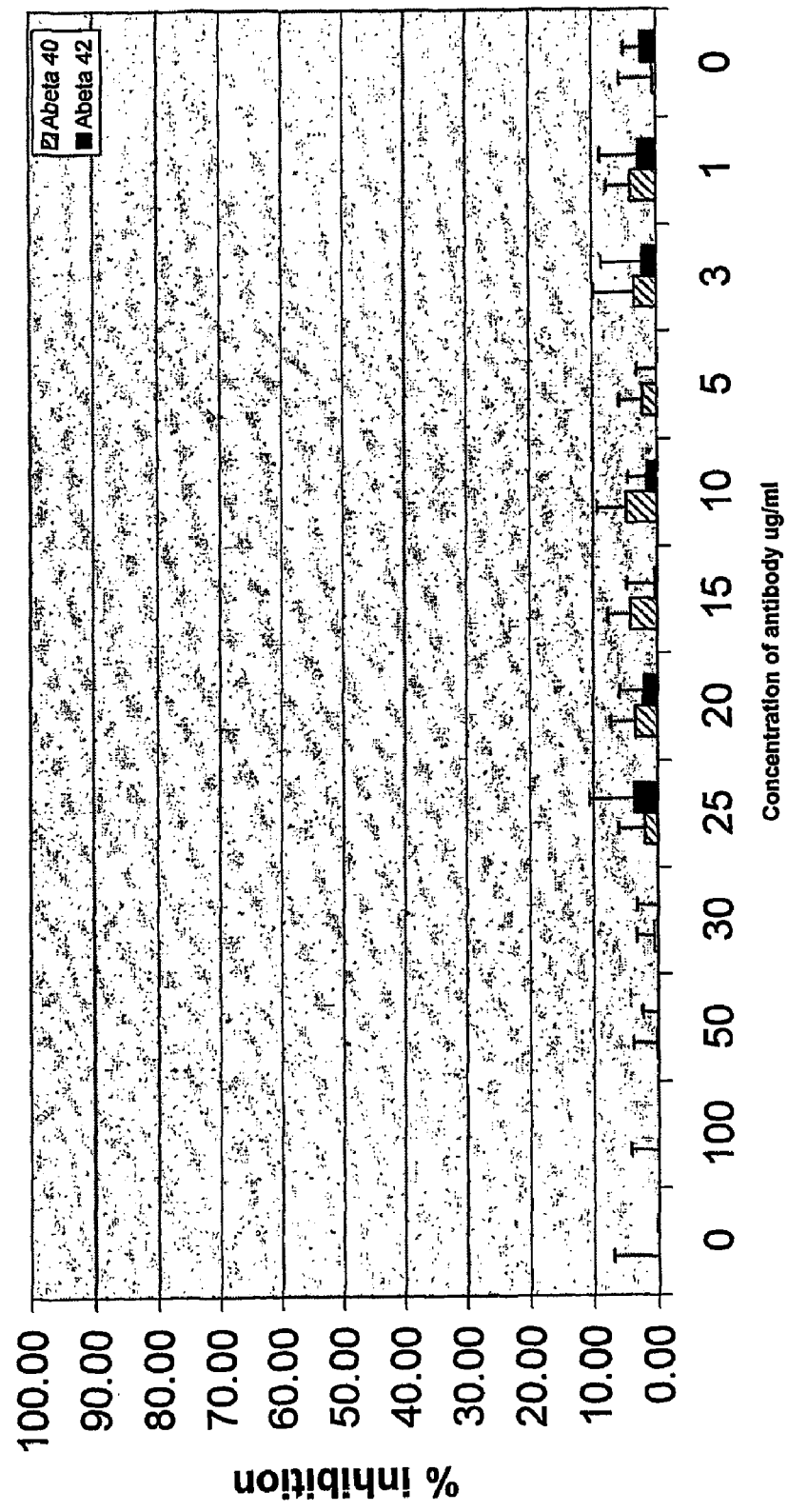

FIG. 27 shows the same experiment as in FIG. 26 but with an unrelated IgG1 antibody. As can clearly be seen in the figure, an unrelated (non anti-NOGO A) monoclonal antibody has no inhibitory effect on the levels of Aβ 40 and Aβ 42 peptide secretion from the cells.

Figure 28:
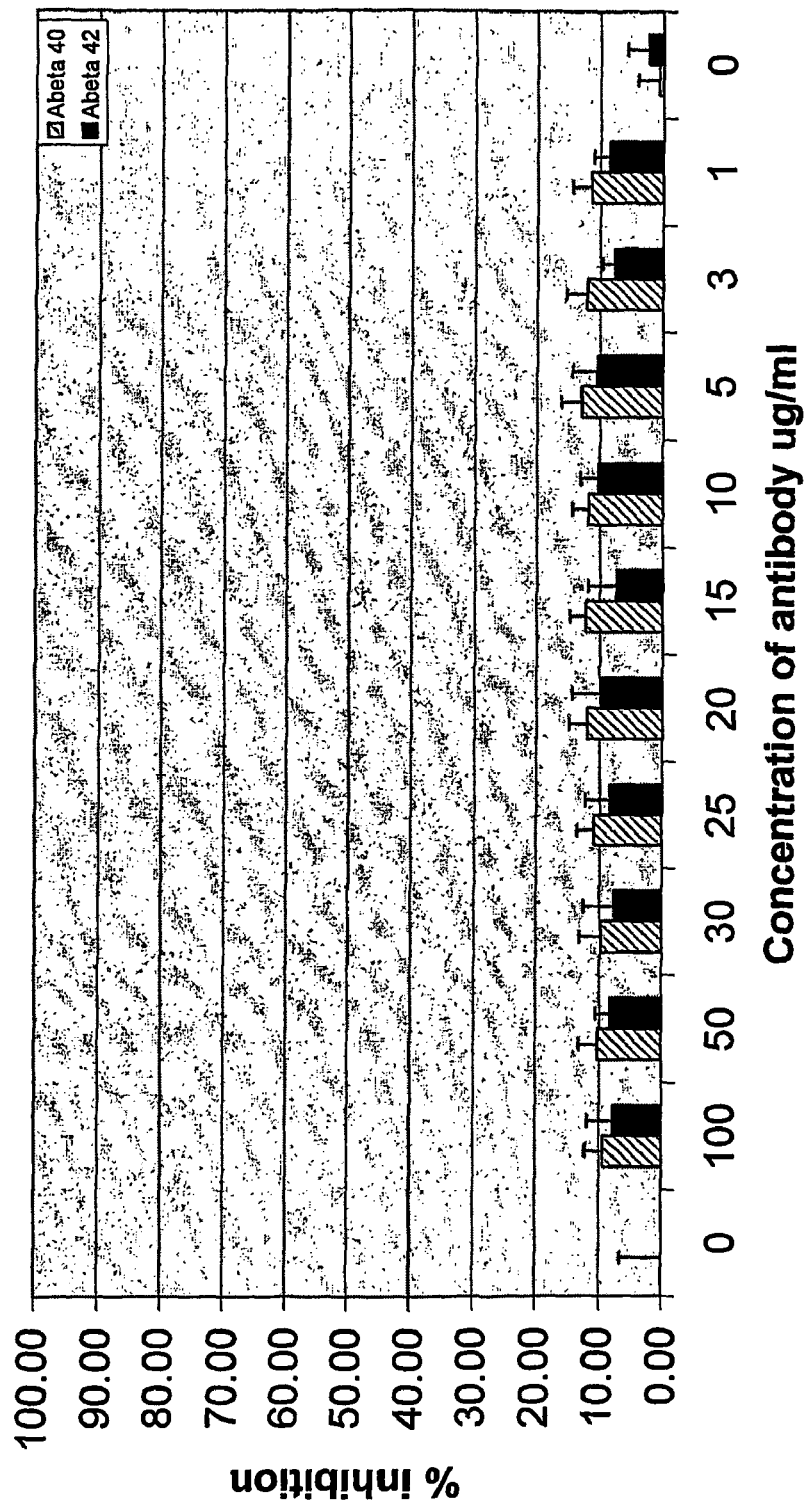

FIG. 28 shows that the same unrelated IgG1 antibody similarly shows little or no inhibitory effect on the levels of Aβ 40 and Aβ 42 peptide secretion from SHSY5Y-APPswe cells expressing NOGO-A.

Figure 29:
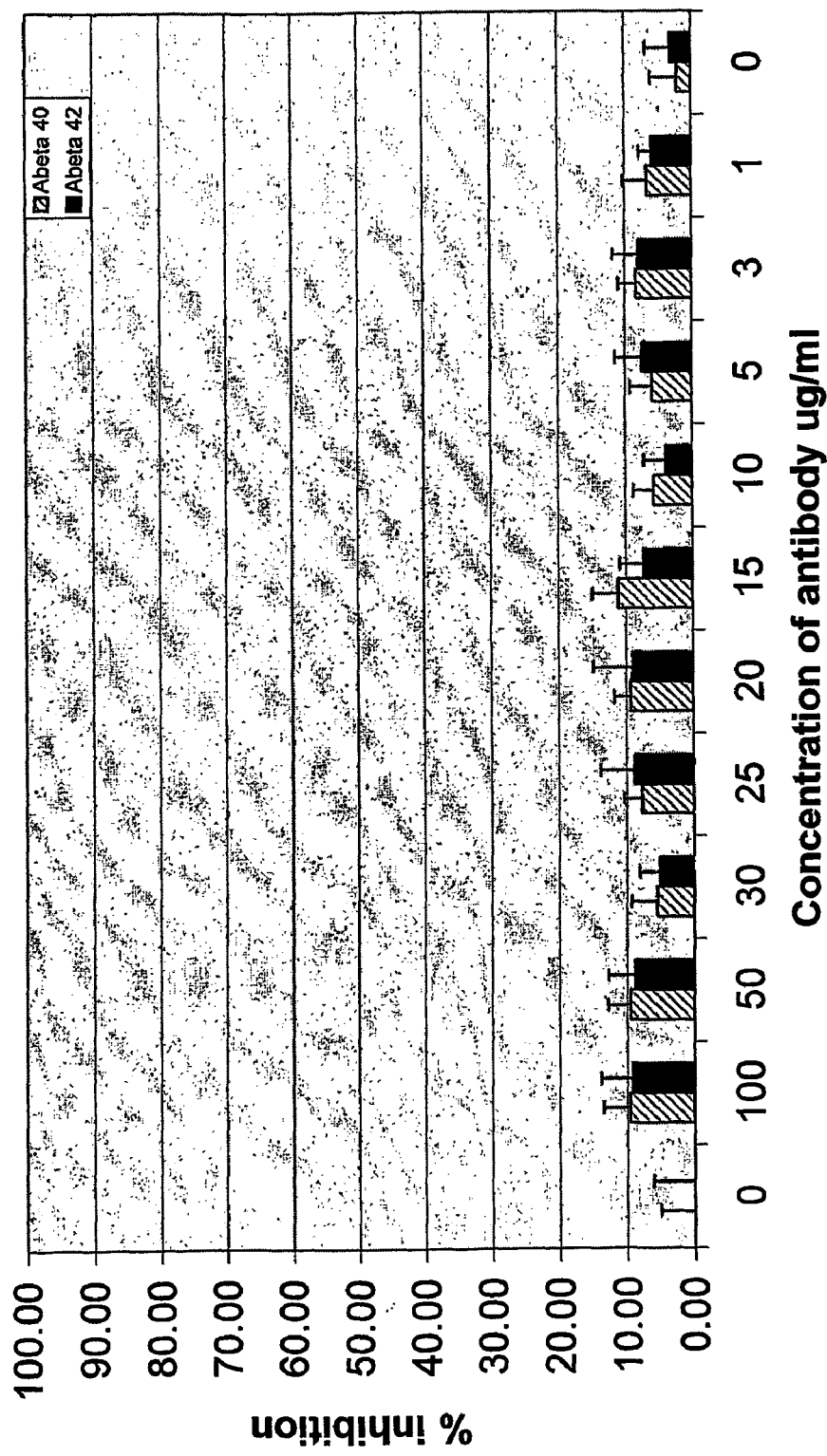

Similarly FIG. 29 shows the results of the same experiment as described above for FIG. 26 but using an anti-NOGO monoclonal antibody which binds to NOGO-A but is not a function-blocker (6D5). The non-function-blocking anti-NOGO-A monoclonal antibody has minimal effect (less than 10%) on the secretion of Aβ 40 and Aβ 42 peptides from SHSY5Y-APPwt cells expressing NOGO-A. This result suggests that the results shown in FIG. 26 are a result of the inhibition of NOGO functional activity by the anti-NOGO antibody.

Figure 30:
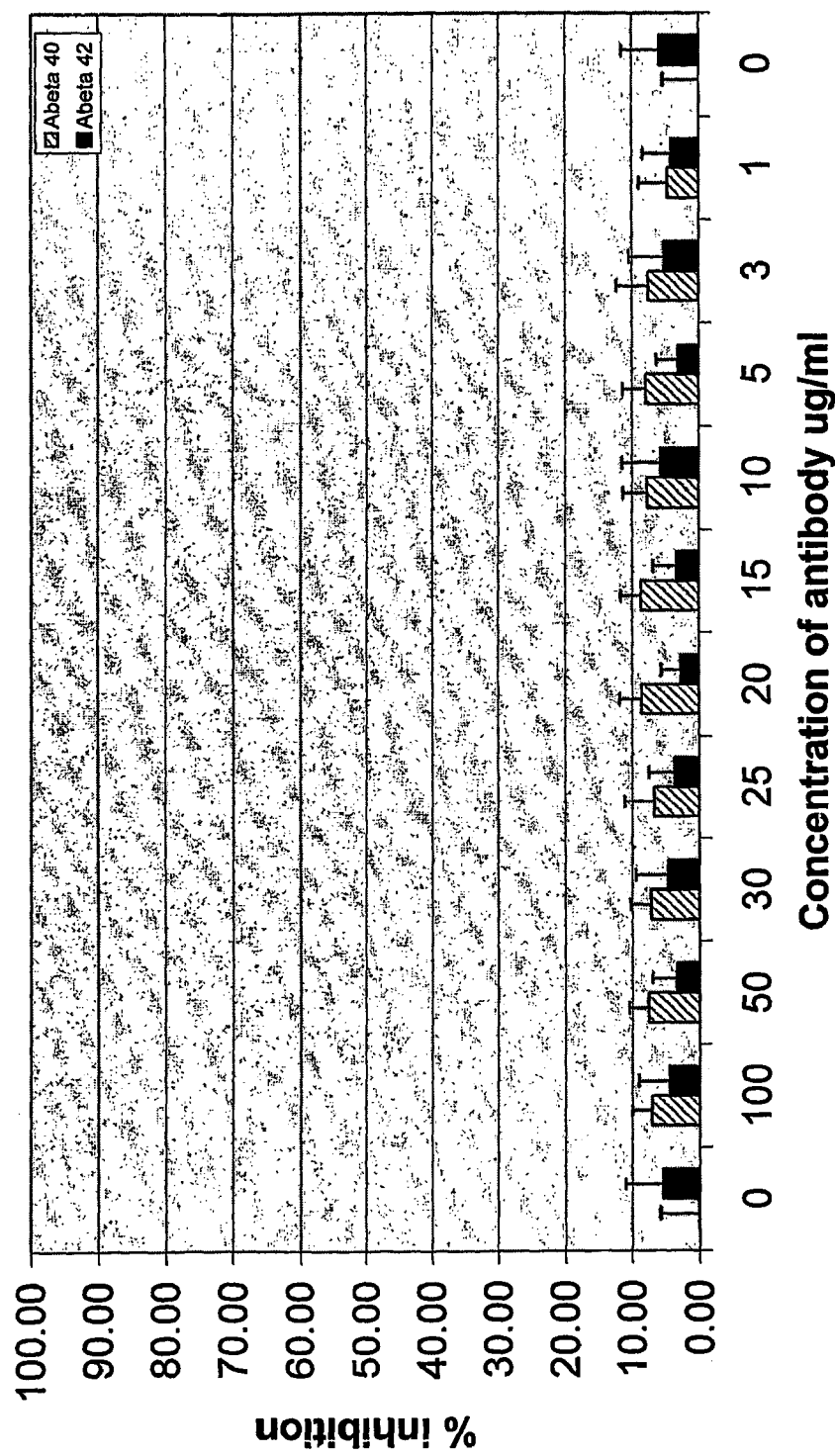

FIG. 30 shows the results of the same experiment as for FIG. 29, using the non-function blocking anti-NOGO monoclonal antibody (6D5) but with SHSY5Y -APPswe cells expressing endogenous NOGO-A. As before (FIG. 29) there is minimal effect on the levels of Aβ 40 and Aβ 42 being secreted by this cell line, being less than 10% inhibition.

Figure 31:
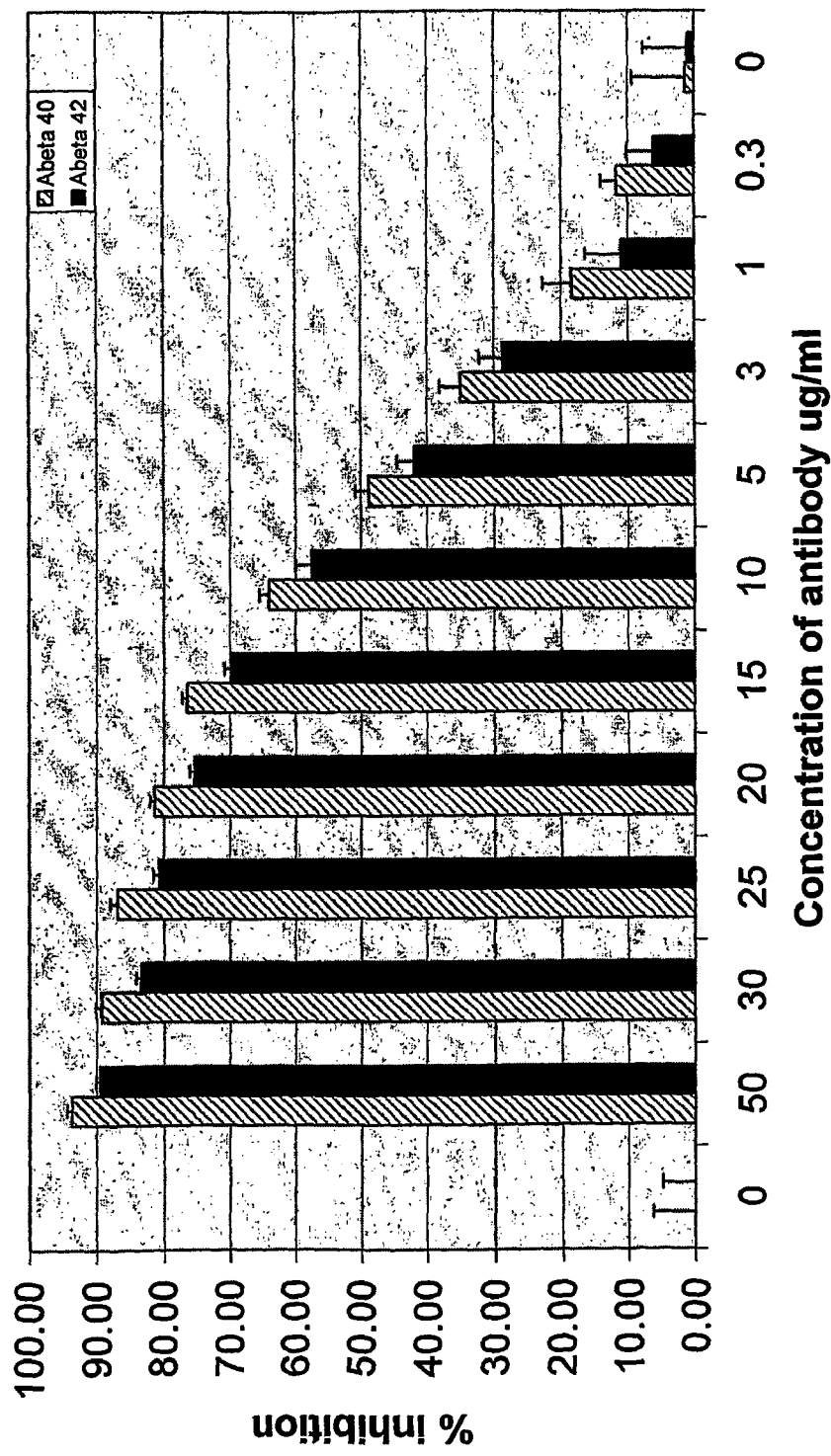

FIG. 31 shows the results of an experiment which extends the results of the experiment of FIG. 26. FIG. 31 shows that the concentration-dependent effect of the inhibitory effect shown by the function-blocking antibody 2A10/3 continues at a higher concentration, a level of greater than 90% inhibition being achieved at an antibody concentration of 50 µg/ml.

Figure 32:
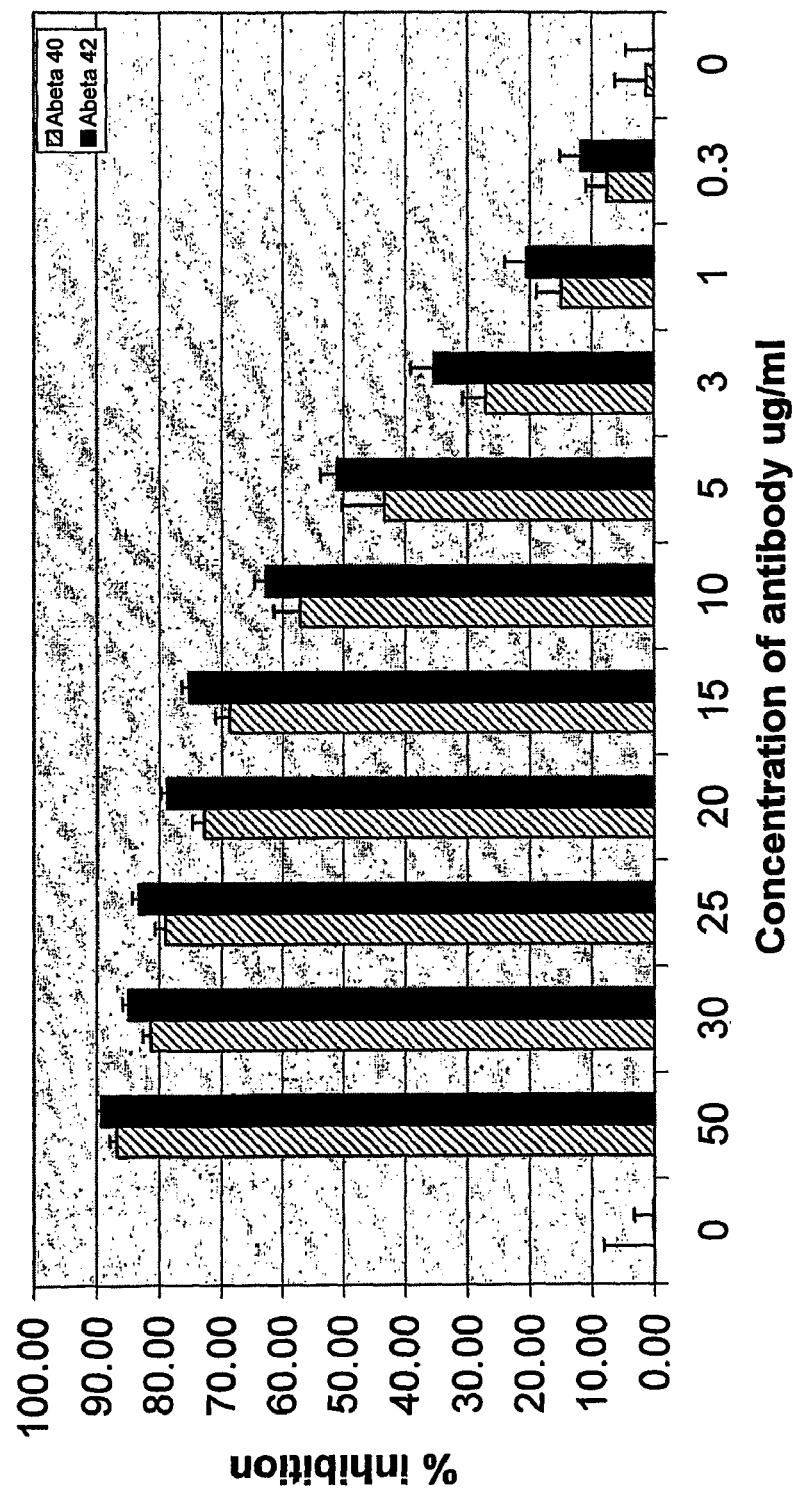

FIG. 32 shows the results of an identical experiment to that of FIG. 31 except that SHSY5Yswe cells are used. The concentration-dependent inhibitory effect of the antibody 2A10/3 continues to be seen at the higher concentration of 50 µg/ml.

Figure 33:
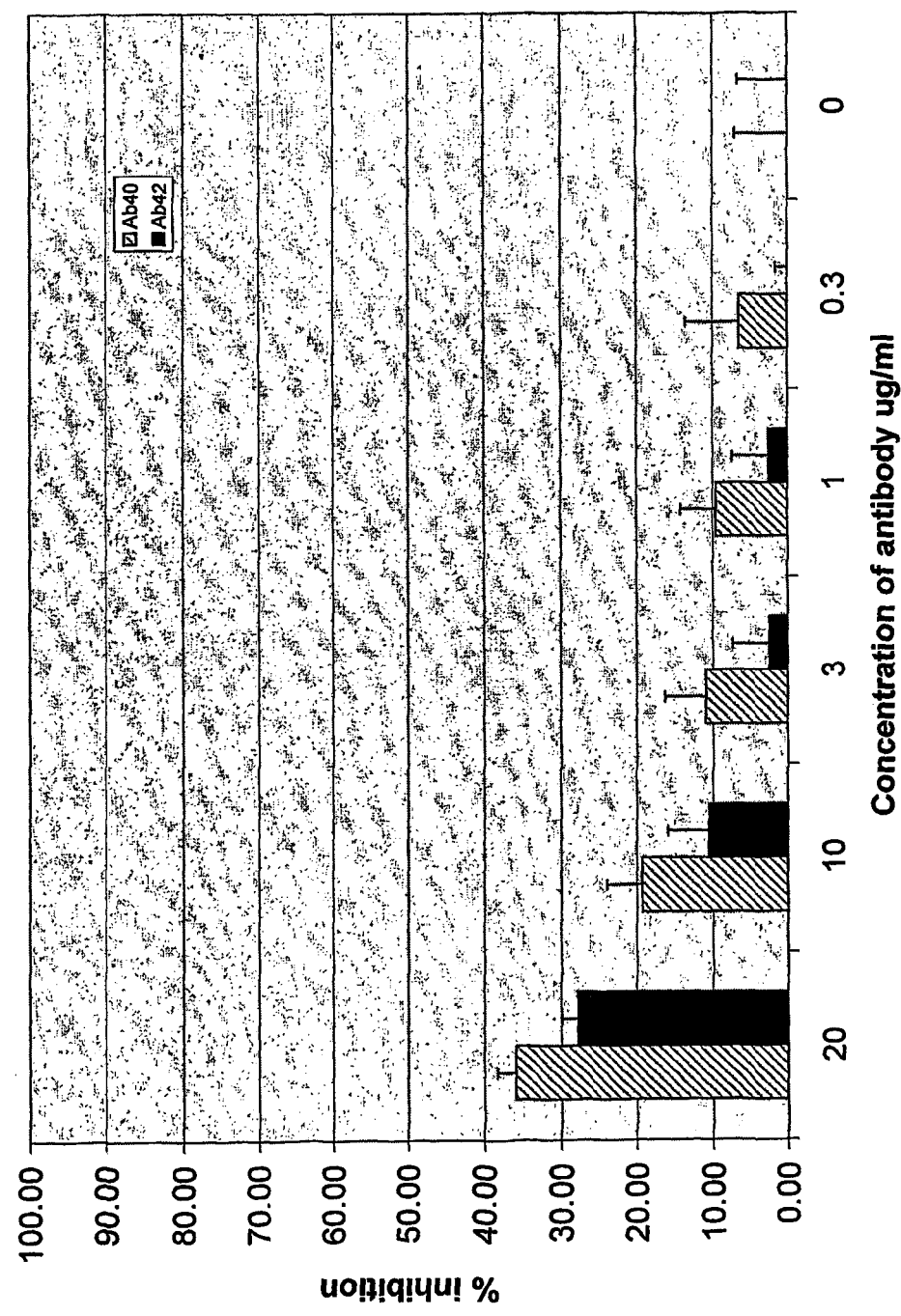

FIG. 33 shows the effect of a different function-blocking anti-NOGO-A antibody, 2C4, on the secretion of Aβ 40 and Aβ 42 peptides from SHSY5Y-APPwt cells. The results show a concentration-dependent inhibitory effect on the levels of Aβ 40 and Aβ 42 peptide secretion to a level of 36% at ac oncentration of 20 μg/ml.

Again the effect is seen on both Aβ 40 and Aβ 42 peptides.

Figure 34:
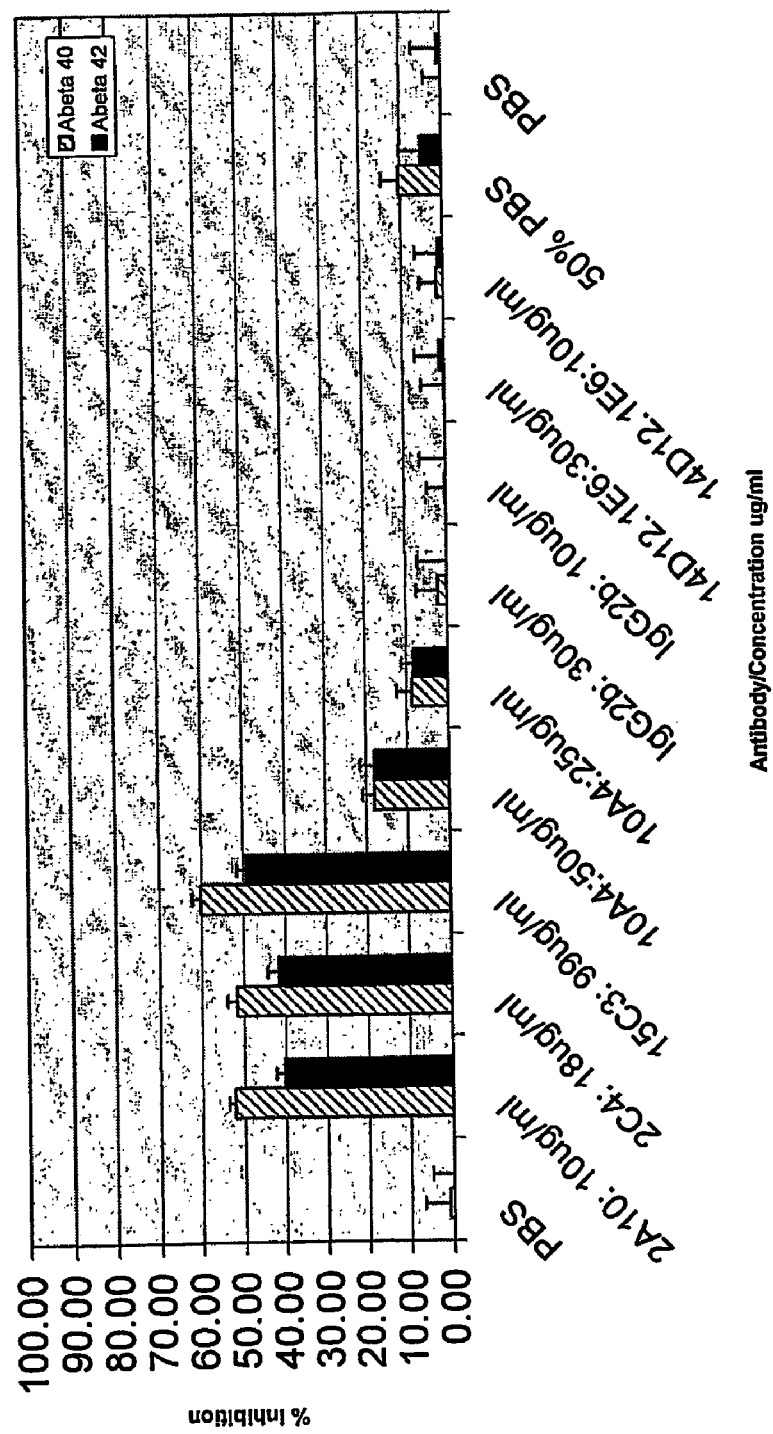

FIG. 34 compares the inhibitory effect of the anti-NOGO-A function-blocking antibodies 2A10, 2C4 and 15C3 (at the concentrations shown in the figure) with other control antibodies 10A4, IgG2b and 14D12. The figure shows that the effect on inhibition of Aβ 40 and Aβ 42 secretion is specific to the function-blocking anti-NOGO-A monoclonal, antibodies.

EXAMPLE 16

Increased NogoA Expression Elevates Aβ Levels in a Dose-Dependent Manner

To investigate the effect of NogoA expression on Aβ levels, SHSY5Y-APPwt cells were transiently transfected with increasing amounts of C-terminal myc tagged NogoA cDNA. The total amount of cDNA (5 ug) was kept constant for each transfection using pcDNA3.1myc cDNA. 48 hr post-transfection, culture medium was removed and assayed for Aβ40. In addition, cells were harvested and lysed in 10 mM Tris/HCl containing 1% Triton X-100 and Complete protease inhibitors (Roche). Cell lysates were resolved on 10% Novex Tris-glycine gels and subject to Western blot analysis with an anti-NogoA antibody. An increase in NogoA protein expression was observed with increasing NogoA cDNA concentrations. This was concomitant with a corresponding increase in Aβ40 levels in the medium from these cells. Thus, increased expression of NogoA causes a dose-dependent increase in Aβ40 levels. See FIG. 36.

EXAMPLE 17

Chimeric 2A10 (HcLc)

A chimaeric antibody consisting of parent murine V regions grafted onto human IgG1/k wild type C regions was designed to be used as a reference when testing humanised constructs. The NOGO 2A10 $V_H$ domain in the mouse recombinant RId plasmid was cut Hind III-Spe I and ligated into the RId vector containing hCγ1wt. The NOGO 2A10 $V_I$ domain in the mouse recombinant RIn plasmid was cut Hind III-BsiW I and ligated into the RIn vector containing hCk.

SEQ.I.D.NO:92 sets forth the heavy chain sequence for HcLc

```
MGWSCIILFLVAAATGVHSQVQLQQPGTELVKPGASVKLSCKASGYTFTSYWMHWVKQRP    (SEQ.I.D.NO: 92)

GQGLEWIGNINPSNGGTNYNEKFKSKATLTVDKSSSTAYMQLSSLTSEDSAVYYCELGQG

YWGQGTLVTVSSASTKGPSVFPLAPSSKSTSGGTSSLGCLVKDYFPEPVTVSWNSGALTS

GVHTFPAVLQSSGLYSLSSVVTVPSSSLGTQTYICNVNHKPSNTKVDKKVEPKSCDKTHT

CPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTTPPVLDSDGSFF

LYSKLTVDKSRWQQGNVFSCSVMHEALHNHYTQKSLSLSPGK
```

A polynucleotide encoding SEQ.I.D.NO:92 is set forth as SEQ.I.D.NO:93.

```
AAGCTTGCCACCATGGGATGGAGCTGTATCATCCTCTTTTTGGTAGCAGCAGCTACAGGT    (SEQ.I. D.NO: 93).

GTCCACTCCCAGGTCCAACTGCAGCAGCCTGGGACTGAACTGGTGAAGCCTGGGGCTTCA

GTGAAGCTGTCCTGCAAGGCTTCTGGCTACACCTTCACCAGCTACTGGATGCACTGGGTG

AAGCAGAGGCCTGGACAAGGCCTTGAGTGGATTGGAAATATTAATCCTAGCAATGGTGGT

ACTAACTACAATGAGAAGTTCAAGAGCAAGGCCACACTGACTGTAGACAAATCCTCCAGC

ACAGCCTACATGCAGCTCAGCAGCCTGACATCTGAGGACTCTGCGGTCTATTATTGTGAA

CTGGGACAGGGCTACTGGGGCCAAGGCACACTAGTCACAGTCTCCTCAGCCTCCACCAAG

GGCCCATCGGTCTTCCCCCTGGCACCCTCCTCCAAGAGCACCTCTGGGGGCACAGCGGCC

CTGGGCTGCCTGGTCAAGGACTACTTCCCCGAACCGGTGACGGTGTCGTGGAACTCAGGC

GCCCTGACCAGCGGCGTGCACACCTTCCCGGCTGTCCTACAGTCCTCAGGACTCTACTCC

CTCAGCAGCGTGGTGACCGTGCCCTCCAGCAGCTTGGGCACCCAGACCTACATCTGCAAC

GTGAATCACAAGCCCAGCAACACCAAGGTGGACAAGAAAGTTGAGCCCAAATCTTGTGAC

AAAACTCACACATGCCCACCGTGCCCAGCACCTGAACTCCTGGGGGGACCGTCAGTCTTC

CTCTTCCCCCCAAAACCCAAGGACACCCTCATGATCTCCCGGACCCCTGAGGTCACATGC
```

```
GTGGTGGTGGACGTGAGCCACGAAGACCCTGAGGTCAAGTTCAACTGGTACGTGGACGGC

GTGGAGGTGCATAATGCCAAGACAAAGCCGCGGGAGGAGCAGTACAACAGCACGTACCGT

GTGGTCAGCGTCCTCACCGTCCTGCACCAGGACTGGCTGAATGGCAAGGAGTACAAGTGC

AAGGTCTCCAACAAAGCCCTCCCAGCCCCCATCGAGAAAACCATCTCCAAAGCCAAAGGG

CAGCCCCGAGAACCACAGGTGTACACCCTGCCCCCATCCCGGGATGAGCTGACCAAGAAC

CAGGTCAGCCTGACCTGCCTGGTCAAAGGCTTCTATCCCAGCGACATCGCCGTGGAGTGG

GAGAGCAATGGGCAGCCGGAGAACAACTACAAGACCACGCCTCCCGTGCTGGACTCCGAC

GGCTCCTTCTTCCTCTACAGCAAGCTCACCGTGGACAAGAGCAGGTGGCAGCAGGGGAAC

GTCTTCTCATGCTCCGTGATGCATGAGGCTCTGCACAACCACTACACGCAGAAGAGCCTC

TCCCTGTCTCCGGGTAAATGAATTC.
```

The amino acid sequence of the light chain of HcLc is set forth as SEQ.I.D.NO:94:

```
                                              (SEQ.I.D.NO:94)
MRCSLQFLGVLMFWISGVSGDIVITQDELSNPVTSGESVSISCRSSKSLL

YKDGKTYLNWFLQRPGQSPQLLIYIMSTRASGVSDRFSGSGSGTDFTLEI

SRVKAEDVGVYYCQQLVEYPLTFGAGTKLELKRTVAAPSVFIFPPSDEQL

KSGTASVVCLLNNFYPREAKVQMKVDNALQSGNSQESVTEQDSKDSTYSL

SSTLTLSKADYEKHKVYACEVTHQGLSSPVTKSFNRGEC
```

A polynucleotide encoding SEQ.I.D.NO:94 is set forth as SEQ.I.D.NO:95:

```
                                              (SEQ.I.D.NO:95)
AAGCTTGCCACCATGAGGTGCTCTCTTCAGTTTCTGGGGGTGCTTATGTT

CTGGATCTCTGGAGTCAGTGGGGATATTGTGATAACCCAGGATGAACTCT

CCAATCCTGTCACTTCTGGAGAATCAGTTTCCATCTCCTGCAGGTCTAGT

AAGAGTCTCCTATATAAGGATGGGAAGACATACTTGAATTGGTTTCTGCA

GAGACCAGGACAATCTCCTCAGCTCCTGATCTATTTGATGTCCACCCGTG

CATCAGGAGTCTCAGACCGGTTTAGTGGCAGTGGGTCAGGAACAGATTTC

ACCCTGGAAATCAGTAGAGTGAAGGCTGAGGATGTGGGTGTGTATTACTG

TCAACAACTTGTAGAGTATCCGCTCACGTTCGGTGCTGGGACCAAGCTGG

AGCTGAAACGTACGGTGGCTGCACCATCTGTCTTCATCTTCCCGCCATCT

GATGAGCAGTTGAAATCTGGAACTGCCTCTGTTGTGTGCCTGCTGAATAA

CTTCTATCCCAGAGAGGCCAAAGTACAGTGGAAGGTGGACAACGCCCTCC

AATCGGGTAACTCCCAGGAGAGTGTCACAGAGCAGGACAGCAAGGACAGC

ACCTACAGCCTCAGCAGCACCCTGACGCTGAGCAAAGCAGACTACGAGAA

ACACAAAGTCTACGCCTGCGAAGTCACCCATCAGGGCCTGAGCTCGCCCG

TCACAAAGAGCTTCAACAGGGGAGAGTGTTAGGAATTC
```

EXAMPLE 18

Humanised Anti-NOGO Antibodies Bind to Human NOGO

GST-human NOGO-A56 at 1 μg/ml in 50 mM Tris pH9.5 was coated onto Nunc Immunosorp plates (100 μl per well) at 4° C. overnight. Wells were rinsed once with TBS+0.05% tween then incubated with 2% BSA in TBS+0.05% tween to block non-specific binding sites at room temperature for 1hour. Antibodies were diluted in TBS+0.05% tween+2% BSA to 10 μg/ml and ½ dilutions made from this. Antibodies were added to wells in duplicate and incubated at room temperature for 1 hour. Wells were washed three times with TBS+0.05% tween then incubated with anti-human kappa peroxidase conjugate (1:2000) for 1 hour. Washed three times with TBS+0.05% tween and then incubated with 100 μl OPD peroxidase substrate (Sigma) per well for 10 minutes. The colour reaction was stopped by the addition of 25 μl concentrated $H_2SO_4$. Optical density at 490 nm was measured using a plate reader. Background values read from wells with no antibody were subtracted.

FIGS. 35A to C illustrates the dose-dependent binding of humanised antibody H1L11 in comparison with the chimera (HcLc) to human NOGO-A56 in an ELISA assay. The Y-axis shows the measured optical density (OD) at 490 nm, a quantitative measure of antibody captured in the wells. The X-axis shows the concentration of antibody used (ug/ml) per well at each data point. Antibodies H1L11 and HcLc give EC50 values of 0.118 μg/ml and 0.022 μg/ml respectively.

---

The invention claimed is:

1. An isolated antibody or functional fragment thereof which binds with and neutralises human NOGO-A wherein said antibody or functional fragment thereof comprises each of the following CDRs:
- CDRL1 as set forth in SEQ ID NO: 1;
- CDRL2 as set forth in SEQ ID NO: 2;
- CDRL3 as set forth in SEQ ID NO: 3;
- CDRH1 as set forth in SEQ ID NO: 4;
- CDRH2 as set forth in SEQ ID NO: 5; and
- CDRH3 as set forth in SEQ ID NO: 6 or an analog of CDRH3 wherein the amino acid sequence of CDRH3 is modified by one amino acid.

2. An isolated antibody according to claim 1 which binds to SEQ ID NO: 87.

3. An isolated antibody according to claim 1 wherein CDRH3 is as set forth in SEQ ID NO: 6.

4. An isolated antibody of claim 1 which is a monoclonal antibody.

5. An isolated antibody of claim 1 which is a humanised or chimeric antibody.

6. An isolated antibody according to claim 1 wherein the heavy chain variable region comprises the amino acid sequence set forth in SEQ ID NO: 37.

7. An isolated antibody according to claim 1 wherein the light chain variable region comprises the amino acid sequence set forth in SEQ ID NO: 40.

8. A pharmaceutical composition comprising an isolated anti-NOGO antibody or functional fragment thereof according to claim 1 together with a pharmaceutically acceptable diluent or carrier.

9. The method of treatment or prophylaxis of stroke and other neurological diseases/disorders in a human which comprises administering to said human in need thereof an effective amount of an anti-NOGO antibody, according to claim 1, including altered antibodies or a functional fragment thereof.

10. An isolated functional fragment of the antibody according to claim 1 which binds to SEQ ID NO: 87.

11. An isolated functional fragment of the antibody according to claim 1.

12. An isolated functional fragment of the antibody according to claim 3.

* * * * *